(12) United States Patent
Guo et al.

(10) Patent No.: US 11,370,807 B2
(45) Date of Patent: Jun. 28, 2022

(54) PROCESS FOR PREPARING SULFONAMIDE COMPOUNDS

(71) Applicants: Ascentage Pharma (Suzhou) Co., Ltd., Suzhou (CN); Ascentage Pharma Group Corp Limited, Hong Kong (CN)

(72) Inventors: Ming Guo, Suzhou (CN); Jianfeng Wen, Suzhou (CN); Huirong Lu, Suzhou (CN); Jianpeng Feng, Suzhou (CN); Jing Zhang, Suzhou (CN); Ming Jin, Suzhou (CN); Qianlei Cao, Suzhou (CN)

(73) Assignees: Ascentage Pharma (Suzhou) Co., Ltd., Suzhou (CN); Ascentage Pharma Group Corp Limited, Hong Kong (CN)

( * ) Notice: Subject to any disclaimer, the term of this patent is extended or adjusted under 35 U.S.C. 154(b) by 0 days.

(21) Appl. No.: 16/763,350

(22) PCT Filed: Jan. 3, 2020

(86) PCT No.: PCT/CN2020/070163
§ 371 (c)(1),
(2) Date: May 12, 2020

(87) PCT Pub. No.: WO2020/140956
PCT Pub. Date: Jul. 9, 2020

(65) Prior Publication Data
US 2022/0009952 A1 Jan. 13, 2022

(30) Foreign Application Priority Data

Jan. 4, 2019 (WO) ............... PCT/CN2019/070508

(51) Int. Cl.
*C07F 9/6558* (2006.01)
*C07D 207/36* (2006.01)
*C07D 211/62* (2006.01)
*C07F 9/59* (2006.01)

(52) U.S. Cl.
CPC ........ *C07F 9/65583* (2013.01); *C07D 207/36* (2013.01); *C07D 211/62* (2013.01); *C07F 9/59* (2013.01); *C07B 2200/07* (2013.01)

(58) Field of Classification Search
CPC .................................................. C07F 9/65583
See application file for complete search history.

(56) References Cited

FOREIGN PATENT DOCUMENTS

| WO | WO 2012/103059 A2 | 8/2012 |
|----|-------------------|--------|
| WO | WO 2014/113413 A1 | 7/2014 |

OTHER PUBLICATIONS

Database Registry, RN 2227198-85-6 (Jun. 19, 2018). American Chemical Society; retrieved from STN International on Mar. 1, 2020; 2 printed pages.
Database Registry, RN 2227199-29-1 (Jun. 19, 2018). American Chemical Society; retrieved from STN International on Mar. 1, 2020; 3 printed pages.

*Primary Examiner* — Laura L Stockton
(74) *Attorney, Agent, or Firm* — Cooley LLP; Heidi A. Erlacher; Xixi Sun

(57) ABSTRACT

The present invention relates to a process for preparing a sulfonamide compound which is an inhibitor of Bcl-2/Bcl-xL, including the compound (3R)-1-(3-(4-(4-(4-(3-(2-(4-chlorophenyl)-1-isopropyl-4-methylsulfonyl-5-methyl-1H-pyrrol-3-yl)-5-fluorophenyl)piperazine-1-yl)-phenylaminosulfonyl)-2-trifluoromethanesulfonyl-anilino)-4-phenylthio-butyl)-piperidine-4-carboxylic acid 3-phosphonopropyl ester. The present invention also relates to an intermediate for preparing the sulfonamide compound and a preparation process thereof.

11 Claims, No Drawings

PROCESS FOR PREPARING SULFONAMIDE COMPOUNDS

RELATED APPLICATIONS

This application is a U.S. National Phase Application, filed under 35 USC § 371, of International Application No. PCT/CN2020/070163, filed on Jan. 3, 2020, which claims priority to, and the benefit of, International Application No. PCT/CN2019/070508, filed on Jan. 4, 2019, the contents of each of which are incorporated by reference herein in their entireties.

TECHNICAL FIELD

The present invention relates to a process for preparing a sulfonamide compound which is an inhibitor of Bcl-2/Bcl-xL, comprising a compound of formula (I) as described below, especially (3R)-1-(3-(4-(4-(4-(3-(2-(4-chlorophenyl)-1-isopropyl-4-methylsulfonyl-5-methyl-1H-pyrrol-3-yl)-5-fluorophenyl)piperazine-1-yl)-phenylaminosulfonyl)-2-trifluoromethanesulfonyl-anilino)-4-phenylthio-butyl)-piperidine-4-carboxylic acid 3-phosphonopropyl ester, and also relates to an intermediate for the preparation of the sulfonamide compound and a preparation process thereof.

BACKGROUND ART

Compound (3R)-1-(3-(4-(4-(4-(3-(2-(4-chlorophenyl)-1-isopropyl-4-methylsulfonyl-5-methyl-1H-pyrrol-3-yl)-5-fluorophenyl)piperazine-1-yl)-phenylaminosulfonyl)-2-trifluoromethanesulfonyl-anilino)-4-phenylthio-butyl)-piperidine-4-carboxylic acid 3-phosphonopropyl ester (hereinafter referred to as compound 1) is a sulfonamide drug which can be used as a Bcl-2/Bcl-xL inhibitor, and its structural formula is as follows

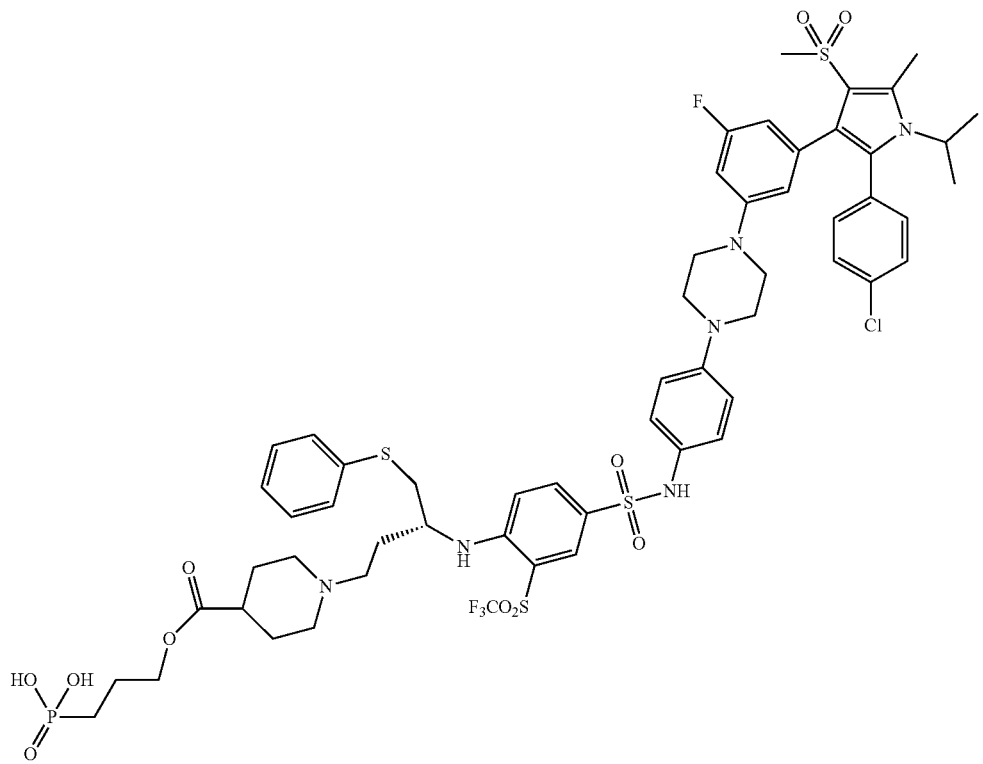

Compound 1 is a potential Bcl-2 and/or Bcl-xL inhibitor (see WO2014113413). This compound is effective in inducing apoptosis in cancer cells, has a mechanism of action that is highly consistent with targeting Bcl-2 and Bcl-xL, and can treat various cancers.

Patent WO2014113413 (hereinafter referred to as Patent 1) discloses a method for preparing compound 1, which involves three column chromatography purifications, one preparative liquid phase purification and lyophilization operation, has high cost, long period, low total yield, and limited batch production capacity, and is not suitable for commercial production. Therefore, there is an urgent need for a process for preparing the compound 1 suitable for amplification of industrialization to solve the technical problems existing in the prior art, which can reduce or eliminate column chromatography purification, reduce or eliminate liquid phase purification and lyophilization operations, reduce cost, shorten period, increase yield, and improve batch capacity.

SUMMARY OF INVENTION

It is an object of the present invention to provide a process for preparing sulfonamide compounds, including compounds of formula (I), in particular compound 1. The inventors have surprisingly discovered that two specific preparation processes (i.e. the process I and process II described below) can reduce or eliminate column chromatography purification, reduce or eliminate liquid phase purification and freeze-drying operation, reduce cost, shorten period, increase yield, and increase batch capacity.

Specifically, the first aspect of the invention relates to a process for preparing a compound of the following formula (I) or a pharmaceutically acceptable salt thereof (hereinafter referred to as process I),

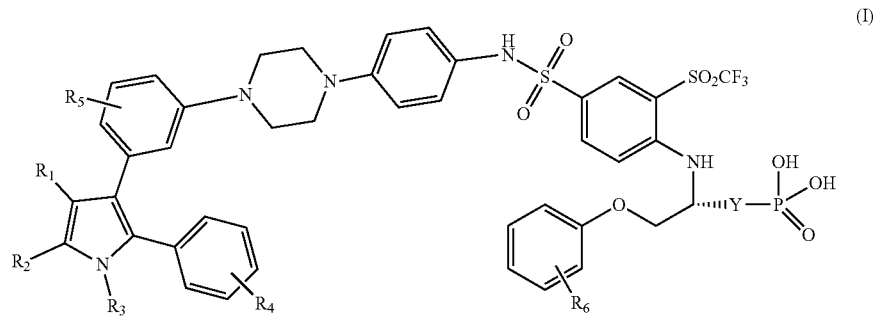

(I)

wherein, $R_1$ is $SO_2R'$, $R_2$ is an alkyl group, preferably $C_{1-4}$ alkyl, more preferably methyl, propyl, isopropyl, $R_3$ is an alkyl group, preferably $C_{1-4}$ alkyl, more preferably methyl, propyl, isopropyl, $R_4$ is halogen, preferably fluorine, chlorine, $R_5$ is halogen, preferably fluorine, chlorine, $R_6$ is selected from H, halogen, alkyl, preferably fluorine, chlorine, $C_{1-4}$ alkyl, more preferably H, methyl, propyl, isopropyl, most preferably H, Y is

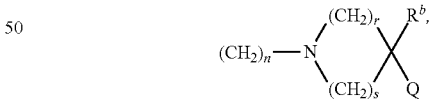

Q is $C(=O)O(C_{1-5}$ alkylene), preferably $C(=O)O(C_3$ alkylene), $R_b$ is hydrogen or an alkyl group, preferably $C_{1-4}$ alkyl, more preferably methyl, propyl, isopropyl, n, r and s are independently 1, 2, 3, 4, 5 or 6, preferably, both r and s are 2 and n is 3, 4 or 5, more preferably, n, r and s are all 2, R' is an alkyl group, preferably a $C_{1-4}$ alkyl group, more preferably methyl group, propyl group, isopropyl group;

the process comprises the following steps:

1) hydrolyzing a compound of formula 1 to form a compound of formula 2, formula 1
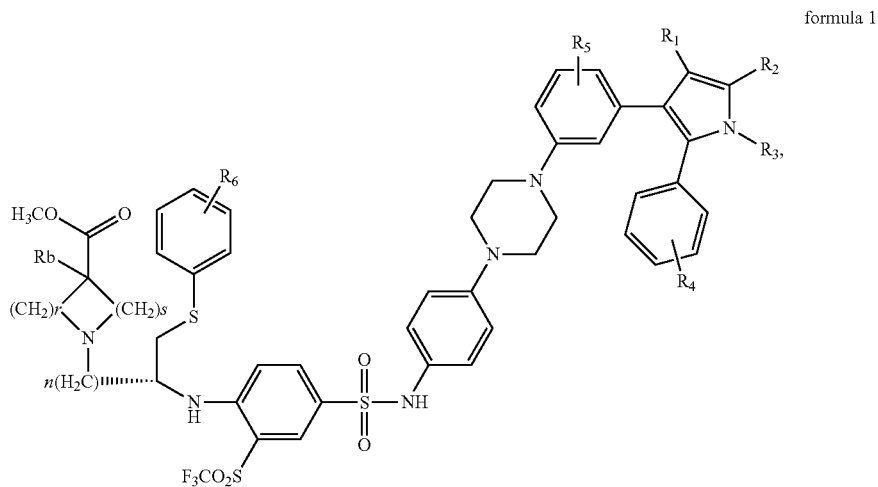
formula 2
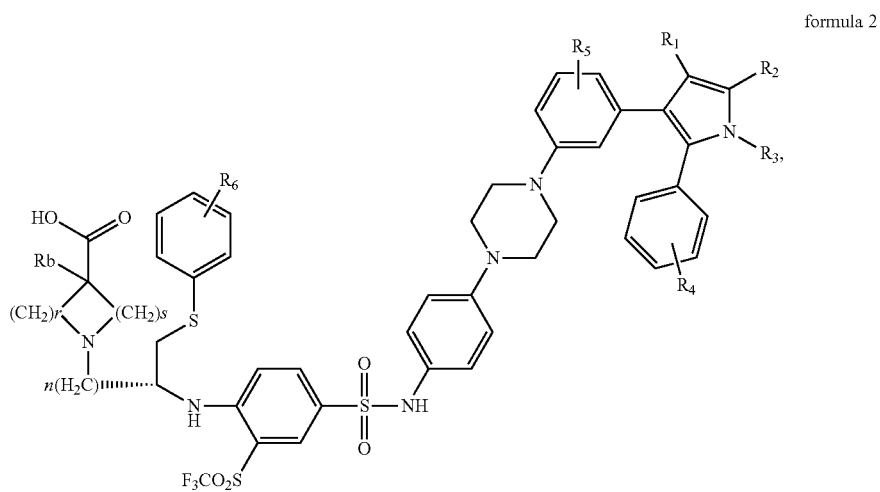
2) subjecting the compound of formula 2 to a condensation reaction with a compound of formula 3 to form a compound of formula 4,
formula 3
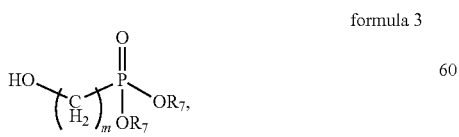
unless otherwise indicated, $R_7$ is an alkyl group, preferably $C_{1-4}$ alkyl, particularly preferably ethyl, m is 1, 2, 3, 4 or 5,

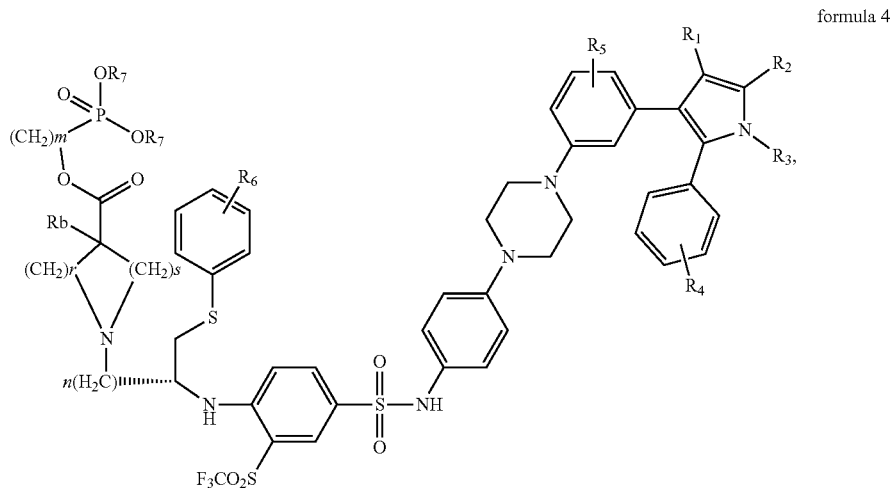

formula 4 unless otherwise indicated, $R_7$ is an alkyl group, preferably $C_{1-4}$ alkyl, particularly preferably ethyl, m is 1, 2, 3, 4 or 5, 3) forming a compound of formula 5 from the compound of formula 4

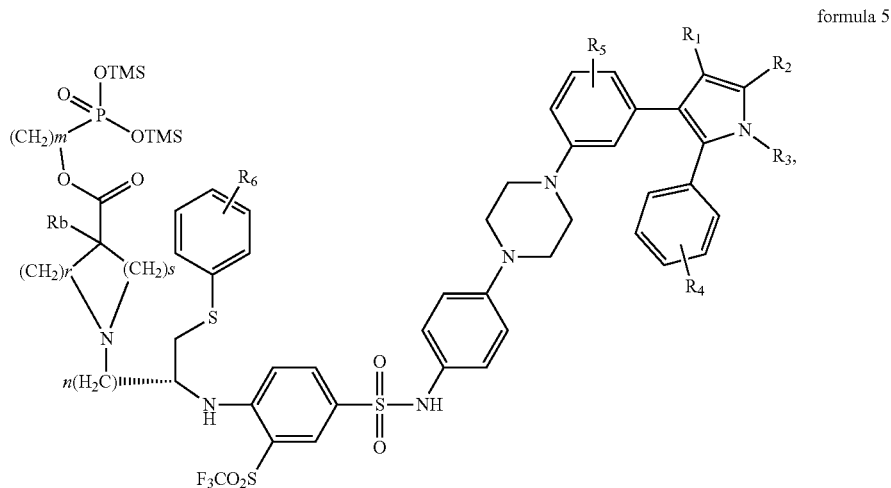

formula 5 wherein, TMS represents trimethylsilyl group, 4) forming a compound of formula (I) from the compound of formula 5.

Another aspect of the invention relates to a process for preparing a compound of the following formula (I) or a pharmaceutically acceptable salt thereof (hereinafter referred to as process II),

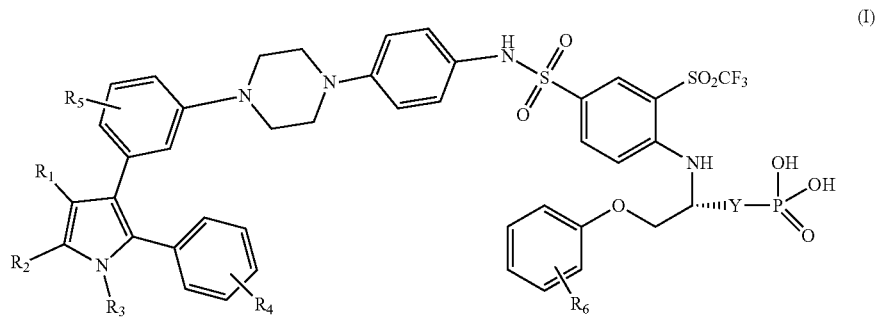

wherein, $R_1$ is $SO_2R'$, $R_2$ is an alkyl group, preferably $C_{1-4}$ alkyl, more preferably methyl, propyl, isopropyl, $R_3$ is an alkyl group, preferably $C_{1-4}$ alkyl, more preferably methyl, propyl, isopropyl, $R_4$ is halogen, preferably fluorine, chlorine, $R_5$ is halogen, preferably fluorine, chlorine, $R_6$ is selected from H, halogen, alkyl, preferably fluorine, chlorine, $C_{1-4}$ alkyl, more preferably H, methyl, propyl, isopropyl, most preferably H, Y is

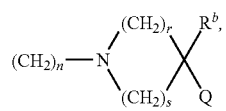

Q is $C(=O)O(C_{1-5}$ alkylene), preferably $C(=O)O(C_3$ alkylene), $R_b$ is hydrogen or an alkyl group, preferably $C_{1-4}$ alkyl, more preferably methyl, propyl, isopropyl, n, r and s are independently 1, 2, 3, 4, 5 or 6, preferably, both r and s are 2 and n is 3, 4 or 5, more preferably, n, r and s are all 2, R' is an alkyl group, preferably $C_{1-4}$ alkyl, more preferably methyl, propyl, isopropyl, the process comprises the following steps:

(1) reacting a compound of formula (1) with a compound of formula (2) to form a compound of formula (3),

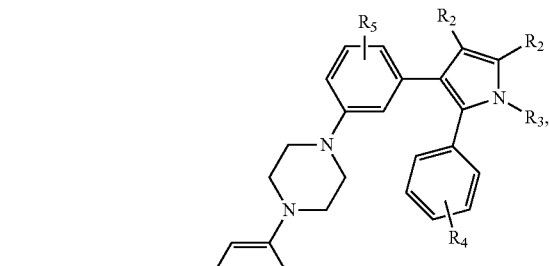

formula (1)

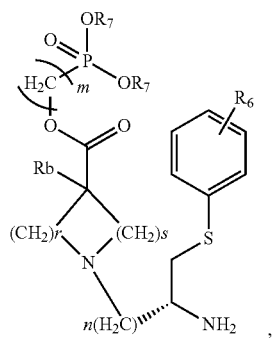

formula (2)

unless otherwise indicated, $R_7$ is an alkyl group, preferably $C_{1-4}$ alkyl, particularly preferably ethyl, m is 1, 2, 3, 4 or 5,

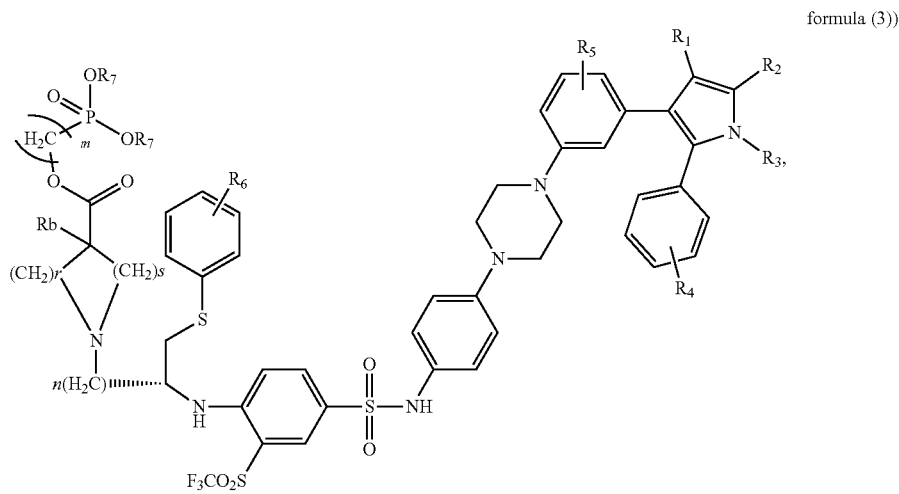

formula (3)

unless otherwise indicated, $R_7$ is an alkyl group, preferably $C_{1-4}$ alkyl, particularly preferably ethyl, (2) forming a compound of formula (4) from the compound of formula (3),

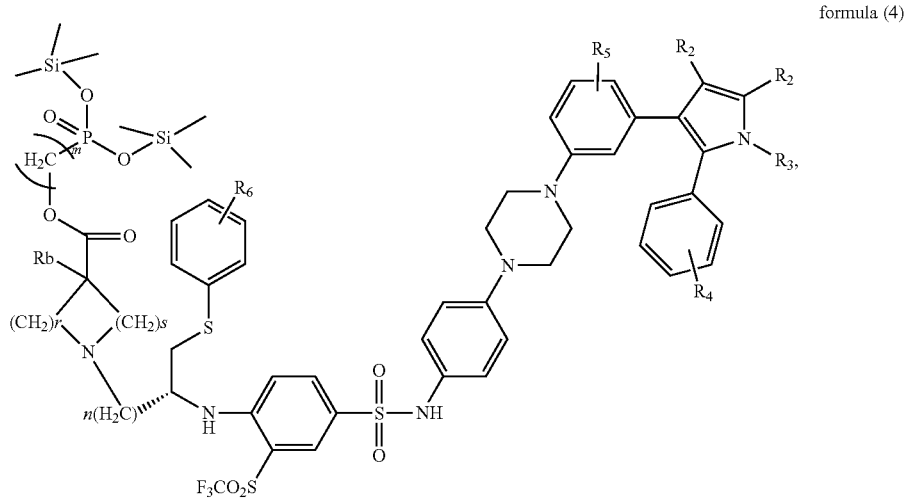

formula (4)

(3) forming a compound of formula (I) from the compound of formula (4).

Still another aspect of the present invention relates to an intermediate compound involved in the above preparation processes, a process for preparing the intermediate, and use of the intermediate compound for preparing a compound of formula (I).

Definition

The term "about" as used herein refers to ±20%, preferably ±15%, more preferably ±10%, even more preferably ±5%, and most preferably ±2% of the value modified by the term, so that one of ordinary skill in the art can clearly determine the scope of the term "about" according to the modified value.

iPr means isopropyl;
DCM means dichloromethane;
THE means tetrahydrofuran;
eq refers to the molar ratio;
M means the molar concentration;
IPC refers to monitoring during production;
TLC refers to thin layer chromatography;
DMF means dimethylformamide;
SM refers to starting material;
Raney-Ni means Raney nickel;
AcCl means acetyl chloride;
DIPEA means diisopropylethylamine;
Fmoc means fluorenylmethoxycarbonyl;
tBu means t-butyl;
Ph means phenyl;
ACN means acetonitrile;
TMS represents trimethylsilyl group;
TMSBr represents trimethylbromosilane;
EDCI means 1-ethyl-(3-dimethylaminopropyl)carbonyldiimide hydrochloride;
DCM means dichloromethane;
DMPAO means [(2,6-dimethylphenyl)amino](oxo)acetic acid
MeTHF means methyltetrahydrofuran;

PPTS means pyridinium p-toluenesulfonate;
Dean-stark refers to the Dean-Stark device (also known as Dean-Stark receiver or Dean-Stark distiller);
Red-Al means red aluminum;
MsCl means methylsulfonyl chloride;
TEA means triethylamine;
Xantphos means 4,5-bis(diphenylphosphino)-9,9-dimethylxanthene;
RT means room temperature;
DIBALH means diisobutylaluminum hydride;
MTBE means methyl tert-butyl ether;
DHP means 3,4-dihydro-2H-pyran;
TBDMSOTf means tert-butyldimethylsilyl triflate;
A good solvent refers to a solvent in which a substance is very soluble, and a poor solvent has the opposite properties as a good solvent.

DETAILED DESCRIPTION OF THE INVENTION

The first aspect of the invention relates to a process for preparing a compound of the following Formula (I) or a pharmaceutically acceptable salt thereof (hereinafter referred to as process I),

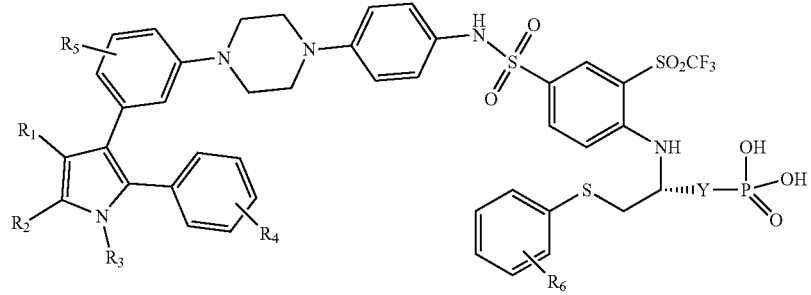

wherein,
$R_1$ is $SO_2R'$,
$R_2$ is an alkyl group, preferably $C_{1-4}$ alkyl, more preferably methyl, propyl, isopropyl,
$R_3$ is an alkyl group, preferably $C_{1-4}$ alkyl, more preferably methyl, propyl, isopropyl,
$R_4$ is halogen, preferably fluorine, chlorine,
$R_5$ is halogen, preferably fluorine, chlorine,
$R_6$ is selected from H, halogen, alkyl, preferably fluorine, chlorine, $C_{1-4}$ alkyl, more preferably methyl, propyl, isopropyl,
Y is

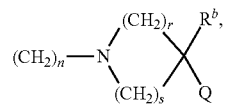

Q is $C(=O)O(C_{1-5}$ alkylene), preferably $C(=O)O(C_3$ alkylene),
$R_b$ is hydrogen or an alkyl group, preferably $C_{1-4}$ alkyl, more preferably methyl, propyl, isopropyl,
n, r and s are independently 1, 2, 3, 4, 5 or 6, preferably, both r and s are 2 and n is 3, 4 or 5, more preferably, n, r and s are all 2,
R' is an alkyl group, preferably $C_{1-4}$ alkyl, more preferably methyl, propyl, isopropyl,
the process comprises the following steps:
1) hydrolyzing a compound of formula 1 to form a compound of formula 2, formula 1
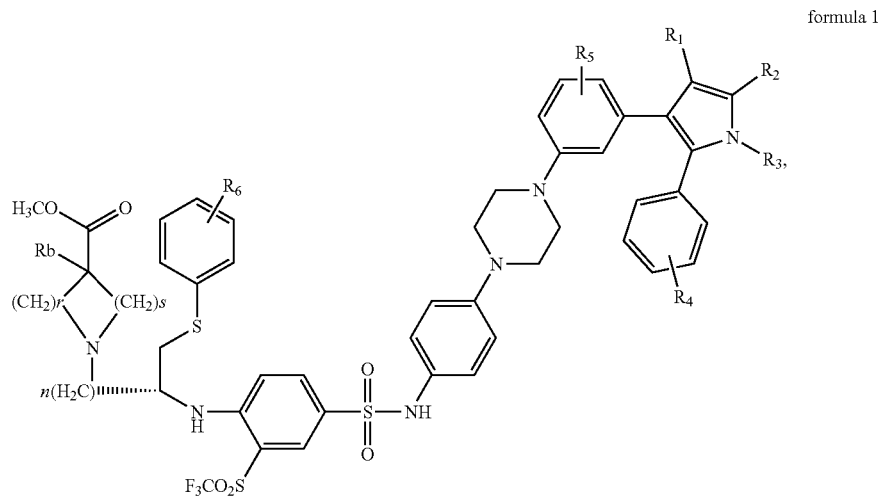
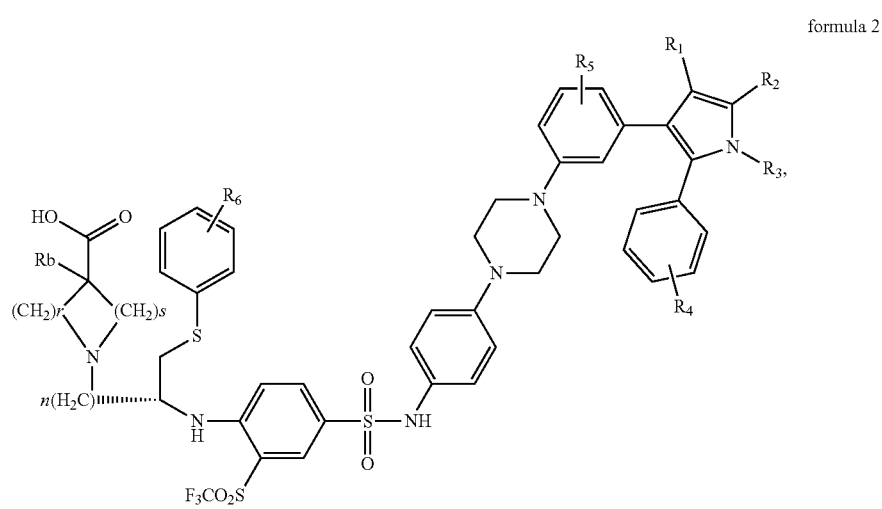
formula 2
2) subjecting the compound of formula 2 to a condensation reaction with a compound of formula 3 to form a compound of formula 4,
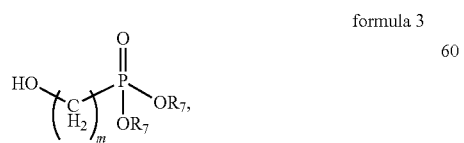
formula 3
wherein $R_7$ is an alkyl group, preferably $C_{1-4}$ alkyl, particularly preferably ethyl, and m is 1, 2, 3, 4 or 5,

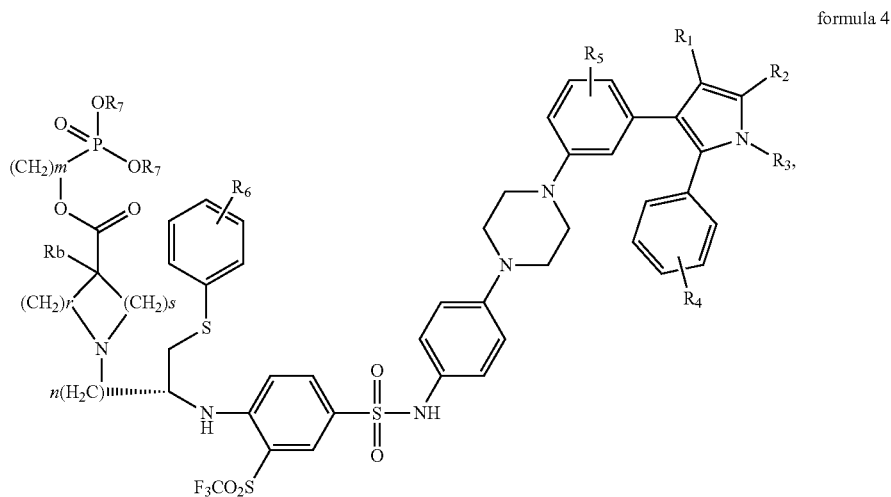

formula 4 unless otherwise indicated, $R_7$ is an alkyl group, preferably $C_{1-4}$ alkyl, particularly preferably ethyl, m is 1, 2, 3, 4 or 5, 3) forming a compound of formula 5 from the compound of formula 4

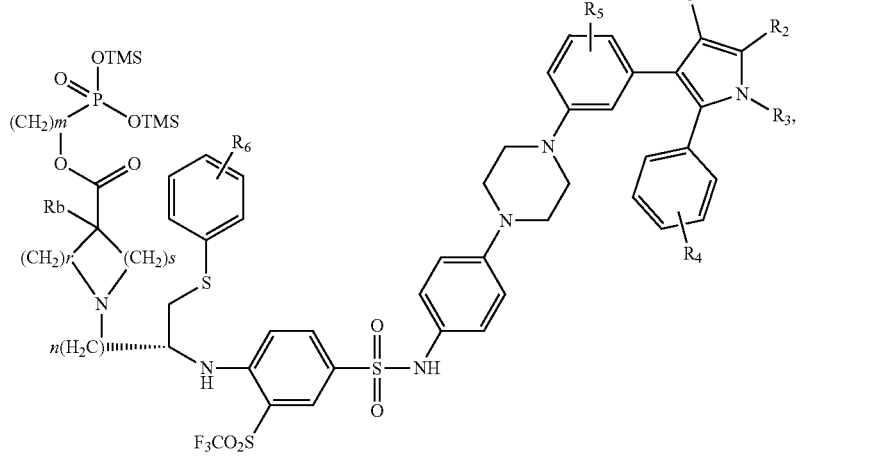

formula 5

4) forming a compound of formula (I) from the compound of formula 5.

In some embodiments, step 1) is carried out in the presence of a base in a solvent, and preferably, the base is a hydroxide, preferably sodium hydroxide, and the solvent is a polar solvent, preferably water and tetrahydrofuran.

In some embodiments, step 2) is carried out in the presence of a condensing agent, preferably 1-ethyl-(3-dimethylaminopropyl) carbonyldiimide hydrochloride (EDCI), and a catalyst, preferably 4-dimethylaminopyridine (DMAP), in a polar organic solvent, more preferably dichloromethane.

In some embodiments, step 3) is carried out in the presence of a trialkylbromosilane, preferably trimethylbromosilane or triethylbromosilane, more preferably trimethylbromosilane (TMSBr) in a polar solvent, preferably acetonitrile (ACN).

In some embodiments, step 4) is carried out in a polar solvent, preferably water and acetonitrile (ACN), more preferably in water and acetonitrile in a volume ratio v/v=1/6 to 1/2.

In some embodiments, step 4) is carried out in the presence of bicarbonate salt and an acid, preferably ammonium hydrogen carbonate and trifluoroacetic acid and/or phosphoric acid.

Compared with dicyclohexylcarbodiimide (DCC) and diisopropylcarbodiimide (DIC), the by-products produced by the EDCI used in the step 2) of the process I of the present invention are easily removed, which is advantageous for the yield improvement.

The diethyl phosphonate used in the step 2) of the process I of the present invention may be a commercially available product, and a commercially available product of diethyl phosphonate is cheaper and more readily available than a commercially available product of dimethyl phosphonate, which can reduce production costs greatly.

The ACN used in the step 3) of the process I of the invention can make the reaction carried out at a higher temperature (60° C.), which can effectively shorten the reaction time and reduce the risk of impurity formation.

In some embodiments, the preparation of the compound of formula 1 comprises the following steps:

1') reacting a compound of formula 1' with a compound of formula 2' to form a compound of formula 3',

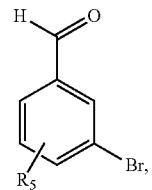
formula 1'

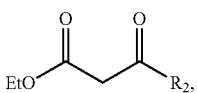
formula 2'

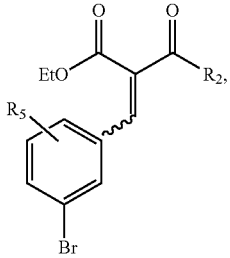
formula 3'

2') reacting the compound of formula 3' with a compound of formula 4' to form a compound of formula 5',

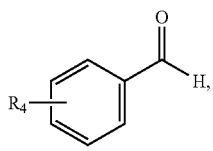
formula 4'

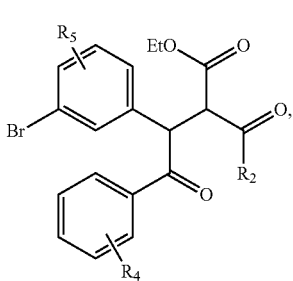
formula 5'

3') reacting the compound of formula 5' with a compound of formula 6' to form a compound of formula 7',

formula 6'

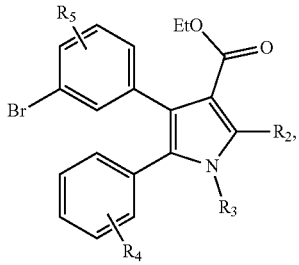
formula 7'

4') forming a compound of formula 8' from the compound of formula 7',

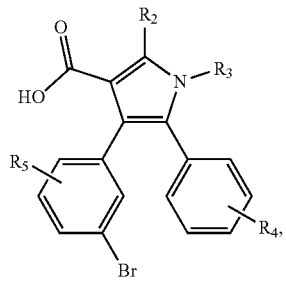
formula 8'

5') forming a compound of formula 9' from the compound of formula 8'

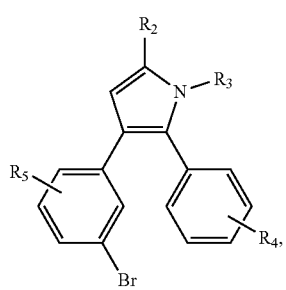
formula 9'

6') forming a compound of formula 10' from the compound of formula 9'

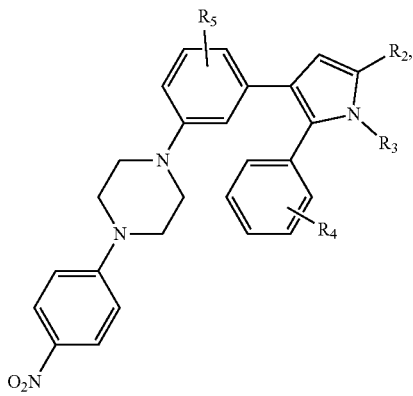

formula 10'

7') forming a compound of formula 11' from the compound of formula 10',

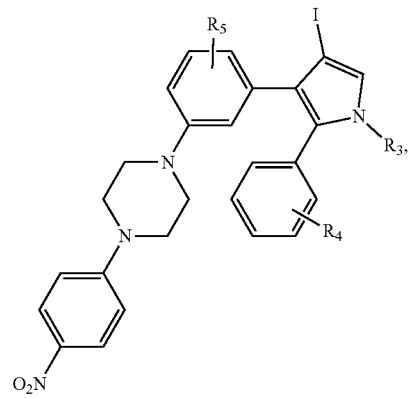

formula 11'

8') reacting the compound of formula 11' with a compound of formula 12' to form a compound of formula 13',

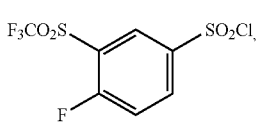

formula 12'

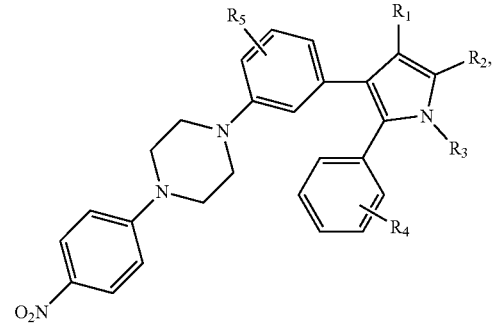

formula 13'

9') forming a compound of formula 14' from the compound of formula 13',

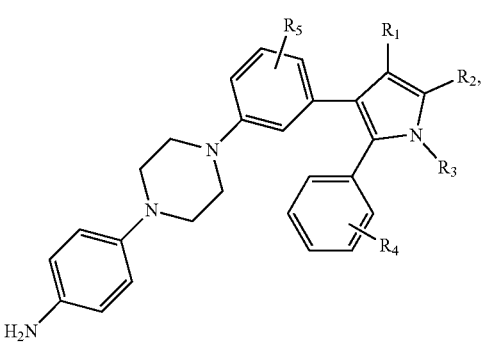

formula 14'

10') reacting the compound of formula 14' with a compound of formula 15' to form a compound of formula 16', formula 15' formula 16'

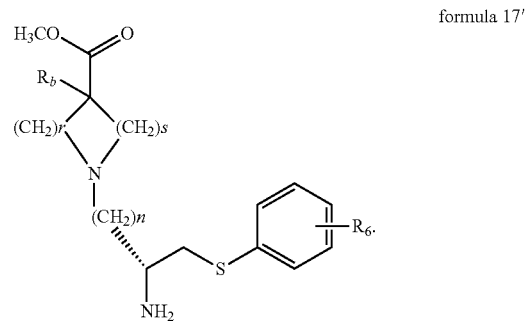

11') reacting the compound of formula 16' with a compound of formula 17' to form a compound of formula 1, formula 17'

In some embodiments, step 1') is carried out in an organic solvent, preferably toluene, in the presence of a base, preferably an organic base, more preferably piperidine, or in the presence of an organic acid, preferably a monobasic organic acid containing from 1 to 4 carbons, more preferably acetic acid.

In some embodiments, step 2') is carried out in the presence of a catalyst, for example

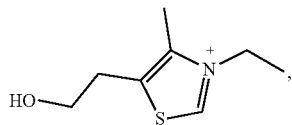

and a basic condition, for example an organic base such as an amine, for example a trialkylamine, for example a tri$C_{1-4}$ alkylamine, preferably triethylamine.

In some embodiments, step 3') is carried out in the presence of an organic acid, preferably a monobasic organic acid containing 1 to 4 carbons, more preferably acetic acid, or in the presence of an organic base, preferably an alkylamine, more preferably a $C_{1-4}$ alkylamine, in an organic solvent, preferably an alcohol, more preferably a $C_{1-4}$ alcohol.

In some embodiments, step 4') is carried out in the presence of a base, preferably a hydroxide, more preferably sodium hydroxide, and/or in a polar solvent, preferably dioxane and/or ethanol and/or water.

In some embodiments, step 5') is carried out in the presence of an organic acid, preferably trifluoroacetic acid, in a polar organic solvent, more preferably dichloromethane.

In some embodiments, in step 6'), the compound formula 9' is reacted with

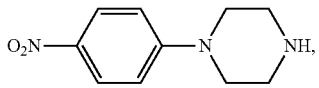 [SMILES: O=[N+]([O-])c1ccc(N2CCNCC2)cc1]

preferably, the reaction is carried out in the presence of a coupling ligand, preferably proline or

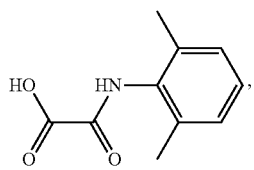

and/or in the presence of cuprous iodide and/or potassium carbonate;

In some embodiments, step 6') is carried out at 120±5° C.

In the above process of the present invention, in step 6'), a compound of formula 10' is formed from a compound of formula 9', the reaction temperature and the coupled ligand used therein can effectively control the formation of dechlorination by-products while increasing the conversion rate of the reaction. Specifically, using DMPAO as a coupling ligand increase the yield by 15% to 20%.

In some embodiments, step 7') is carried out in the presence of N-iodosuccinimide in an organic solvent, preferably dimethylformamide.

In some embodiments, step 8') is carried out in the presence of a metal iodide, preferably cuprous iodide L-proline, in an organic solvent, preferably dimethyl sulfoxide, under basic conditions, preferably a hydroxide, more preferably a metal hydroxide, further preferably sodium hydroxide;

In some embodiments, step 8') is carried out at 100±5° C.

In the above process of the present invention, the reaction temperature employed in step 8') increases the conversion rate of the reaction and controls the formation of dechlorination by-products.

In some embodiments, step 9') is carried out in the presence of hydrogen, a catalyst, preferably Raney nickel or palladium on carbon in an organic solvent, preferably a polar organic solvent, more preferably methanol or tetrahydrofuran.

In some embodiments, step 10') is carried out in an organic solvent, preferably a polar organic solvent, more preferably tetrahydrofuran or methanol, or a polar solvent, preferably dichloromethane, in the presence of a basic condition, preferably an organic base, further preferably pyridine.

In some embodiments, step 11') is carried out in the presence of basic conditions, preferably an organic base, further preferably diisopropylethylamine, and/or in a polar solvent organic solvent, preferably dichloromethane or DMF.

In some embodiments, the preparation of the compound of formula 17' comprises the following steps:

1") forming a compound of formula 2" from a compound of formula 1"

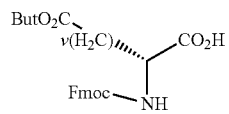

v=n−1, n is defined as above

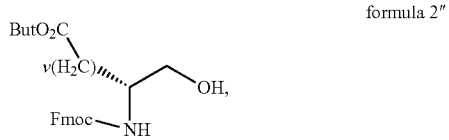

2") forming a compound of formula 3" from the compound of formula 2",

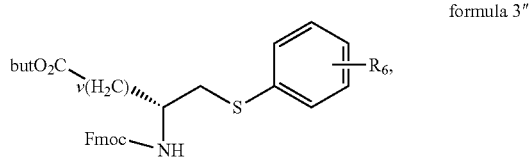

3") forming a compound of formula 4" from the compound of formula 3",

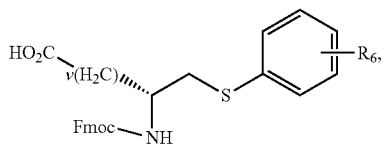

formula 4"

4") forming a compound of formula 5" from the compound of formula 4"

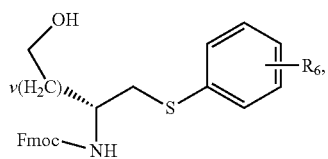

formula 5"

5") forming a compound of formula 6" from the compound of formula 5",

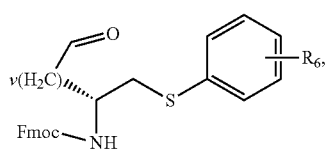

formula 6"

6") reacting the compound of formula 6" with a compound of formula 7" to form a compound of formula 8",

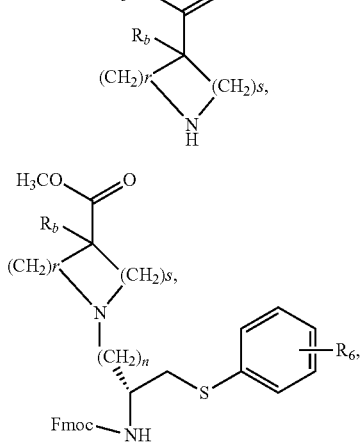

formula 7"

formula 8"

7") forming a compound of formula 17' from the compound of formula 8".

In some embodiments, step 1") comprises the following steps:

(a) the compound of formula 1" is reacted in the presence of isobutyl chloroformate, N-methylmorpholine, and/or in ethylene glycol dimethyl ether, (b) further reacted with aqueous solution of sodium borohydride.

In some embodiments, step 2") is carried out in the presence of diphenyl disulfide, a trialkylphosphine, preferably a triC1-4 alkylphosphine, more preferably tributylphosphine, in a polar organic solvent, more preferably dichloromethane.

In some embodiments, step 3") is carried out in the presence of an organic acid, preferably trifluoroacetic acid, in a polar organic solvent, more preferably dichloromethane.

In some embodiments, step 4") comprises the following steps:

(a) the compound of formula 4" is reacted in the presence of isobutyl chloroformate, N-methylmorpholine, and/or in ethylene glycol dimethyl ether, (b) further is reacted with an aqueous solution of sodium borohydride. In some embodiments, step 5") is carried out in the presence of oxalyl chloride, dimethyl sulfoxide, diisopropylethylamine, and/or in dichloromethane.

In some embodiments, step 6") is carried out in the presence of sodium triacetoxyborohydride in a polar organic solvent, more preferably dichloromethane.

In some embodiments, step 7") is carried out in the presence of diethylamine and/or in a polar solvent, preferably acetonitrile.

In some embodiments, the compound of formula 15' is either commercially available or prepared according to processes known in the art.

In some embodiments, the preparation of the compound of formula 3 comprises the following steps:

1''') forming a compound of formula 3 from a compound of formula 1''',

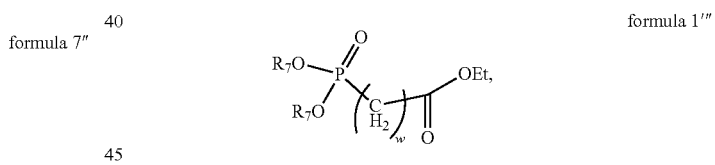

formula 1''' unless otherwise defined, $R_7$ herein is alkyl, preferably $C_{1-4}$ alkyl, particularly preferably ethyl, w=1, 2, 3, 4 or 5.

In some embodiments, step 1''') is carried out in a polar organic solvent, more preferably dichloromethane, in the presence of a catalyst, preferably lithium borohydride.

In some embodiments, the preparation of the compound of formula 3 comprises the following steps:

1'''') forming a compound of formula 2'''' from a compound of formula 1'''', wherein, m is 1, 2, 3, 4 or 5,

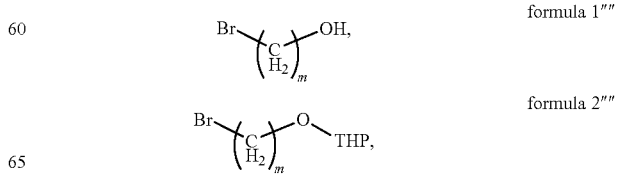

formula 1'''' formula 2''''

2"") forming a compound of formula 3"" from the compound of formula 2"",

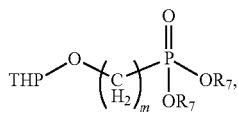

formula 3""

3"") forming a compound of formula 3 from the compound of formula 3"".

In some embodiments, step 1"") is carried out in the presence of a catalyst, such as PPTS, in the presence of DHP, in an organic solvent such as dichloromethane or MTBE.

In some embodiments, in step 2""), the compound of formula 2"" is reacted with P(OEt)$_3$ or PO(OEt)$_2$ to form a compound of the formula 3"".

In some embodiments, step 3"") is carried out in the presence of an ion exchange resin, preferably Amberlite, more preferably Amberlite (10%), in an organic solvent, such as a polar organic solvent, such as a $C_{1-4}$ alcohol, and/or in the presence of PPTS and/or TFA, and/or in the presence of Dowex (preferably 10%), and/or in the presence of Ambrlyst-15 (preferably 10%).

The foregoing embodiments may be optionally combined.

Another aspect of the invention relates to a process for preparing a compound of the following Formula (I) or a pharmaceutically acceptable salt thereof (hereinafter referred to as process II),

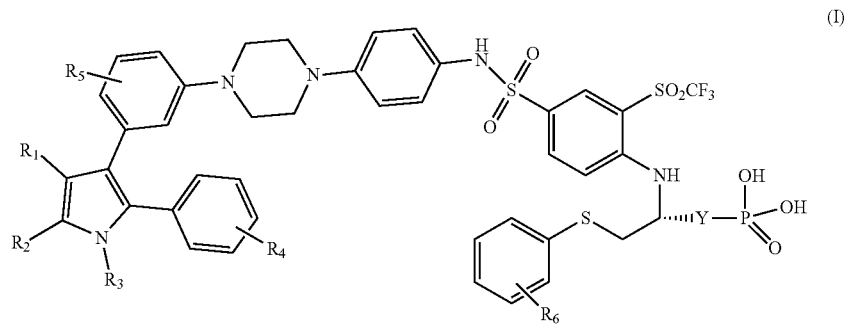

(I)

wherein, $R_1$ is $SO_2R'$, $R_2$ is an alkyl group, preferably $C_{1-4}$ alkyl, more preferably methyl, propyl, isopropyl, $R_3$ is an alkyl group, preferably $C_{1-4}$ alkyl, more preferably methyl, propyl, isopropyl, $R_4$ is halogen, preferably fluorine, chlorine, $R_5$ is halogen, preferably fluorine, chlorine, $R_6$ is selected from H, halogen, alkyl, preferably fluorine, chlorine, $C_{1-4}$ alkyl, more preferably H, methyl, propyl, isopropyl, most preferably H, Y is

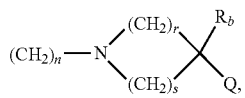

Q is C(=O)O($C_{1-5}$ alkylene), preferably C(=O)O($C_3$ alkylene), $R_b$ is hydrogen or an alkyl group, preferably $C_{1-4}$ alkyl, more preferably methyl, propyl, isopropyl, n, r and s are independently 1, 2, 3, 4, 5 or 6, preferably, both r and s are 2 and n is 3, 4 or 5, more preferably, n, r and s are all 2, R' is an alkyl group, preferably $C_{1-4}$ alkyl, more preferably methyl, propyl, isopropyl, the process comprises the following steps:

(1) reacting a compound of formula (1) with a compound of formula (2) to form a compound of formula (3)

formula (1)

-continued

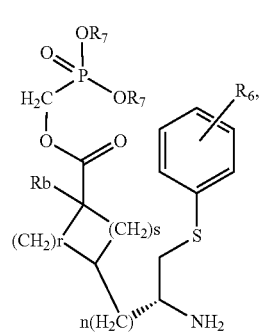

formula (2)

unless otherwise defined, $R_7$ herein is an alkyl group, preferably $C_{1-4}$ alkyl, particularly preferably ethyl, m is 1, 2, 3, 4 or 5,

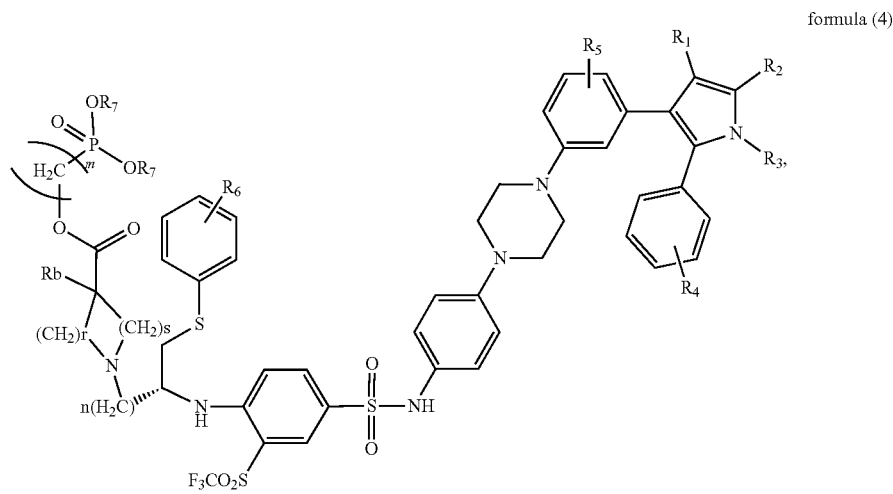

formula (4)

unless otherwise defined, $R_7$ herein is an alkyl group, preferably $C_{1-4}$ alkyl, particularly preferably ethyl, m is 1, 2, 3, 4 or 5, (2) forming a compound of formula (4) from the compound of formula (3),

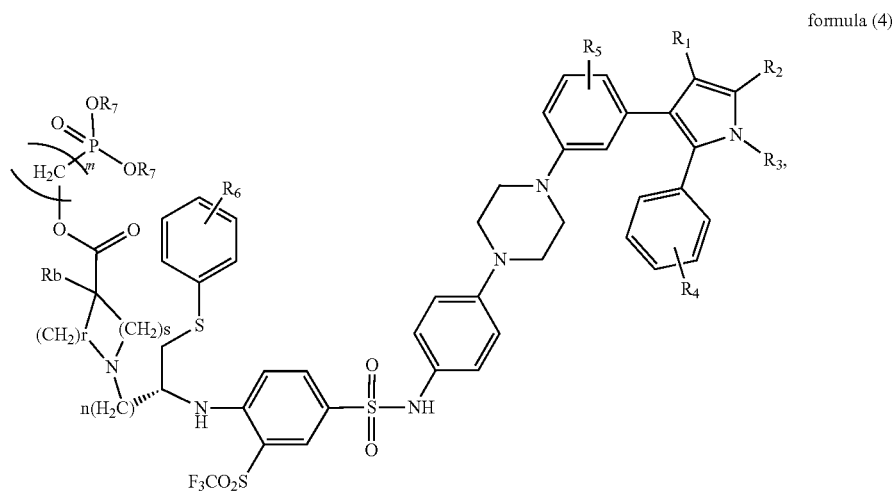

formula (4)

(3) forming a compound of formula (I) from the compound of formula (4).

wherein, unless otherwise defined, the groups and variables defined in the above formulas (1) to (3) having the same meaning as those defined above for the corresponding groups of the compounds of the formula (I).

In some embodiments, step (1) is carried out in the presence of basic conditions, preferably an organic base, further preferably diisopropylethylamine, and/or in a polar solvent, preferably DMF, ethyl acetate or dichloromethane (DCM).

In the process II of the present invention, the step (1) avoids the side reaction of the formula (3) and the compound of formula 2 in the process I, achieves high conversion rate, and effectively controls the formation of impurities; and at the same time, hydrolysis step of the compound of formula 2 in the process I is omitted to avoid the formation of by-products from sulfonate hydrolysis in this step.

In some embodiments, step (2) is carried out in the presence of a trialkylbromosilane, preferably trimethylbromosilane or triethylbromosilane (more preferably trimethylbromosilane), and/or in acetonitrile; the amount of the trialkyl bromosilane is preferably 20 equivalents to 5 equivalents, more preferably 15 equivalents to 5 equivalents based on the compound of formula (3).

In some embodiments, step (3) comprises the following steps:

a) reacting a compound of formula (2) with ammonium bicarbonate, aqueous ammonia or an ammonia-alcohol solution (preferably an ammonia-$C_{1-4}$ alcohol solution, more preferably an ammonia-methanol solution) in a polar organic solvent, more preferably acetonitrile or dichloromethane, to get the crude product 1.

b) treating the crude product 1 with an extraction system comprising a polar organic solvent and an aqueous solution of a salt, the polar organic solvent is preferably methyltetrahydrofuran or dichloromethane, the aqueous solution of a salt is such as an aqueous solution of a carbonate salt, preferably an aqueous solution of ammonium hydrogen carbonate, more preferably 5% aqueous solution of ammonium hydrogen carbonate, preferably washing the crude product with the aqueous solution of a salt to obtain a crude product 2.

c) treating the crude product 2 with a good organic solvent, preferably a methylene chloride and/or methyltetrahydrofuran (more preferably 2-methyltetrahydrofuran), and a poor organic solvent, preferably an ether, more preferably isopropyl ether and/or methyl tert-butyl ether.

In some embodiments, the preparation of the compound of formula (1) comprises the following steps:

(1') forming a compound of formula (2') from a compound of formula (1'),

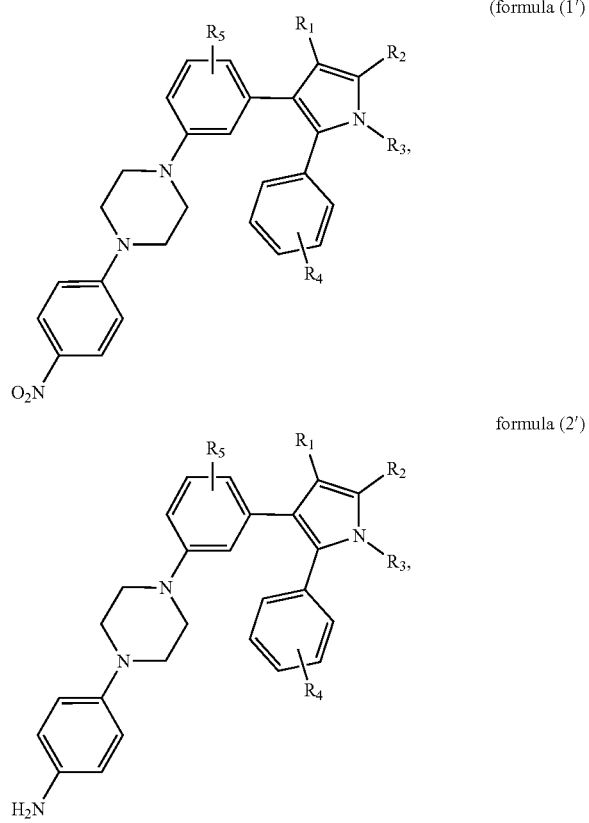

(2') forming a compound of formula (1) from the compound of formula (2').

In some embodiments, in the step (1'), the compound of formula (1') is reacted with a metal, further preferably a metal powder, more preferably an iron powder, in a polar organic solvent, more preferably ethanol.

In some embodiments, in the step (2'), the compound of formula (2') is reacted with the compound of formula 15' in the presence of basic conditions, preferably an organic base, further preferably triethylamine, diisopropylethylamine, pyridine, pyridine hydrochloride or triethylamine hydrochloride, more preferably, triethylamine hydrochloride, in an organic solvent, preferably tetrahydrofuran, toluene and dichloromethane, more preferably dichloromethane, at a temperature ranging from room temperature to the reflux temperature of the solvent.

In some embodiments, in the step (2'), the compound of formula 15' is used in an amount of from 2.0 to 1.5 equivalents based on the compound of formula (2'), and the base is used in an amount of from 1.5 to 5 equivalents based on the compound of formula (2').

In some embodiments, in the step (2'), the compound of formula (2') is added to a polar organic solvent, more preferably dichloromethane, and then triethylamine hydrochloride is added, and the solution of the compound of formula 15' in a polar organic solvent, more preferably dichloromethane is dropped into the reaction system which is heated and refluxed for reaction.

In some embodiments, in step (2'), the organic phase is preferably washed successively with aqueous HCl (preferably 1 N HCl), H$_2$O, sodium chloride solution (preferably 10% sodium chloride solution), and/or filtered, and/or concentrated to obtain the crude product; and/or the crude product is treated with a crystalline good solvent comprising a polar organic solvent, preferably ethyl acetate, dichloromethane, tetrahydrofuran, methanol or ethanol, and a crystalline poor solvent comprising heptane, n-heptane, methyl tert-butyl ether or water.

In some embodiments, the preparation of the compound of formula (1') comprises the following steps:

(1") forming a compound of formula (2") from a compound of formula (1"),

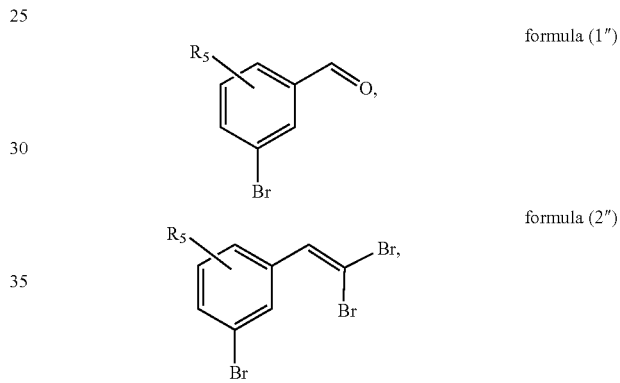

(2") forming a compound of formula (3") from the compound of formula (2"),

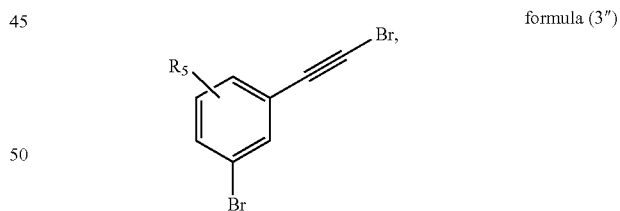

(3") forming a compound of formula (4") from the compound of formula (3"),

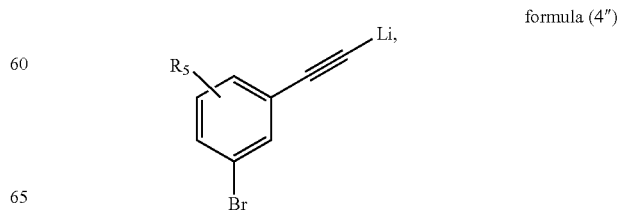

(4") forming a compound of formula (5") from the compound of formula (4"),

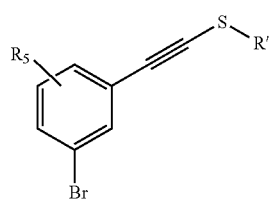

formula (5")

(5") forming a compound of formula (6") from the compound of formula (5"),

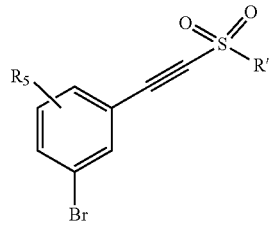

formula (6")

(6") reacting the compound of formula (6") with a compound of formula (7") to form a compound of formula (8"),

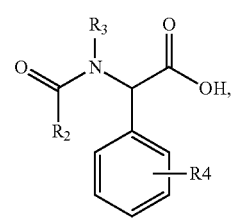

formula (7")

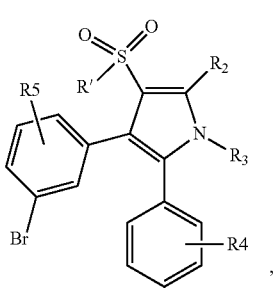

formula (8")

(7") forming a compound of formula (9") from the compound of formula (8"),

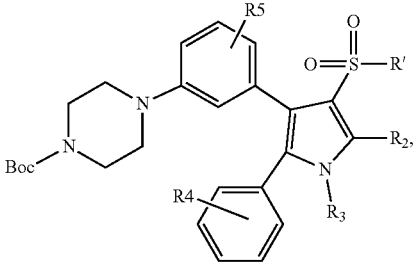

formula (9")

(8") forming a compound of formula (10") from the compound of formula (9"),

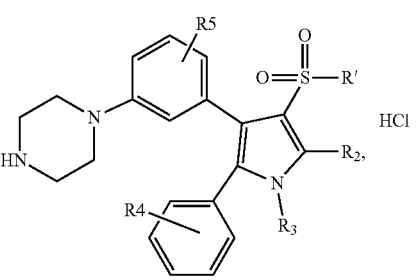

formula (10")

(9") forming a compound of formula (1') from the compound of formula (10").

In some embodiments, step (1") is carried out in the presence of $CBr_4/PPh_3$ in a polar organic solvent, more preferably dichloromethane, and/or at 0-30° C.

In some embodiments, step (2") is carried out in the presence of lithium diisopropylamide (LDA) at −85 to −70° C., in a solvent, preferably a polar solvent, more preferably tetrahydrofuran.

In some embodiments, step (3") is carried out in the presence of a lithium reagent, preferably LDA, at −85 to −70° C., in a solvent, preferably a polar solvent, more preferably tetrahydrofuran.

In some embodiments, step (4") is carried out in the presence of dimethyl disulfide (MeSSMe), in a solvent, preferably a polar solvent, more preferably tetrahydrofuran.

In some embodiments, step (2") to step (4") are carried out in a one-pot process.

In some embodiments, step (5") is carried out in the presence of an oxidizing agent, preferably metachloroperbenzoic acid (mCPBA), at 0 to 30° C., in a polar organic solvent, more preferably dichloromethane.

In some embodiments, step (6") is carried out in acetic anhydride, and at a temperature of 100 to 110° C.

In some embodiments, in the step (7"), the compound of formula (8") is reacted with the compound of formula (11"),

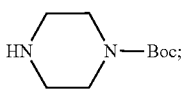

formula (11")

Preferably, the phosphine ligand and the palladium catalyst, preferably R—(+)-1,1'-binaphthyl-2,2'-diphenylphosphine (R-BINAP) and Pd(OAc)$_2$, are added to the organic solvent, preferably toluene, and then the mixture is preferably heated to 40-60° C. under stirring; a compound of formula (8"), a compound of formula (11"), water, and sodium t-butoxide are sequentially added; after the addition, the mixture is warmed to 100 to 110° C., and/refluxed for reaction.

In some embodiments, step (8") is carried out in the presence of an acid, preferably CH$_3$COCl, in a solvent, preferably a polar solvent, preferably ethanol, and preferably, a compound of formula (9") is added to a mixed solution of dichloromethane and absolute ethanol.

In some embodiments, in the step (9"), a compound of formula (10") is reacted with a compound of formula (12")

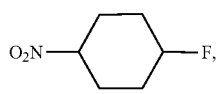

formula (12")

and preferably, the reaction is carried out at a temperature of 55 to 65° C. under alkaline conditions, preferably in the presence of potassium carbonate, in a polar solvent, preferably dimethyl sulfoxide.

In some embodiments, the preparation of the compound of formula (7") comprises the following steps:

(1''') forming a compound of formula (2''') from a compound of formula (1'''),

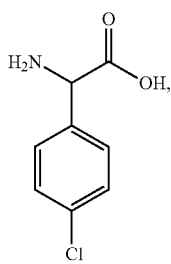

formula (1''')

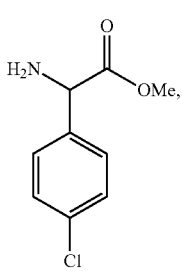

formula (2''')

(2''') forming a compound of formula (3''') from the compound of formula-(2'''),

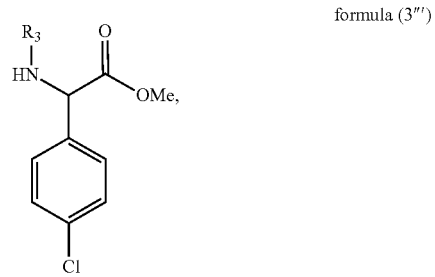

formula (3''')

(3''') forming a compound of formula (7") from the compound of formula (3''').

In some embodiments, step (1''') is carried out in the presence of SOCl$_2$ in a solvent, preferably a polar solvent, preferably methanol.

In some embodiments, step (2''') is carried out in the presence of NaBH(OAc)$_3$ in a solvent, preferably acetone/dichloromethane.

In some embodiments, step (3''') is carried out in the presence of AcCl, DIPEA/DMA.

In some embodiments, step (4''') is carried out in the presence of a base, preferably LiOH, in a solvent, preferably a polar solvent, preferably water and tetrahydrofuran.

In some embodiments, the preparation of the compound of formula (2) comprises the following steps:

(1'''') forming a compound of formula (2'''') from a compound of formula (1''''),

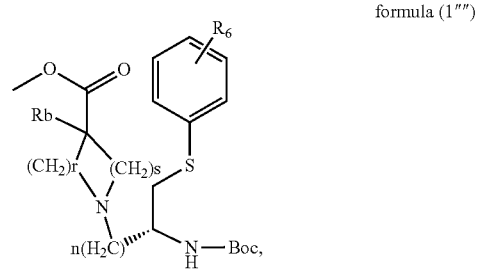

formula (1'''')

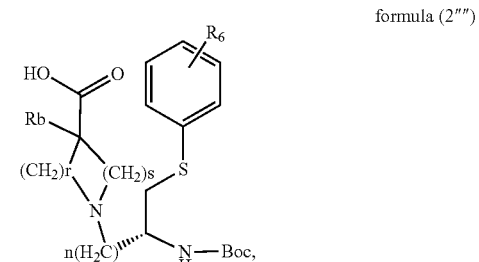

formula (2'''')

(2'''') reacting the compound of formula (2'''') with a compound of formula (3'''') to form a compound of formula (4''''),

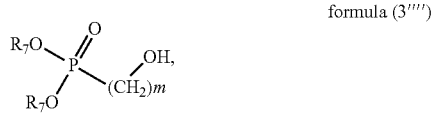

formula (3'''')

-continued

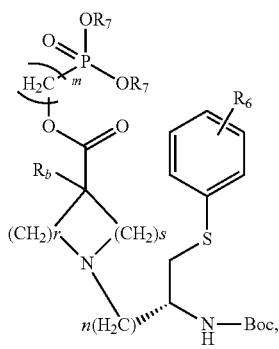

formula (4'''')

(3'''') forming a compound of formula (2) from the compound of formula (4'''').

In some embodiments, step (1'''') is carried out in the presence of a base, preferably a hydroxide, more preferably sodium hydroxide, in a solvent, preferably a polar solvent, more preferably water and tetrahydrofuran.

In some embodiments, step (2'''') is carried out in a polar organic solvent, more preferably dichloromethane, in the presence of a condensing agent, preferably EDCI and a catalyst, preferably DMAP.

In some embodiments, step (3'''') is carried out in the presence of acidic conditions and/or tert-butyldimethylsilyl trifluoromethanesulfonate (TBDMSOTf), in a polar organic solvent, more preferably dichloromethane, and preferably, the amount of TBDMSOTf is 1-6 eq, more preferably 1 to 3 eq, relative to formula (4'''').

In some embodiments, in the step (3''''), after the reaction is stopped, and the reaction system is extracted with $H_2O$. The aqueous phase is combined, and the pH of the aqueous phase is adjusted to pH ~8 with saturated $NaHCO_3$; and/or the aqueous phase is extracted with DCM.

In the step (3'''') of the process II of the present invention, the de-Boc reagent and the post-treatment process are adopted to ensure that the ester group is not affected when the Boc is removed, and the by-product introduced by the de-Boc reagent can be effectively removed.

In some embodiments, the preparation of the compound of formula (1'''') comprises the following steps:

(1''''') forming a compound of formula (2''''') from a compound of formula (1''''')

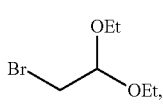

formula (1''''')

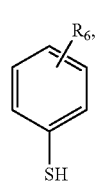

formula (2''''')

(2''''') forming a compound of formula (3''''') from the compound of formula (2''''')

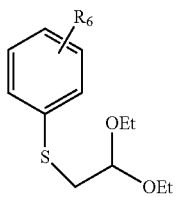

formula (3''''')

(3''''') reacting the compound of formula (3''''') with a compound of formula (4''''') to form a compound of formula (5''''''),

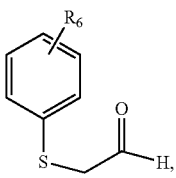

formula (4''''')

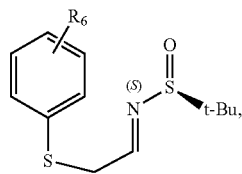

formula (5''''')

(4''''') forming a compound of formula (6''''') from the compound of formula (5''''')

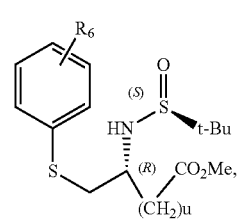

formula (6''''')

(5''''') forming a compound of formula (7''''') from the compound of formula (6''''')

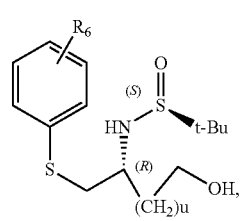

formula (7''''')

(6'''') forming a compound of formula (8'''') from the compound of formula (7'''')

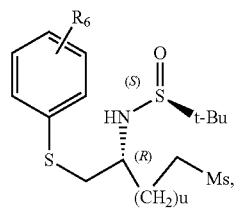

formula (8'''')

(7'''') reacting the compound of formula (8'''') with a compound of formula (9'''') to form a compound of formula (10'''')

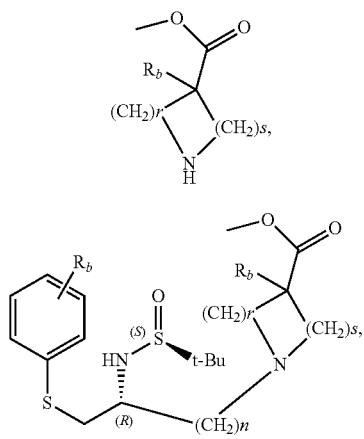

formula (9''''')

formula (10''''')

(8'''') forming a compound of formula (11'''') from the compound of formula (10'''')

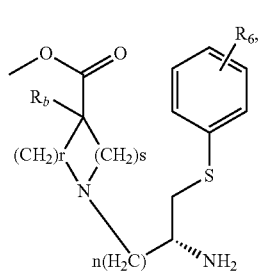

formula (11''''')

(9'''') forming a compound of formula (1'''') from the compound of formula (11'''').

In some embodiments, the step (1'''') is carried out in PhSH, NaOEt, EtOH, and/or at 45-60° C.

In some embodiments, the step (2'''') is carried out in $H_2SO_4$, MeTHF, and/or under reflux.

In some embodiments, step (3'''') is carried out in the presence of PPTS, Dean-stark, MeTHF, and reflux.

In some embodiments, step (4'''') is carried out in the presence of methyl bromoacetate, Zn, DIBAL-H, in THF.

In some embodiments, step (5'''') is carried out in the presence of Red-Al in an organic solvent, preferably toluene.

In some embodiments, step (6'''') is carried out in the presence of MsCl, TEA.

In some embodiments, step (8'''') is carried out in the presence of HCl in a solvent, preferably a polar solvent, preferably methanol.

In some embodiments, step (9'''') is carried out in the presence of $(Boc)_2O/K_2CO_3$ in a solvent, preferably DCM/$H_2O$.

In some embodiments, the preparation of the compound of formula (1'''') comprises the following steps:

(a') reacting a compound of formula (a') with a compound of formula (b') to form a compound of formula (c'),

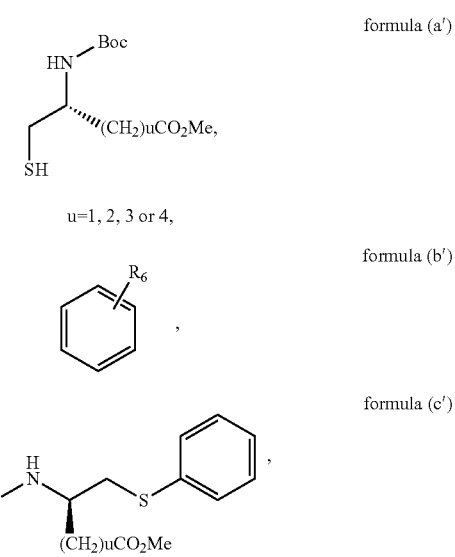

formula (a')

u=1, 2, 3 or 4, formula (b')

formula (c')

(b') forming a compound of formula (d') from the compound of formula (c'),

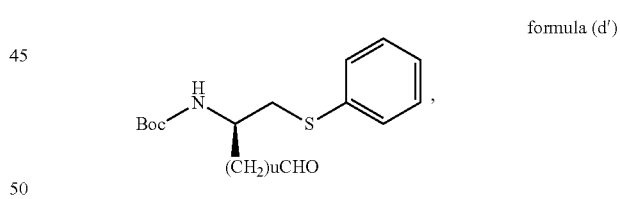

formula (d')

(c') forming a compound of formula (e') from the compound of formula (d'),

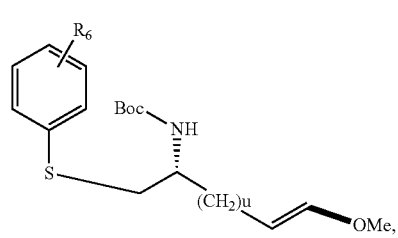

formula (e')

(d') forming a compound of formula (f') from the compound of formula (e'),

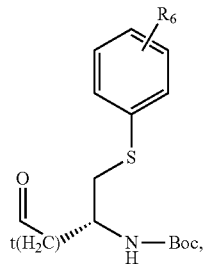

formula (f')

in the formula, t=n−1, n is defined as above, (e') reacting the compound of formula (f') with a compound of formula (g') to form a compound of formula (1""),

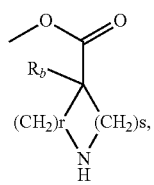

formula (g')

the compound of formula (d') is directly reacted with the compound of formula (g') to form a compound of formula (1"") when u=1.

In some embodiments, step (a') is carried out in the presence of a palladium catalyst, preferably tris(dibenzylideneacetone)dipalladium pd₂(dba)₃, and/or DIPEA, and/or xantphos, in an organic solvent, preferably 1,4-dioxane.

In some embodiments, step (b') is carried out in the presence of a reducing reagent, preferably DIBALH, in an organic solvent, preferably toluene.

In some embodiments, in step (c'), the formula (d') is reacted with MeOCH₂PPh₃Cl, and/or the reaction is carried out at −85° C. to room temperature (RT).

In some embodiments, step (d') is carried out at room temperature under acidic conditions, preferably HCl, more preferably 2M HCl.

In some embodiments, step (e') is carried out at room temperature in the presence of a reducing reagent, preferably NaBH(OAc)₃.

In some embodiments, the preparation of the compound of formula (3"") comprises the following steps:

1''') forming a compound of formula (3"") from a compound of formula 1''',

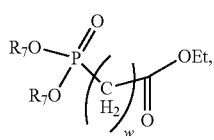

formula 1''' unless otherwise defined, R₇ herein is alkyl, preferably C₁₋₄ alkyl, particularly preferably ethyl, w=1, 2, 3, 4 or 5.

In some embodiments, step 1''') is carried out in a polar organic solvent, more preferably dichloromethane, in the presence of a catalyst, preferably lithium borohydride.

In some embodiments, the preparation of the compound of formula (3"") comprises the following steps:

1"") forming a compound of formula 2"" from a compound of formula 1"", m is 1, 2, 3, 4 or 5,

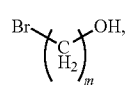

formula 1""

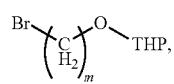

formula 2""

2"") forming a compound of formula 3"" from the compound of formula 2"",

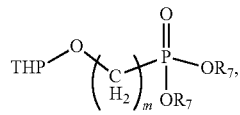

formula 3""

3"") forming a compound of formula (3"") from the compound of formula 3"".

In some embodiments, step 1"") is carried out in the presence of a catalyst such as PPTS, in the presence of DHP, in an organic solvent such as dichloromethane or MTBE.

In some embodiments, in step 2""), the compound of formula 2"" reacts with P(OEt)₃ or PO(OEt)₂ to form a compound of formula (3"").

In some embodiments, step 3"") is carried out in the presence of an ion exchange resin, preferably Amberlite, more preferably Amberlite (10%), in an organic solvent, such as a polar organic solvent, such as a C₁₋₄ alcohol, and/or In the presence of PPTS and/or TFA, and/or in the presence of Dowex (preferably 10%), and/or in the presence of Ambrlyst-15 (preferably 10%).

The foregoing embodiments may be optionally combined.

In some embodiments of the compounds of formula (I) involved in the preparation processes I and II above, R₅ is at the meta position, R₄ is at the para position, and R₆ is hydrogen.

In some embodiments of the compound of formula (I) involved in the aforementioned preparation processes I and II, the compound of formula (I) is a compound having the following structural formula

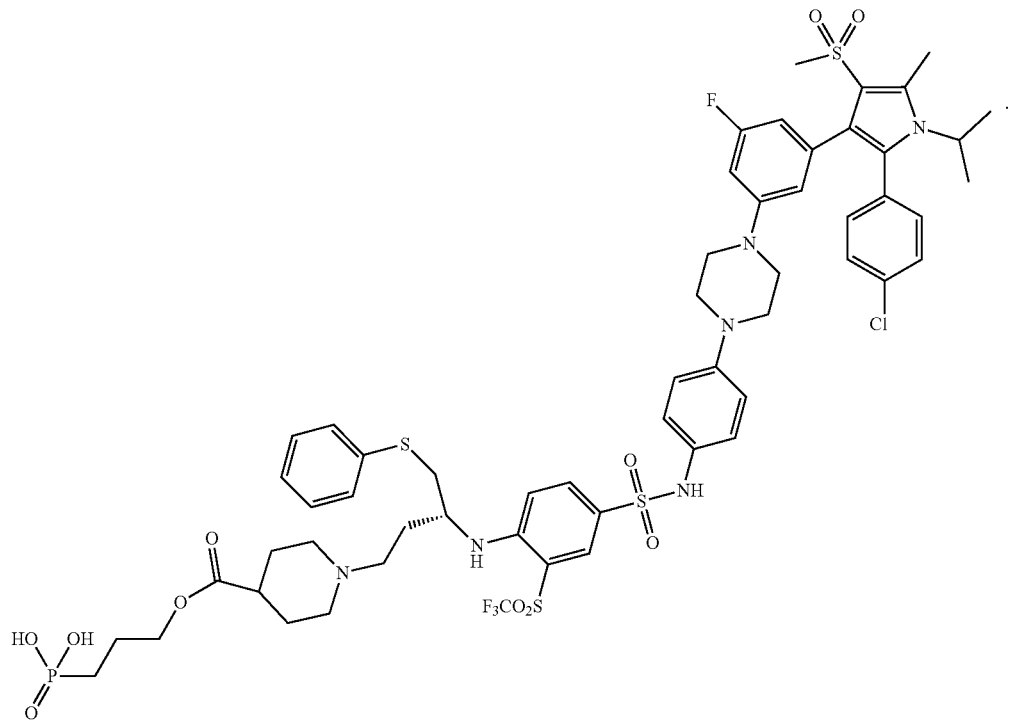

Another aspect of the invention also relates to a process for the preparation of a compound of formula II,

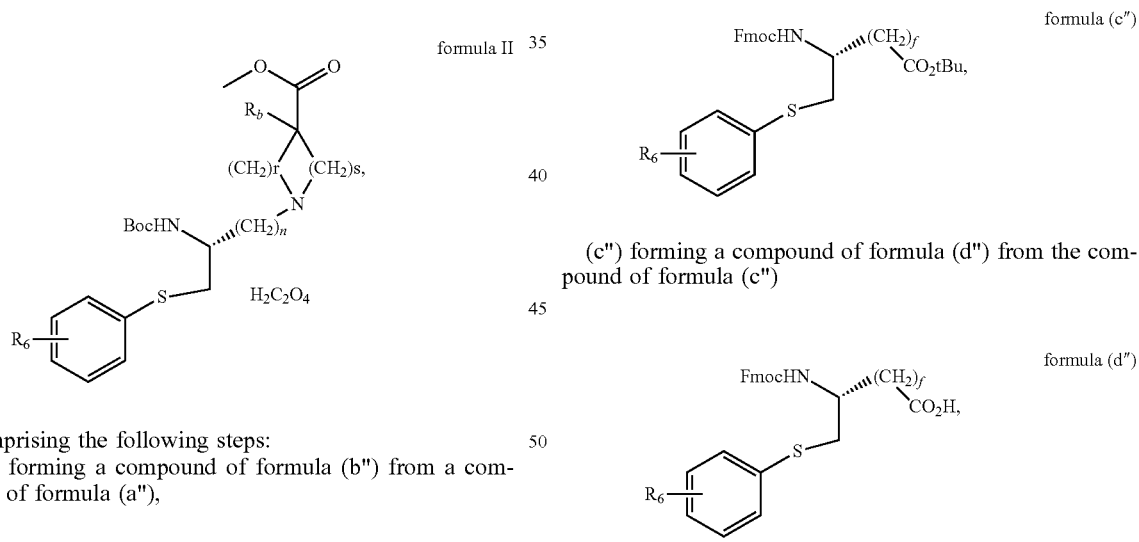

comprising the following steps:
(a") forming a compound of formula (b") from a compound of formula (a"),

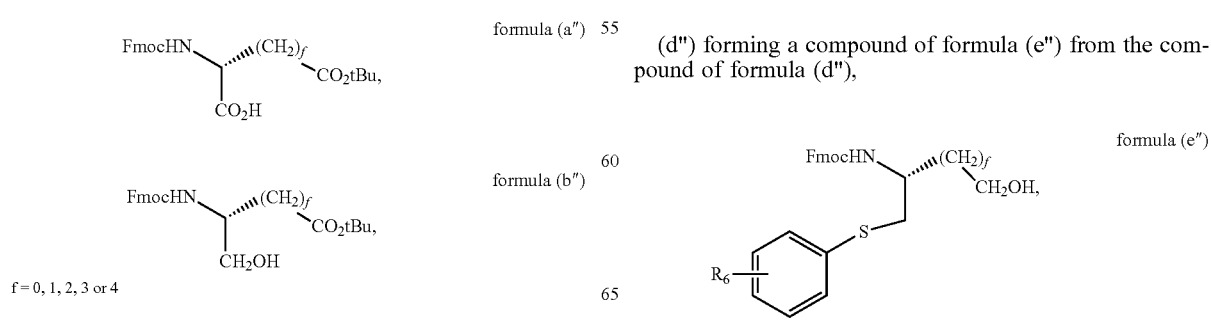

f = 0, 1, 2, 3 or 4

(b") forming a compound of formula (c") from the compound of formula (b")

formula (c")

(c") forming a compound of formula (d") from the compound of formula (c")

formula (d")

(d") forming a compound of formula (e") from the compound of formula (d"), formula (e")

(e") forming a compound of formula (f") from the compound of formula (e"),

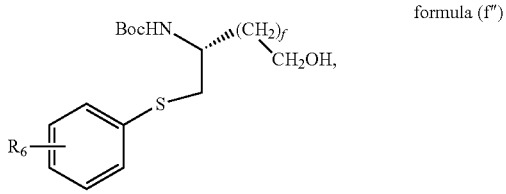

formula (f")

(f") forming a compound of formula (g") from the compound of formula (f"),

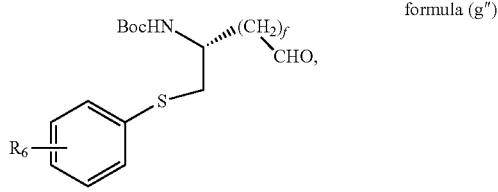

formula (g")

(g") reacting the compound of formula (g") with a compound of formula (h") to form a compound of formula (c"),

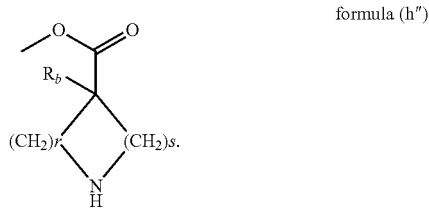

formula (h")

In some embodiments, step (a") is carried out in the presence of $ClCO_2{}^iBu$, and/or NMM, and/or $NaBH_4$, and/or in THF and/or $H_2O$, and/or at −20 to −40° C.

In some embodiments, the step (b") is carried out in an organic solvent, preferably toluene, in the presence of $PH_2S_2$, and/or $Bu_3P$.

In some embodiments, step (c") is carried out under ester hydrolysis conditions, preferably in the presence of TFA, and/or in DCM.

In some embodiments, the step (d") is carried out in the presence of $ClCO_2{}^iBu$, and/or NMM, and/or $NaBH_4$ in THF and/or $H_2O$, and/or at −20 to −40° C.

In some embodiments, the step (e") is carried out in ACN under basic conditions, preferably in the presence of $NHEt_2$, and may also be carried out in the presence of $(Boc)_2O$, and/or $Na_2CO_3$.

In some embodiments, the step (f") is carried out in DMSO and/or DCM in the presence of oxidizing conditions, preferably $SO_3.Py$, and/or TEA.

In some embodiments, the step (g") is carried out in the presence of $NaBH(OAc)_3$ in DCM at 0-25° C.

The compound of formula II can be used to replace a compound of formula (1"") to prepare a compound of formula (2"").

Another aspect of the invention also relates to a process for preparing a compound of formula 2, comprising the following steps:

1) hydrolyzing a compound of formula 1 to form a compound of formula 2,

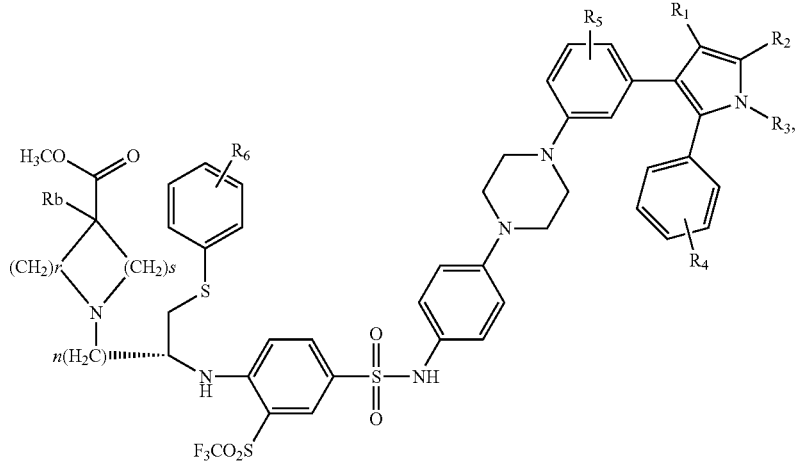

formula 1

-continued formula 2

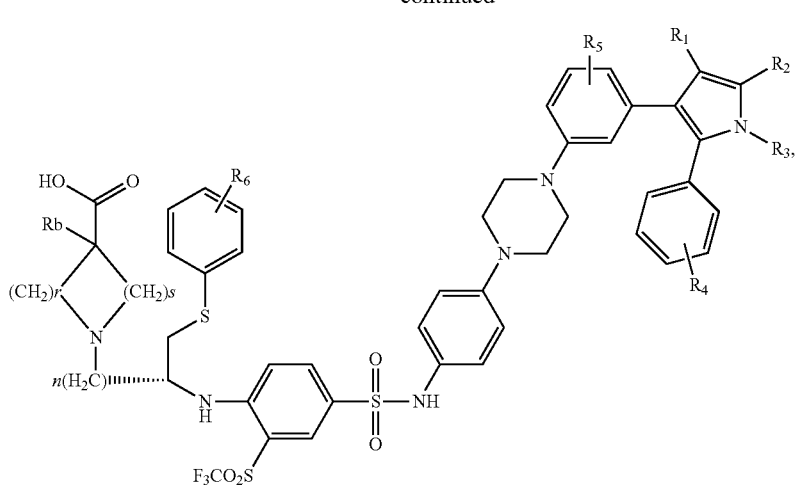

In some embodiments, step 1) is carried out in the presence of a base in a solvent, and preferably, the base is a hydroxide, preferably sodium hydroxide, and the solvent is a polar solvent, preferably water and tetrahydrofuran.

Another aspect of the invention is related to compounds of the above formula 1, formula (2), formula (1'''') to formula (3''''), formula II, and compounds having the following structural formulae -continued

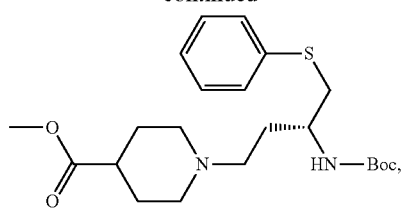

m-K

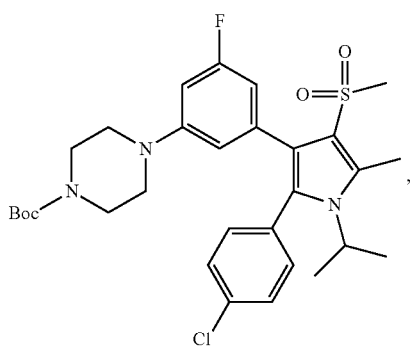

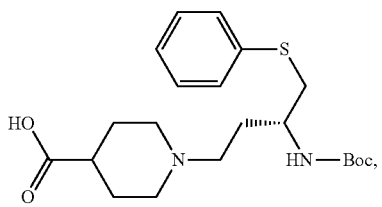

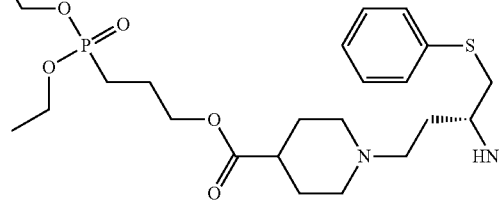

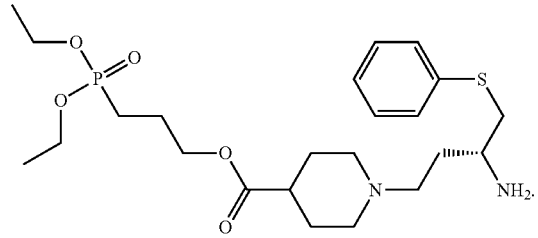

m-L

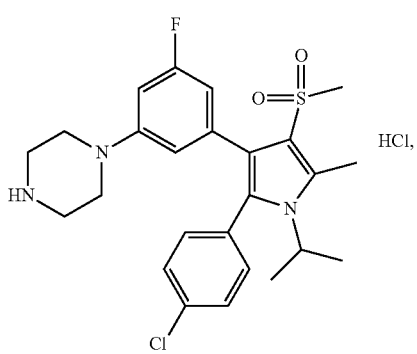

HCl,

The compound can be used as an intermediate for the preparation of the compound of formula (I).

Another aspect of the invention also relates to the use of any of the foregoing intermediate compounds in the preparation of a compound of formula (I).

The beneficial effects of the invention:

The present invention provides an excellent process for preparing a compound of formula (I), in particular, a process for preparing compound 1. In particular, the process II of the invention avoids high-performance liquid phase preparation and lyophilization operation, further shortens preparation time, improves the yield, and thereby is more suitable for large scale production. In particular, the process II of the invention can avoid high-performance liquid phase preparation, while ensuring that the key indicators of the compound of formula (I) meet the requirements, achieving production above the kilogram level, making it easier to control the ratio of the reaction materials, and the choice of the base and the amount thereof, the choice of the solvent, the choice of the solvent, the reaction temperature, the dropping rate, and the post-treatment process all increase the yield and the purity of the product. The reaction conditions of the invention can achieve higher conversion rate under mild reaction conditions and can effectively control the formation of key impurities.

Specific Modes for Carrying Out the Invention

The present invention is further illustrated by specific preparation examples and effect experiments, but it should be understood that these examples and effect experiments are only used for illustrations in more detail, and should not be construed as any limitation to the invention.

Preparation Example 1

In this example, Compound 1 is prepared by the specific preparation process including the following and corresponding to process I:

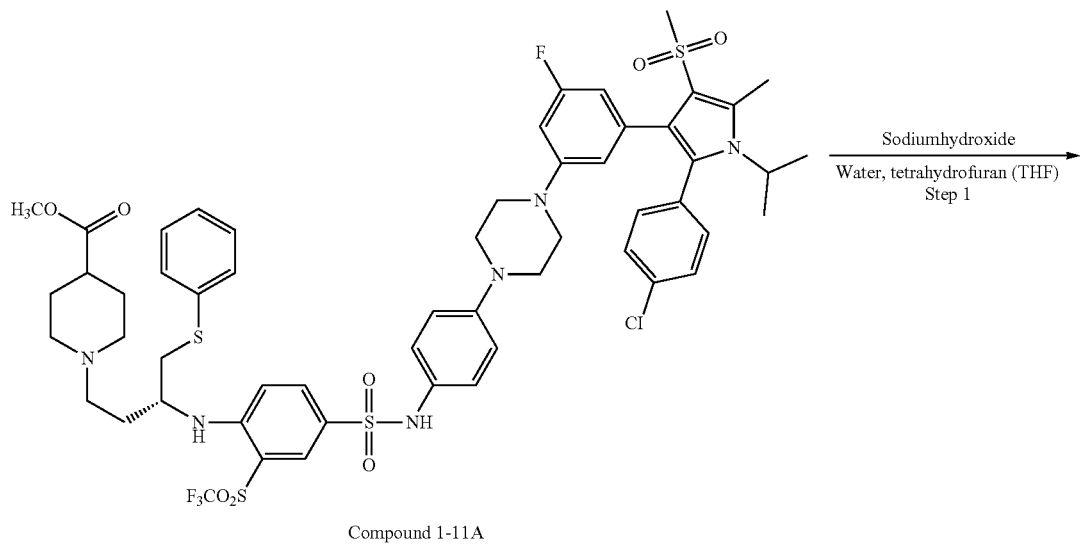

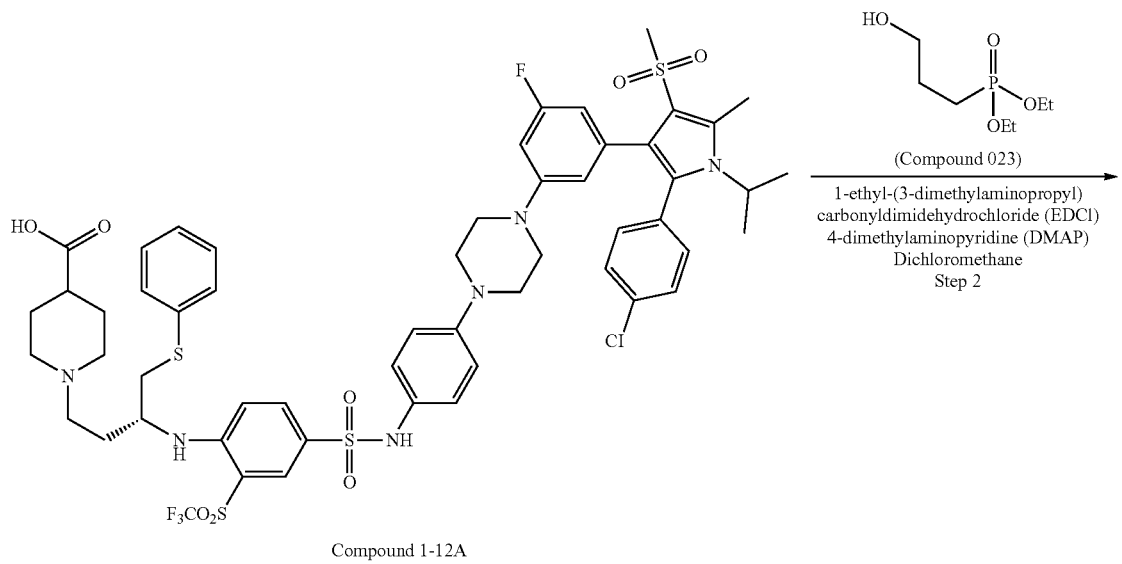

-continued
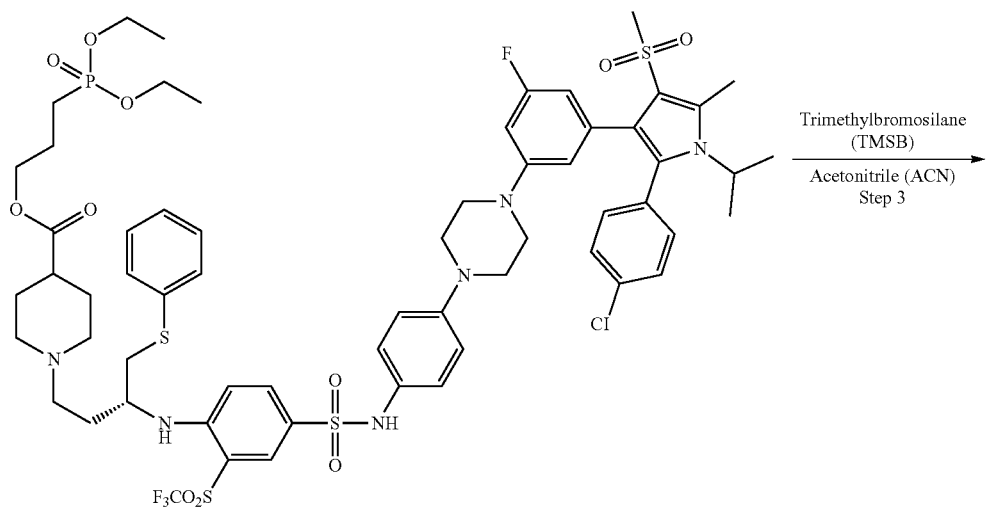
Compound 1-13A
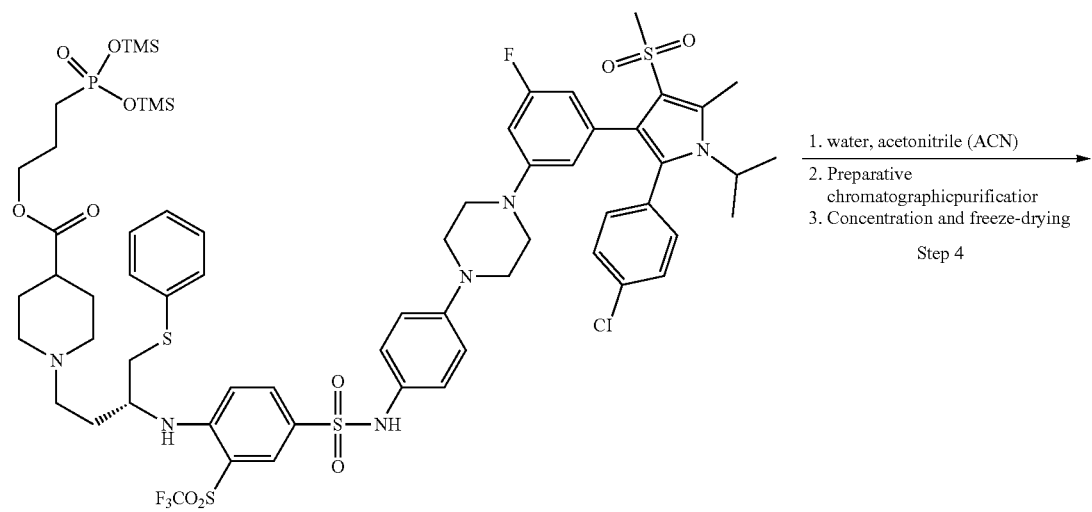
Compound 1-14A
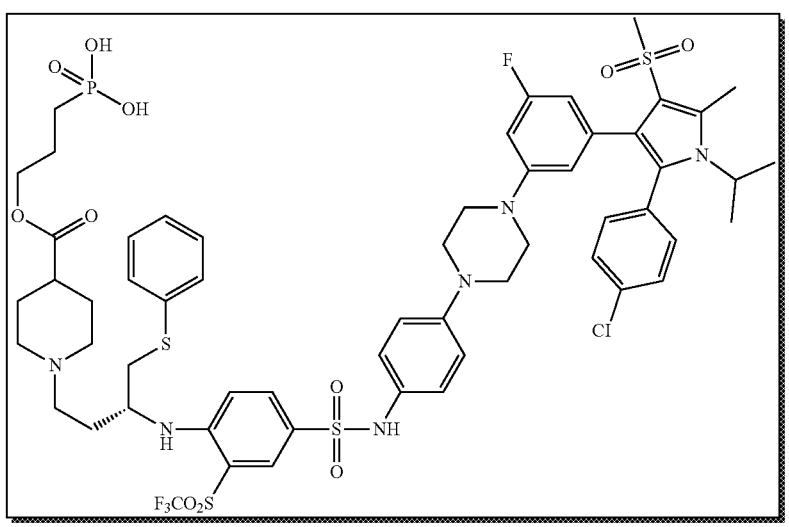
Compound 1

The synthesis process of Compound 1 is as follows:

Step 1: Preparation of Compound 1-12A

Compound 1-11A (566 g) was dissolved in tetrahydrofuran at room temperature, and a pre-formulated aqueous solution of sodium hydroxide was added, stirred at room temperature, monitored by IPC (monitoring during production), and 1N aqueous hydrochloric acid solution was added dropwise to the reaction system after the disappearance of the raw materials. The pH of the reaction system was adjusted to 1-2; then the reaction system was extracted with dichloromethane; the organic phase was combined, dried over anhydrous magnesium sulfate, filtered, and the filter cake was washed with dichloromethane, and the filtrate was concentrated to dryness under reduced pressure, dried in vacuum to obtain compound 1-12A. Yield 90-110%.

Step 2: Preparation of Compound 1-13A

Compound 1-12A (567 g) was dissolved in dichloromethane at room temperature, and compound 023 (474 g), DMAP, EDCI were added in sequence; the reaction solution was stirred under nitrogen for 3±0.5 hours, monitored by IPC, and the solution was diluted with methylene chloride after the reaction disappeared. The organic phase was washed once with water, saturated aqueous solution of sodium hydrogen carbonate and saturated aqueous solution of sodium chloride, respectively, dried over anhydrous magnesium sulfate, filtered, and the filter cake was washed with dichloromethane, and the filtrate was concentrated to dryness under reduced pressure; the crude product obtained was subjected to column chromatography; the eluate was concentrated, dried in vacuum to give compound 1-13A. Yield 60-80%.

Step 3: Preparation of Compound 1-14A

Compound 1-13A (404 g) was dissolved in acetonitrile solution at room temperature, the reaction system was protected with nitrogen, trimethylbromosilane was added dropwise, and after the addition was completed, the system was heated to 60±2° C., stirred for about 1 hour while keeping the same temperature; IPC monitoring was carried out. After the disappearance of the raw materials, the reaction solution was directly concentrated to dryness, and dried under vacuum to obtain compound 1-14A. Yield 100-120%.

Step 4: Preparation of Compound 1

Compound 1-14A was dissolved in a mixture of acetonitrile and purified water (v/v=8/2) at a concentration of about 50 mg/ml. The sample was purified by a preparative high-performance liquid chromatograph, the product was collected, concentrated, and a small amount of acetonitrile was added thereto to dissolve the product to obtain a clear solution. The product was enriched by a preparative high-performance liquid chromatograph, and the solvent was removed by freeze-drying to obtain compound 1. Yield 50-80%.

$^1$H NMR (400 MHz, DMSO-$d_6$) δ 9.88 (s, 1H), 7.80 (d, J=2.2 Hz, 1H), 7.66 (dd, J=9.3, 2.3 Hz, 1H), 7.43-7.34 (m, 2H), 7.30-7.25 (m, 4H), 7.25-7.14 (m, 3H), 6.99 (d, J=9.6 Hz, 1H), 6.93 (d, J=8.9 Hz, 2H), 6.90-6.80 (m, 3H), 6.63-6.46 (m, 2H), 6.41-6.33 (m, 1H), 4.42-4.22 (m, 1H), 4.06 (t, J=6.4 Hz, 3H), 3.30 (ddd, J=45.4, 14.0, 5.8 Hz, 2H), 3.10 (dd, J=18.6, 5.2 Hz, 8H), 2.93 (s, 4H), 2.67 (s, 4H), 2.39 (d, J=30.5 Hz, 3H), 2.14 (d, J=37.4 Hz, 2H), 1.97 (d, J=10.3 Hz, 1H), 1.78 (s, 5H), 1.63 (s, 2H), 1.49 (dt, J=16.7, 7.8 Hz, 2H), 1.35 (d, J=7.0 Hz, 6H).

The compound 1-11A involved in the present invention is preferably synthesized by the following process:

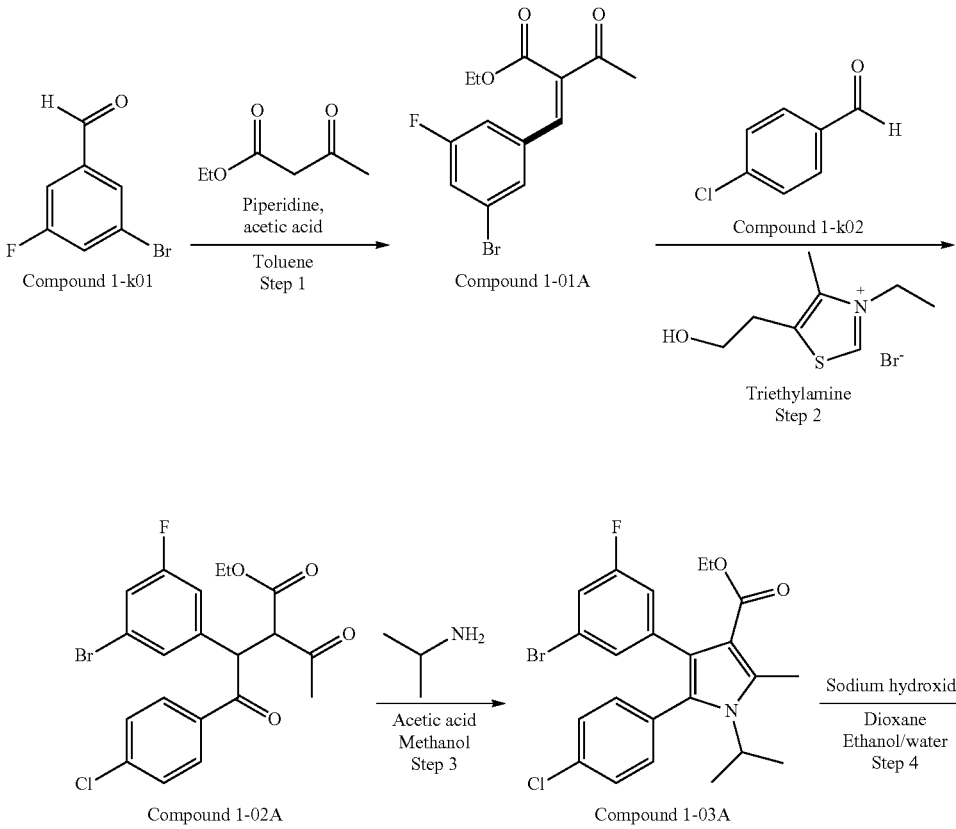

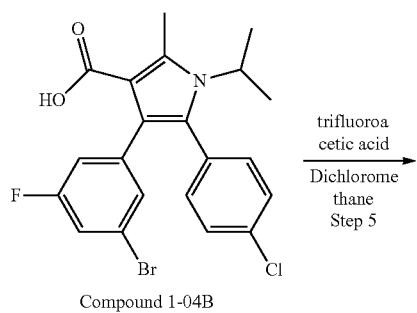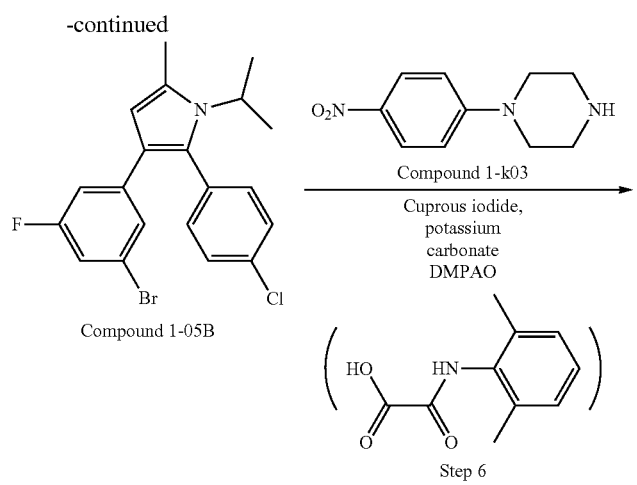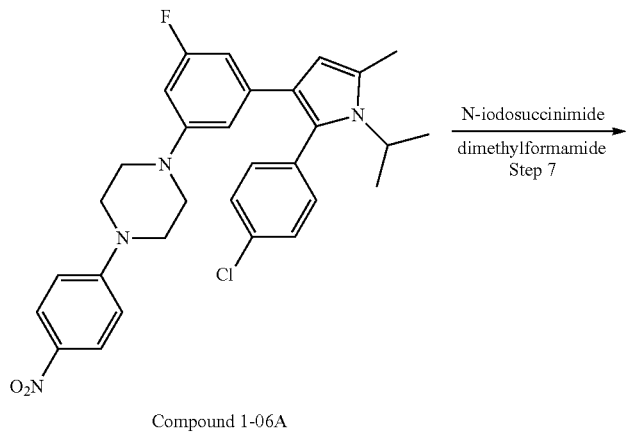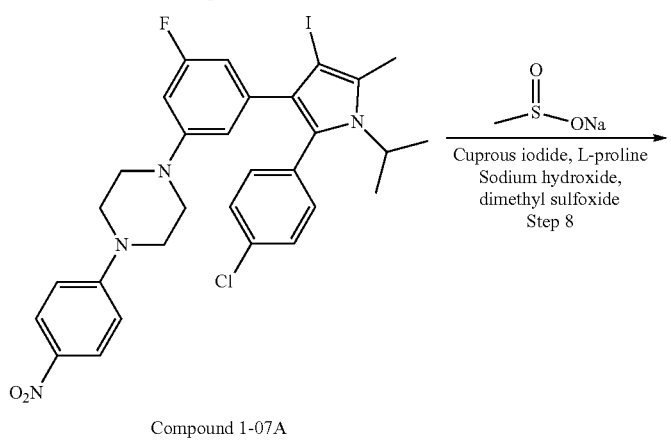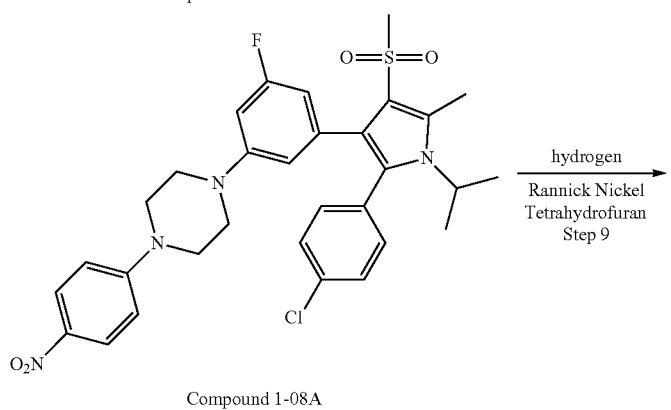

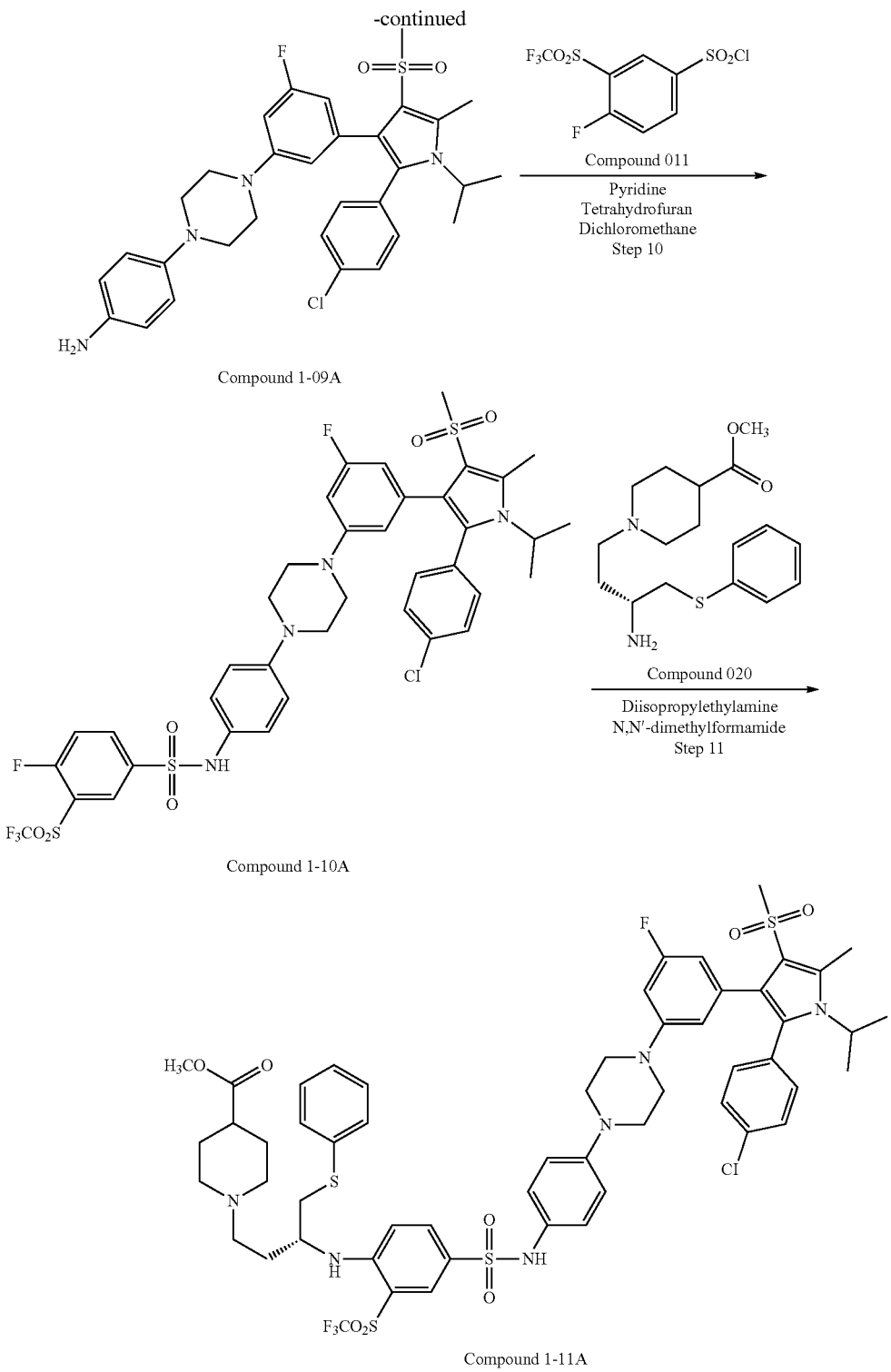

The synthesis process of compound 1-11A was as follows:
Step 1: Preparation of Compound 1-01A
The material compound 1-k01 (500 g), ethyl acetoacetate (354 g), piperidine (16 mL), acetic acid (50 mL) were added to toluene (1.8 L), and heated to reflux to remove water formed in the reaction, TLC (thin layer chromatography) was carried out until the disappearance of the compound 1-k01. The reaction system was cooled to room temperature, diluted with ethyl acetate, and the organic phase was washed, dried over anhydrous magnesium sulfate and filtered to give a brown-red oil. The crude compound 1-01A was used directly in the next step.

Step 2: Preparation of Compound 1-02A
The crude compound 1-01A (1560 g) obtained in the step 1 was added to absolute ethanol (8 L), and the compound 1-k02 (696 g), triethylamine (1000 g), 3-ethyl-5-(2-Hydroxyethyl)-4-methylthiazole bromide (187 g) were added respectively, and the system was purged with nitrogen, heated to 70±2° C., and stirred while keeping the same temperature. TLC was carried out to monitor the reaction until compound 1-01A disappeared, thereafter the reaction system was cooled to room temperature, concentrated, diluted with ethyl acetate, and the organic phase was washed, dried over anhydrous magnesium sulfate, filtered, and concentrated to give a brown-red oil. The crude compound 1-02A was used directly in the next step.

Step 3: Preparation of Compound 1-03A

The crude compound 1-02A (2256 g) obtained in the step 2 was added to methanol (12.6 L), and isopropylamine (4.34 L) and acetic acid (2.86 L) were sequentially added, and nitrogen gas was introduced thereto, and the system was heated to 50±2° C., and stirred while keeping the same temperature, and TLC was carried out to monitor the reaction until compound 1-02A disappeared, thereafter the reaction system was cooled to room temperature, concentrated under reduced pressure, and diluted with ethyl acetate. The organic phase was washed and dried over anhydrous magnesium sulfate. The crude product was subjected to column chromatography using a system of petroleum ether and ethyl acetate to afford white solid compound 1-03A. (First three steps yield: ~40%)

Step 4: Preparation of Compound 1-04B

Compound 1-03A (2440 g) was added to a mixed solution of 1, 4-dioxane (12.2 L), ethanol (12.2 L), and water (12.2 L), and sodium hydroxide (8 Kg) was added thereto, heated to reflux, stirred while keeping the same temperature. TLC was carried out to monitor the reaction until the disappearance of compound 1-03A, thereafter the reaction system was cooled to room temperature, concentrated under reduced pressure, and pH was adjusted to 1-2, and a large amount of solid was precipitated, filtered, and filter cake was washed with water, solid was dried in vacuum to give white solid compound 1-04B, which was directly used for the next reaction. (Yield: ~95%)

Step 5: Preparation of Compound 1-05B

The compound 1-04B (2164 g) was added to a mixed solution of dichloromethane (3.1 L) and trifluoroacetic acid (9.3 L), which was purged with nitrogen, stirred at room temperature. TLC was carried out to monitor the reaction until compound 1-05B disappeared, thereafter the system was added with dichloromethane (3 L) for dilution, and water (6 L), and stirred for 0.5 h, and then was allowed to stand to separate into layers, and the aqueous layer was extracted with methylene chloride. The organic phase was combined, washed, dried over anhydrous magnesium sulfate, filtered and concentrated to give compound 1-05B, which was used directly in the next reaction. (Yield: ~95%)

Step 6: Preparation of Compound 1-06A

To dimethyl sulfoxide (3.2 L) was added Compound 1-05B (320 g), followed by 1-(nitrophenyl)piperazine (489 g), cuprous iodide (74 g), 2,6-dimethyl phenyl carbamoyl-formic acid (152 g), potassium carbonate (434 g), respectively. The reaction system was protected with nitrogen, heated to 120±5° C., and stirred while keeping the same temperature. TLC was carried out to monitor the reaction. After most of the raw materials had been reacted, the reaction system was cooled to room temperature. The reaction was quenched by the addition of saturated aqueous solution of ammonium chloride. The aqueous phase was extracted with ethyl acetate for several times, and the organic phases were combined, washed and dried over anhydrous magnesium sulfate. The crude product was subjected to column chromatography with a system of petroleum ether, ethyl acetate and dichloromethane to give a yellow solid compound 1-06A. (Yield: ~55%)

Step 7: Preparation of Compound 1-07A

Compound 1-06A (673 g) was added to N,N-dimethylformamide (7.5 L), and the system was purged with nitrogen, cooled to 0±5° C., and iodosuccinimide (341 g) was added thereto and thereafter cooling was stopped, and the system was shielded from light, and stirred at room temperature. TLC was carried out to monitor the reaction until the compound 1-06A disappeared. The reaction solution was concentrated to dryness, and the crude product was added to a mixture of petroleum ether and ethyl acetate (v/v=3/1) (1.5 L). The mixture was stirred at room temperature, filtered, and the filter cake was washed with a mixture of petroleum ether and ethyl acetate (v/v=3/1), and dried in vacuum to give a yellow solid compound 1-07A, which was directly used for the next reaction. (Yield: ~95%)

Step 8: Preparation of Compound 1-08A

To dimethyl sulfoxide (3 L) was added Compound 1-07A (300 g), followed by sodium methanesulfinate (464 g), cuprous iodide (52 g), L-proline (52 g), sodium hydroxide (36 g). The reaction system was protected by nitrogen, heated to 100±5° C., stirred while keeping the same temperature. TLC was carried out to monitor the reaction, after most of the raw materials had been reacted, the reaction system was cooled to room temperature, and the reaction was quenched by adding saturated ammonium chloride solution. The aqueous phase was extracted with ethyl acetate for several times. The organic phase was combined, washed and dried over anhydrous magnesium sulfate. The crude product was subjected to column chromatography with a system of petroleum ether, ethyl acetate and dichloromethane to give a yellow solid compound 1-08A. (Yield: ~55%)

Steps 9 and 10: Preparation of Compound 1-09A, Compound 1-10A

To tetrahydrofuran (1.2 L) was added compound 1-08A (120 g), Raney nickel (180 g) under stirring. The reaction system was purged with hydrogen, and stirred under hydrogenation conditions at room temperature. TLC was carried out to monitor the reaction until compound 1-08A disappeared and thereafter the reaction was stopped, filtered to remove Raney nickel, and the filtrate was directly used for subsequent reaction;

Compound 011 (96 g) was added to dichloromethane (1 L). The system was cooled to −5±5° C. To the system was added pyridine (40 mL), and was slowly added the filtrate in the step 9 dropwise, and stirred. TLC was carried out to monitor the reaction until the disappearance of compound 1-09A, thereafter methylene chloride (3 L) was added. The organic phase was washed twice with water, dried over anhydrous magnesium sulfate, and the crude product was subjected to column chromatography with a system of petroleum ether, ethyl acetate and dichloromethane to give pale yellow solid compound 1-10A. (Two-step yield: ~70%)

Step 11: Preparation of Compound 1-11A

To N,N-dimethylformamide (6 L) was added compound 1-10A (487 g), compound 020 (207 g), diisopropylethylamine (285 mL), and the system was purged with nitrogen gas, and stirred at room temperature. TLC was carried out to monitor the reaction until the disappearance of the compound 1-10A. The reaction solution was directly concentrated to dryness, and the crude product was subjected to column chromatography with a system of methylene chloride and methanol to give a pale yellow solid compound 1-11A. (Yield: ~90%)

$^1$H NMR (400 MHz, DMSO-d$_6$) δ 9.76 (s, 1H), 7.83 (d, J=2.2 Hz, 1H), 7.60 (dd, J=9.3, 2.3 Hz, 1H), 7.38 (d, J=8.5

Hz, 2H), 7.34-7.14 (m, 7H), 7.01-6.80 (m, 6H), 6.65-6.50 (m, 2H), 6.47-6.31 (m, 1H), 4.34 (q, J=7.0 Hz, 1H), 4.06 (s, 1H), 3.59 (s, 3H), 3.43-3.22 (m, 2H), 3.19-3.00 (m, 8H), 2.90 (s, 3H), 2.68 (s, 4H), 2.33-2.14 (m, 3H), 1.91 (t, J=11.0 Hz, 2H), 1.74 (dq, J=30.4, 14.7, 13.0 Hz, 4H), 1.56-1.27 (m, 8H).

Compound 020 can be synthesized by the following steps:

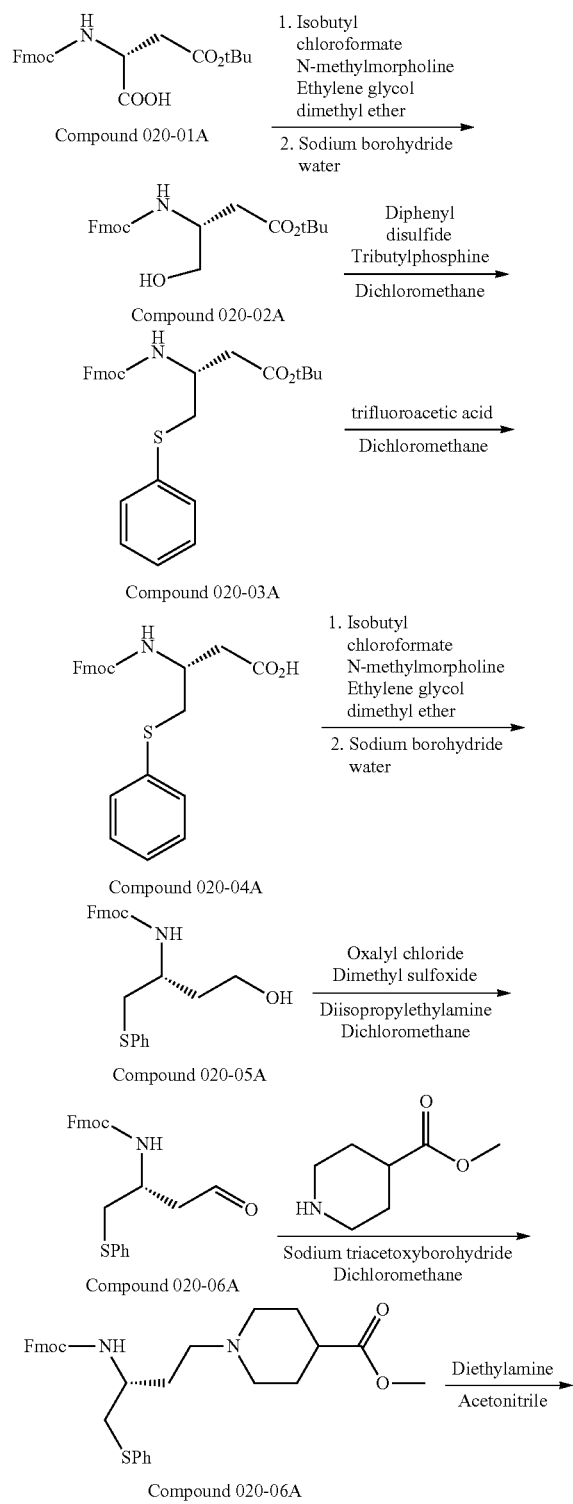

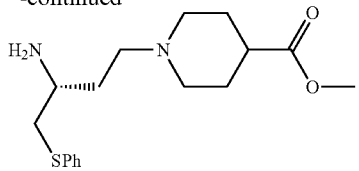

Compound 020

The step 1: preparation of compound 020-02A

To ethylene glycol dimethyl ether (300 mL) was added Compound 020-01A (100.0 g), N-methylmorpholine (27.0 g). The system was purged with nitrogen gas, cooled to −8±2° C., added isobutyl chloroformate (36.5 g) dropwise, and stirred. TLC was carried out to monitor the reaction until compound 020-01A disappeared, thereafter the reaction solution was filtered, purged with nitrogen gas, and added a mixed solution of sodium borohydride (13.5 g) and water (160 mL) dropwise. After completion of the addition, the reaction system was warmed to room temperature, stirred, diluted with water, and extracted with ethyl acetate. The organic phase was combined, washed, dried over anhydrous magnesium sulfate, filtered and concentrated to give the product compound 020-02A, which was used directly in the next step of synthesis.

Step 2: Preparation of Compound 020-03A

To dichloromethane (650 mL) was added Compound 020-02A (96.6 g), tributylphosphine (108.2 g), and diphenyl disulfide (116.8 g). The reaction system was purged with nitrogen gas, and stirred at room temperature. TLC was carried out to monitor the reaction until the compound 020-02A disappeared. The reaction solution was washed with water, dried over anhydrous magnesium sulfate, filtered, and the filtrate was concentrated and used directly for subsequent reaction.

Step 3: Preparation of Compound 020-04A

The compound 020-03A obtained in the step 2 was transferred to another reaction vessel which was purged with nitrogen gas, added trifluoroacetic acid (148 g) dropwise, and the mixture was stirred at room temperature. TLC was carried out to monitor the reaction until the compound 020-03A disappeared. The reaction solution was washed with water and was allowed to stand to separate into layers. The aqueous phase was extracted with dichloromethane. The organic phase was combined, dried over anhydrous magnesium sulfate, filtered, concentrated, and washed with ethyl acetate/n-hexane (v/v=1/6). The solid was dried in vacuum to give compound 020-04A. (The first three steps yield: 55%).

Step 4: Preparation of Compound 020-05A

To ethylene glycol dimethyl ether (240 mL) was added Compound 020-04A (60 g), and N-methylmorpholine (15.4 g). The reaction system was purged with nitrogen gas, cooled to −8±2° C. To the reaction system was added isobutyl chloroformate (20.7 g) dropwise, and the reaction system was stirred. TLC was carried out to monitor the reaction until compound 020-04A disappeared, thereafter the reaction solution was filtered, and purged with nitrogen gas. The system was cooled to −15±2° C., added a solution of sodium borohydride (7.8 g) in water (100 mL) dropwise and stirred for 45±15 minutes. The reaction system was diluted with water, and extracted with ethyl acetate. The organic phase was combined, washed, dried over anhydrous magnesium sulfate, filtered and concentrated to give the product compound 020-05A, which was used directly in the next step of synthesis. (Yield: ~90%).

Step 5: Preparation of Compound 020-06A

To dichloromethane (600 mL) was added oxalyl chloride (49.6 g). The reaction system was purged with nitrogen gas, cooled to −60±5° C. To the reaction system was added a mixture of dimethyl sulfoxide (50.9 g) dissolved in dichloromethane (240 ml) dropwise, and the reaction system was stirred while keeping the same temperature for 1.0 hour, then added the mixed solution of compound 020-05A (54.7 g) in dichloromethane (360 mL), stirred for 1.5 hours while keeping the temperature of −60±5° C., then added diisopropylethylamine (101.2 g) dropwise, and warmed to room temperature. The reaction system was diluted with water, stirred at room temperature for 24 hours, and then allowed to stand to separate into layers. The aqueous phase was extracted with dichloromethane, and the organic phase was combined, washed and dried over anhydrous magnesium sulfate, filtered and concentrated. The crude product was subjected to column chromatography with a system of petroleum ether and ethyl acetate to give white solid compound 020-06A. (Yield: ~70%).

Step 6: Preparation of Compound 020-07A

To dichloromethane (500 mL) was added Compound 020-06A (26.6 g), and methyl 4-piperidinecarboxylate (9.9 g). The reaction system was purged with nitrogen gas, stirred at room temperature for 2.0 hours, then to the reaction system was added sodium triacetoxyborohydride (26.5 g), and the reaction system was stirred at room temperature. TLC was carried out to monitor the reaction until the compound 020-06A disappeared, thereafter the reaction system was diluted with water, and allowed to stand to separate into layers. The aqueous phase was extracted with dichloromethane, and the organic phase was combined, washed and dried over anhydrous magnesium sulfate, filtered, and concentrated to give compound 020-07A. The crude product was directly used for the next step.

Step 7: Preparation of Compound 020

To acetonitrile (360 mL) was added Compound 020-07A (37.6 g), and diethylamine (114 mL). The reaction system was purged with nitrogen gas, stirred at room temperature. TLC was carried out to monitor the reaction until the compound 020-07A disappeared, thereafter the reaction solution was concentrated to dryness. The crude product was subjected to column chromatography with a system of dichloromethane and methanol to give the compound 020 as an oil. (Two-step yield: ~50%)

$^1$H NMR (400 MHz, chloroform-d) δ 7.35 (dd, J=8.3, 1.3 Hz, 2H), 7.26 (dd, J=8.5, 6.9 Hz, 2H), 7.21-7.07 (m, 1H), 3.66 (s, 3H), 3.11 (dd, J=13.1, 4.3 Hz, 1H), 2.97 (tt, J=8.4, 4.5 Hz, 1H), 2.85 (dd, J=22.2, 11.4 Hz, 2H), 2.74 (dd, J=13.2, 8.3 Hz, 1H), 2.39 (dddd, J=20.0, 12.6, 7.5, 5.5 Hz, 2H), 2.27 (tt, J=11.1, 4.0 Hz, 1H), 1.99-1.62 (m, 9H), 1.61-1.47 (m, 1H).

The compound 011 of the present invention can be synthesized by the following steps:

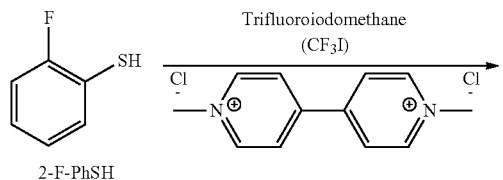

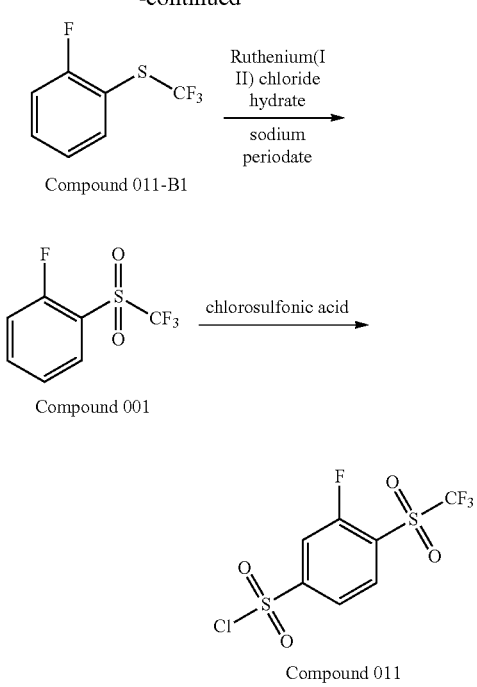

The synthesis process was as follows:

<Step 1> Preparation of Compound 011-B1

When the temperature was controlled at −25±5° C., trifluoroiodomethane (100 g) was introduced into N,N-dimethylformamide (225 mL). To the reaction system was added 1,1'-dimethyl-4,4'-dichlorodipyridine (4.37 g), 2-fluorothiophenol (43.6 g) under protection by nitrogen, then added triethylamine (48.2 g) dropwise. After the addition was completed, the reaction system was warmed to room temperature, stirred for 24 hours, and water (800 mL) was added to the reaction system. The reaction solution was extracted with diethyl ether, and the organic phase was combined, washed, dried over anhydrous magnesium sulfate, filtered, and evaporated under reduced pressure to give the product of compound 011-B1 as an oil, yield: ~85%.

<Step 2> Preparation of Compound 001

To a mixed solution of carbon tetrachloride (170 mL), acetonitrile (170 mL) and water (340 mL) was added Compound 011-B1 (56 g), sodium periodate (183 g) and ruthenium(III) chloride hydrate (0.59 g), and stirred at room temperature. TLC was carried out to monitor the reaction until the compound 011-B1 disappeared, thereafter the solution was added dichloromethane (300 mL), and filtered. The pH of the filtrate was adjusted to 7-8, and the filtrate allowed to stand to separate into layers. The aqueous phase was extracted with dichloromethane, and the organic phase was combined, washed, dried over anhydrous magnesium sulfate, and the crude product was subjected to column chromatography with a system of petroleum ether and ethyl acetate to give compound 001 as an oily product, yield: ~90%.

<Step 3> Preparation of Compound 011

To chlorosulfonic acid (4 mL) was added Compound 001 (4 g). The reaction system was purged with nitrogen gas, heated to 120±5° C., stirred while keeping the same temperature for 24 hours, thereafter the system was cooled to room temperature, and the reaction solution was slowly poured into a mixed system of ice (40 mL) and ethyl acetate (25 mL) under stirring, allowed to stand to separate into layers. The aqueous phase was extracted with ethyl acetate, and the organic phase was combined, washed, dried over anhydrous magnesium sulfate, filtered, and concentrated to give compound 011 as an oily product, yield: ~60%.

Compound 011: $^1$H NMR (400 MHz, chloroform-d) δ 8.71 (dd, J=5.8, 2.5 Hz, 1H), 8.54 (ddd, J=8.9, 4.1, 2.5 Hz, 1H), 7.68 (t, J=8.7 Hz, 1H).

The compound 023 to which the present invention relates can be produced by the following steps:

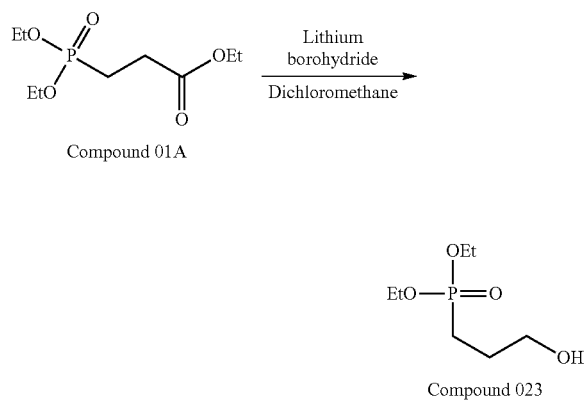

Compound 023-01A (132 g) was added to dichloromethane (1.4 L) at room temperature. The reaction system was purged with nitrogen gas, and to the reaction system was added lithium borohydride (18.1 g) portionwise, and the reaction system was stirred. TLC was carried out to monitor the reaction until compound 023-01A disappeared. To the reaction system was added saturated sodium carbonate aqueous solution (400 mL) slowly, and the reaction system was stirred for 30 minutes, and allowed to stand to separate into layers. The aqueous phase was extracted with dichloromethane, and the organic phase was combined, washed, dried over anhydrous magnesium sulfate, filtered and concentrated. The crude product was subjected to column chromatography with a system of methylene chloride and methanol to give Compound 023 as an oily product, yield: ~50%.

Compound 023: $^1$H NMR (400 MHz, DMSO-d$_6$) δ 4.53 (t, J=5.3 Hz, 1H), 3.98 (dqd, J=8.1, 7.0, 3.8 Hz, 4H), 3.50-3.36 (m, 2H), 1.80-1.50 (m, 4H), 1.23 (t, J=7.0 Hz, 6H).

The compound 023 to which the present invention relates can also be produced by the following steps:

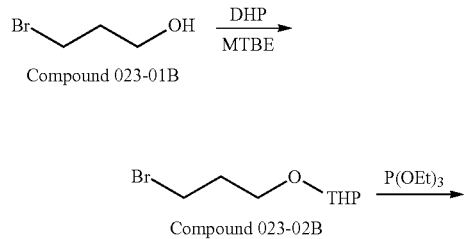

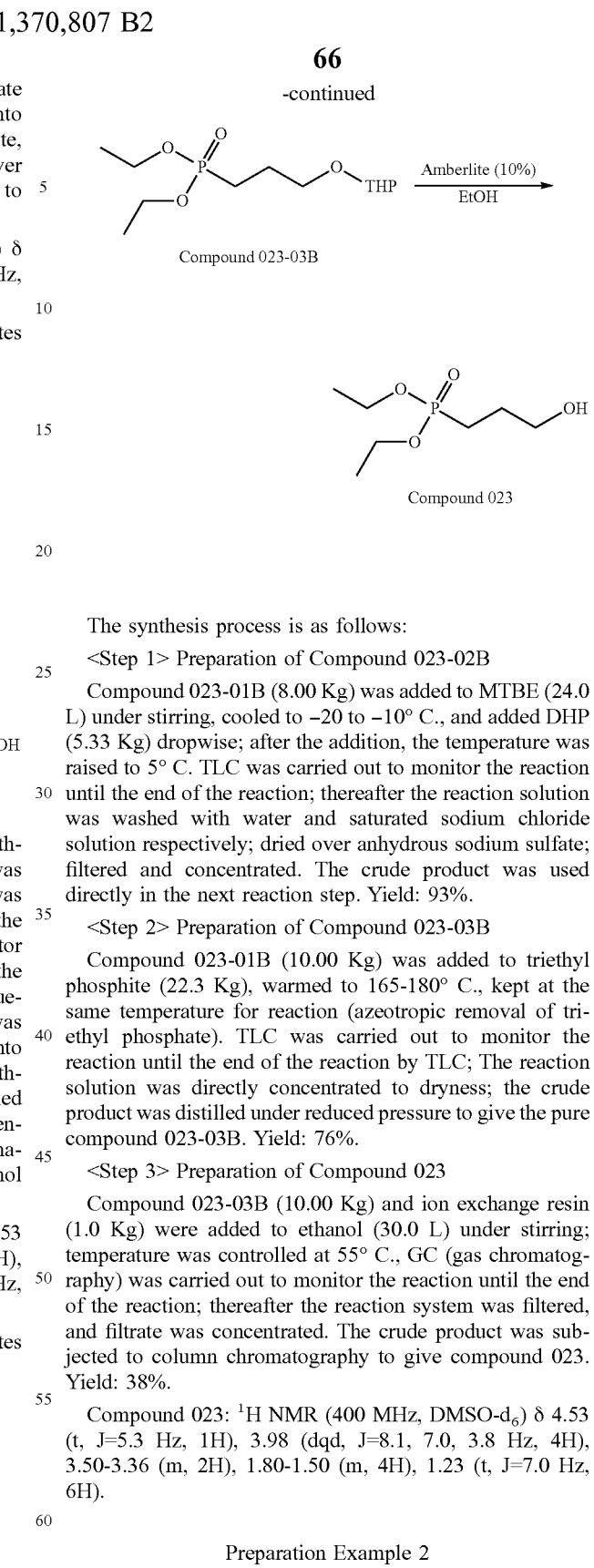

The synthesis process is as follows:

<Step 1> Preparation of Compound 023-02B

Compound 023-01B (8.00 Kg) was added to MTBE (24.0 L) under stirring, cooled to −20 to −10° C., and added DHP (5.33 Kg) dropwise; after the addition, the temperature was raised to 5° C. TLC was carried out to monitor the reaction until the end of the reaction; thereafter the reaction solution was washed with water and saturated sodium chloride solution respectively; dried over anhydrous sodium sulfate; filtered and concentrated. The crude product was used directly in the next reaction step. Yield: 93%.

<Step 2> Preparation of Compound 023-03B

Compound 023-01B (10.00 Kg) was added to triethyl phosphite (22.3 Kg), warmed to 165-180° C., kept at the same temperature for reaction (azeotropic removal of triethyl phosphate). TLC was carried out to monitor the reaction until the end of the reaction by TLC; The reaction solution was directly concentrated to dryness; the crude product was distilled under reduced pressure to give the pure compound 023-03B. Yield: 76%.

<Step 3> Preparation of Compound 023

Compound 023-03B (10.00 Kg) and ion exchange resin (1.0 Kg) were added to ethanol (30.0 L) under stirring; temperature was controlled at 55° C., GC (gas chromatography) was carried out to monitor the reaction until the end of the reaction; thereafter the reaction system was filtered, and filtrate was concentrated. The crude product was subjected to column chromatography to give compound 023. Yield: 38%.

Compound 023: $^1$H NMR (400 MHz, DMSO-d$_6$) δ 4.53 (t, J=5.3 Hz, 1H), 3.98 (dqd, J=8.1, 7.0, 3.8 Hz, 4H), 3.50-3.36 (m, 2H), 1.80-1.50 (m, 4H), 1.23 (t, J=7.0 Hz, 6H).

Preparation Example 2

In this example, was prepared Compound 1, which corresponded to process II. Compound 024 and Compound 1-10A were used as starting materials to prepare Compound 1.

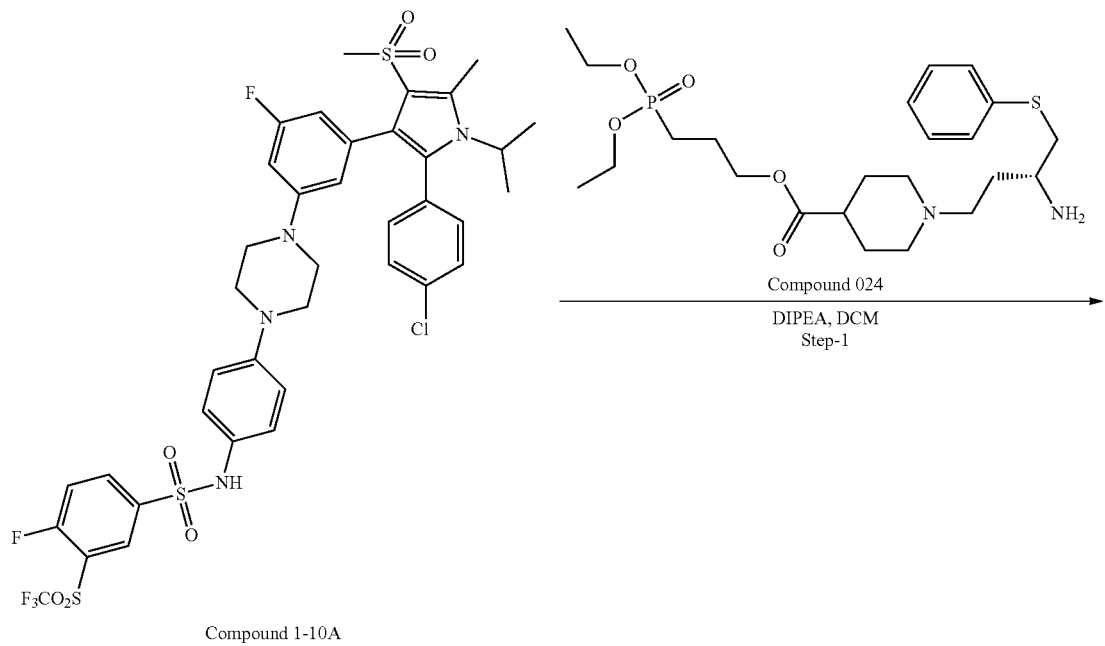
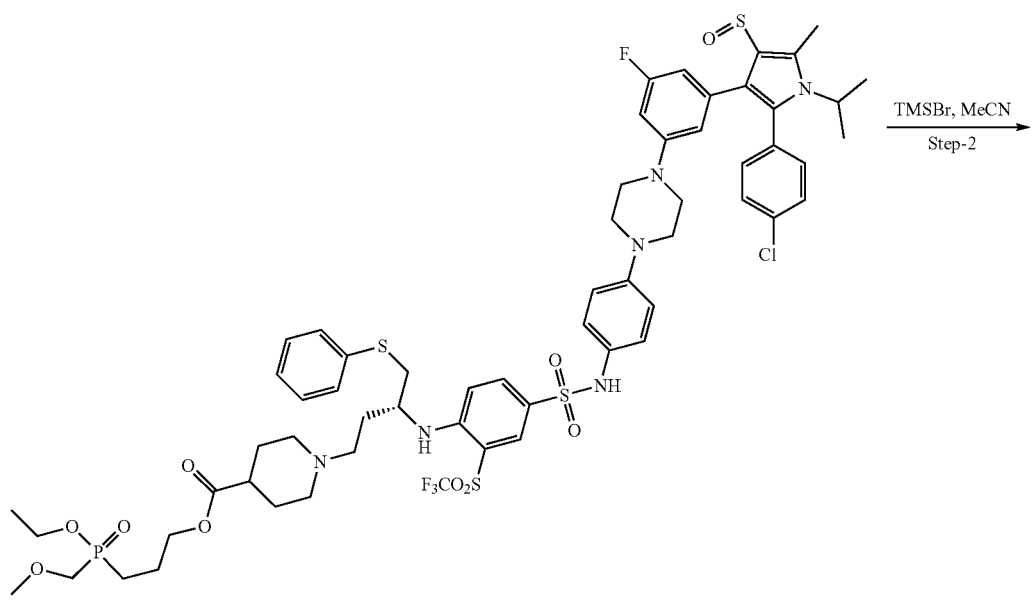

-continued
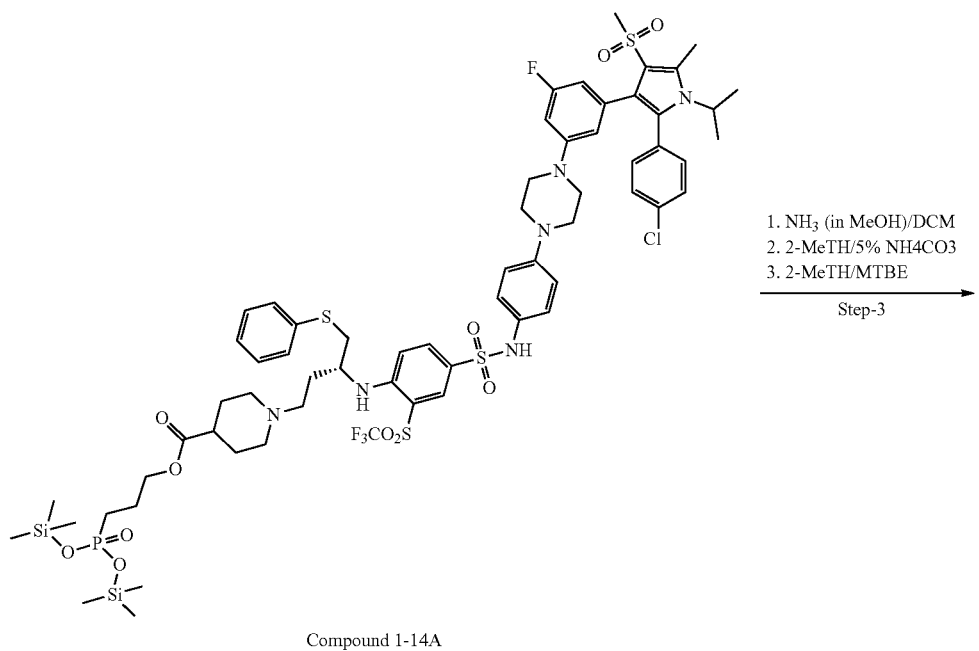
Compound 1-14A
1. NH₃ (in MeOH)/DCM
2. 2-MeTH/5% NH4CO3
3. 2-MeTH/MTBE
Step-3
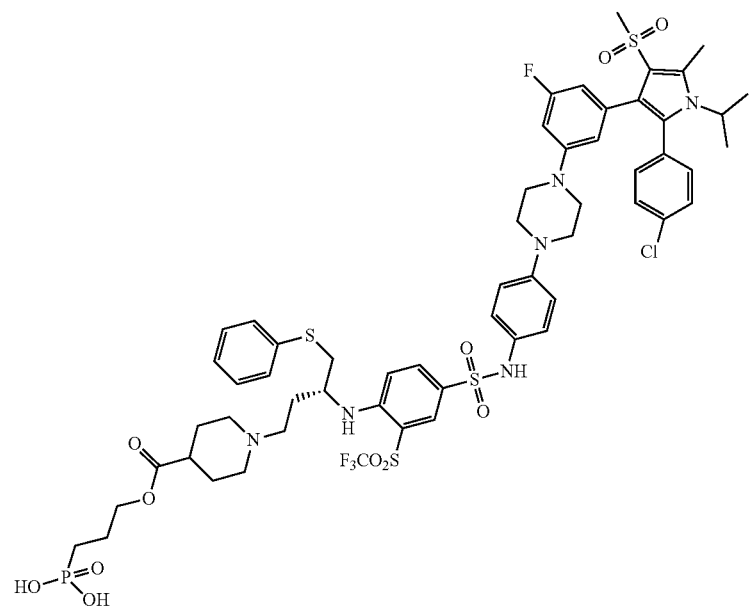
Compound 1

-continued

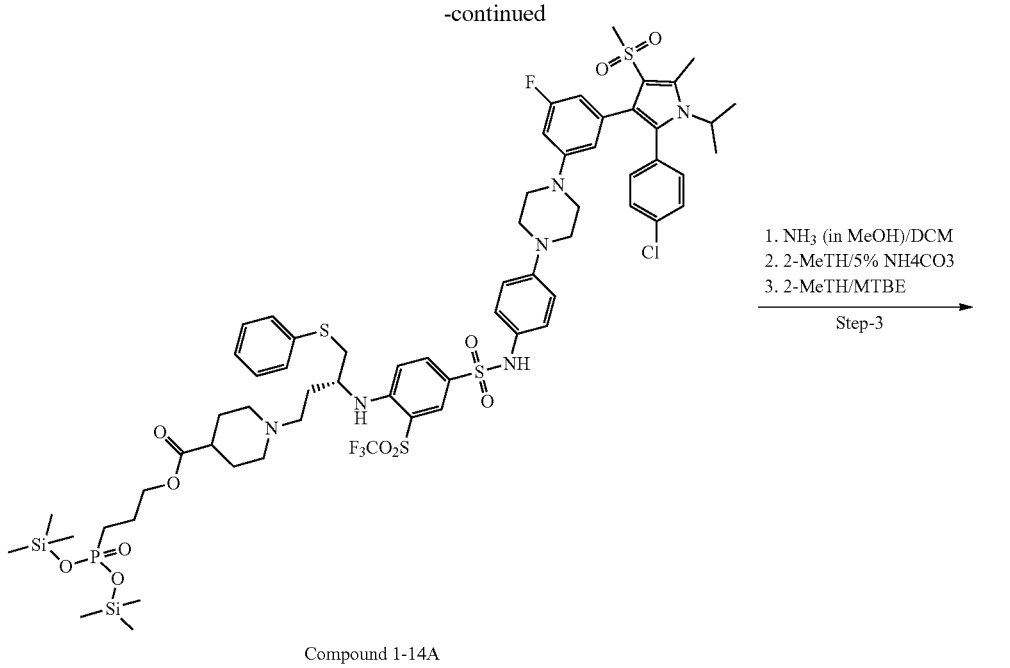

1. NH₃ (in MeOH)/DCM
2. 2-MeTH/5% NH4CO3
3. 2-MeTH/MTBE

Step-3

Compound 1-14A

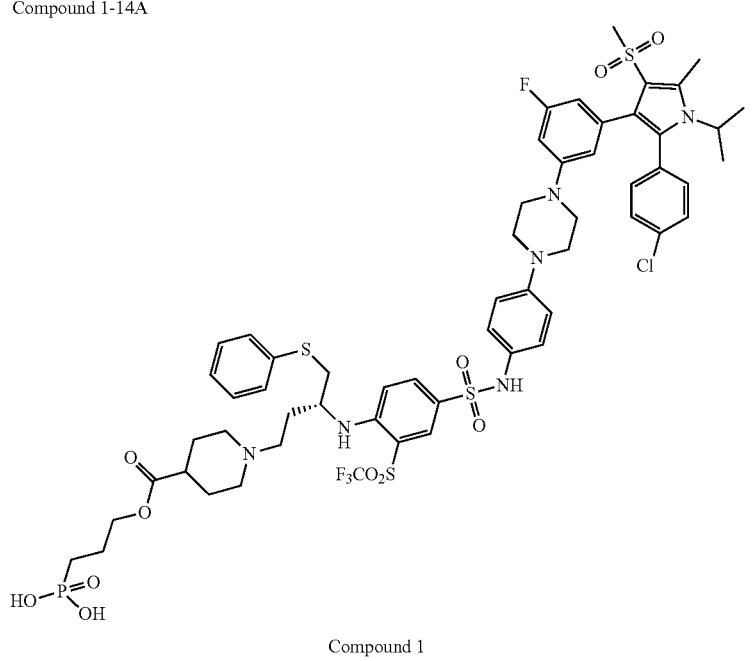

Compound 1

The synthesis process is described as follows:

Step 1: Preparation of Compound 1-13A

Compound 1-10A (1.60 Kg) was added to dichloromethane (32 Kg) under stirring, and compound 024 (1.18 Kg), N,N-diisopropylethylamine (0.70 Kg) was added under protection of nitrogen atmosphere, and the reaction system was stirred at room temperature for 24 hours; IPC was carried out to monitor the reaction until the end of the reaction, thereafter the reaction was stopped, and the reaction system was washed; the organic phase was directly concentrated to dryness; the crude product was purified by column chromatography (dichloromethane/methanol as eluents) to give pale yellow solid compound 1-13A. (Yield: 75%).

Step 2: Preparation of Compound 1-14A

Compound 1-13A (877 g) was added to acetonitrile (7.5 Kg) under stirring, and the reaction system was protected with nitrogen gas; trimethylbromosilane (502 g) was added dropwise rapidly; the temperature was raised to 60±2° C.; and the reaction system was stirred while keeping the same temperature for 60 minutes; IPC was carried out to monitor the reaction until the end of the reaction; thereafter the reaction system was cooled; the reaction solution was concentrated to dryness under reduced pressure; acetonitrile was added and then concentrated to dryness; dichloromethane was added and then concentrated to dryness to give compound 1-14A, Yield: 110%.

Step 3: Preparation of Compound 1

Compound 1-14A (1.02 Kg) was added to dichloromethane (20 Kg) under stirring at room temperature; ammonia-methanol solution (2.0 mol/L) (1.44 Kg) was added dropwise, stirred for 45 minutes; The reaction solution was directly transferred to a rotary evaporator to be concentrated to dryness; the crude product was dissolved in 2-methyltetrahydrofuran (suspension); the organic phase was washed with 5% aqueous ammonium bicarbonate. The organic phase was transferred to a rotary evaporator and concentrated to dryness; 2-methyltetrahydrofuran (8.6 Kg×3) was added to a rotary evaporator and concentrated to dryness; the crude product was dissolved in 2-methyltetrahydrofuran (7.5 Kg); The reaction vessel was purged with nitrogen, and added methyl tert-butyl ether (23 Kg); the above solution of the crude product dissolved in 2-methyltetrahydrofuran was added dropwise to the reaction vessel, stirred for 45 minutes, and filtered; the filter cake was washed with methyl tert-butyl ether, dried in vacuum to give compound 1. Yield 80%.

$^1$H NMR (400 MHz, DMSO-$d_6$) δ 7.79 (d, J=2.1 Hz, 1H), 7.66 (d, J=9.0 Hz, 1H), 7.37 (d, J=8.0 Hz, 2H), 7.30-7.16 (m, 7H), 6.99 (d, J=9.4 Hz, 1H), 6.93 (d, J=8.5 Hz, 2H), 6.86 (t, J=10.9 Hz, 3H), 6.61-6.49 (m, 2H), 6.37 (d, J=9.2 Hz, 1H), 4.33 (p, J=7.0 Hz, 1H), 4.06 (s, 3H), 3.35 (d, J=11.8 Hz, 2H), 3.10 (d, J=20.2 Hz, 8H), 2.89 (s, 4H), 2.67 (s, 4H), 2.38 (d, J=28.3 Hz, 3H), 2.16 (s, 2H), 1.96 (s, 1H), 1.78 (s, 5H), 1.69-1.43 (m, 4H), 1.34 (d, J=7.0 Hz, 6H).

The intermediate compound 1n2 and the intermediate compound 1-08A to which the present invention relates can be synthesized by the following processes:

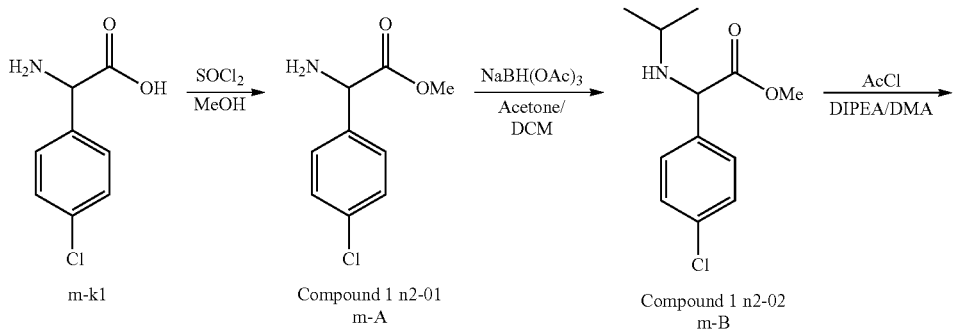

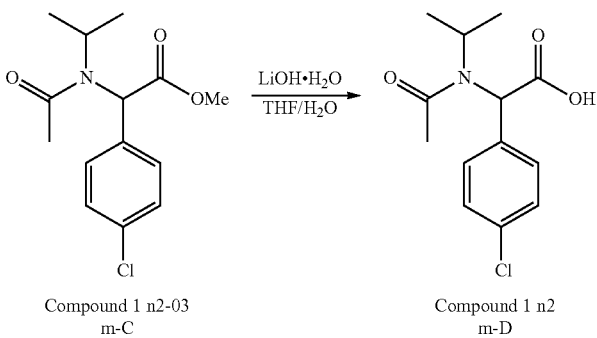

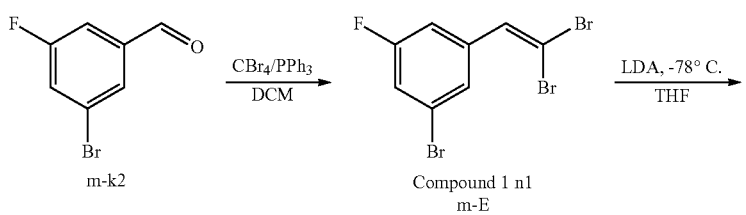

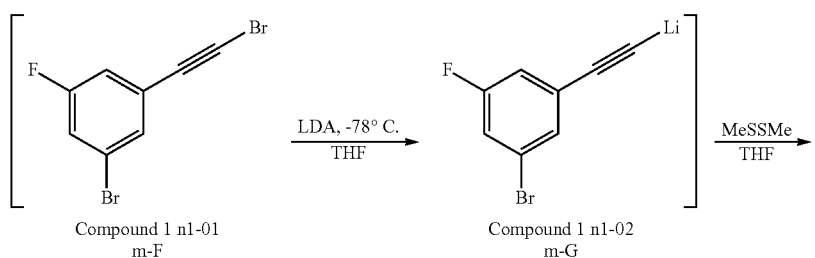

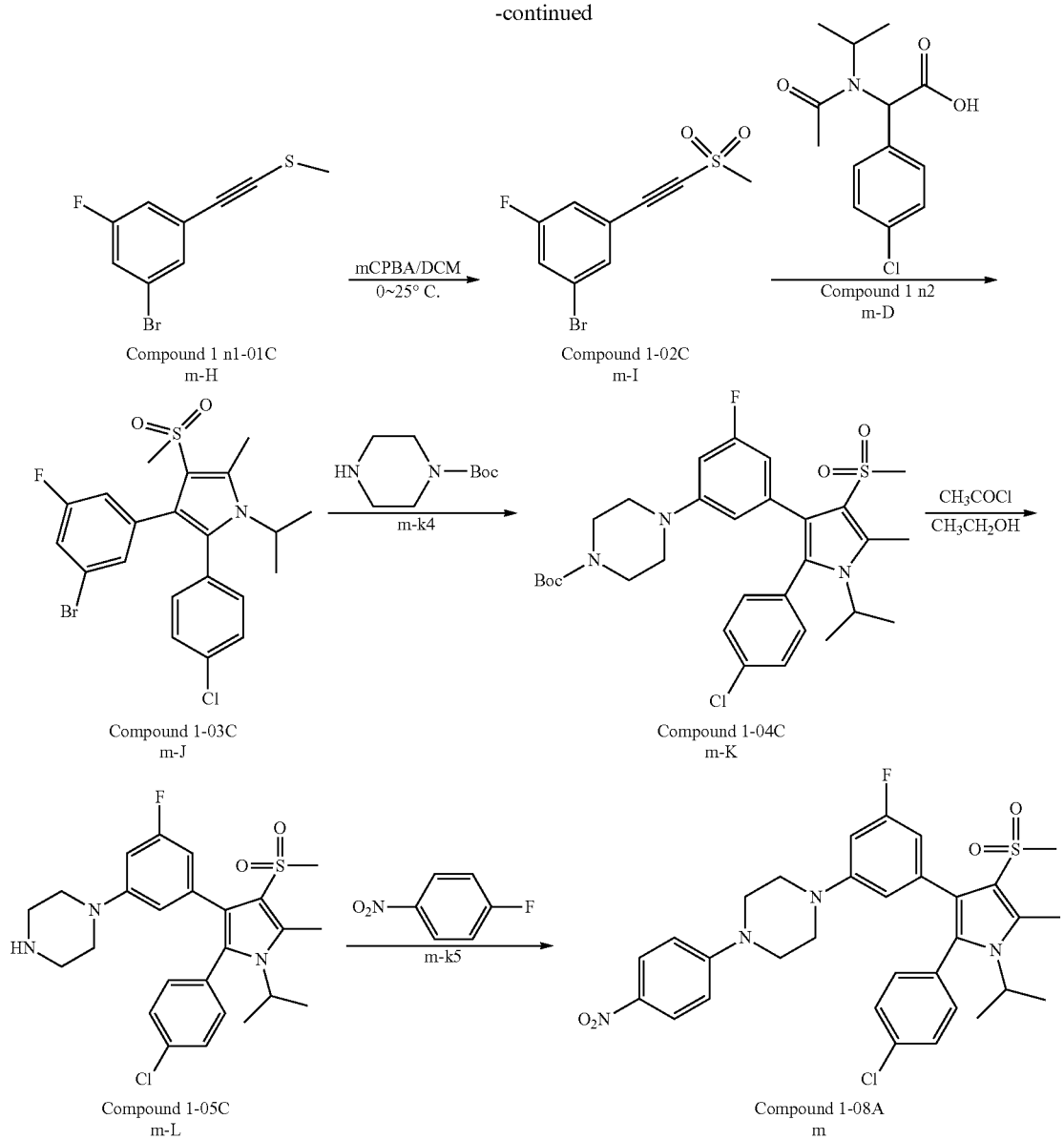

The synthesis process of compound 1n2 is described as follows:

The Step 1: Preparation of Compound 1 n2-01

Under nitrogen protection, p-chlorophenylglycine (300 g) was added to methanol (3.0 Kg); temperature was controlled at 0 to 10° C., thionyl chloride (384 g) was added dropwise; after the addition, the reaction system was heated to 55 to 65° C., stirred while keeping the same temperature for 1 to 2 hours. IPC was carried out to monitor the reaction until the end of the reaction; the reaction solution was directly concentrated to dryness; the crude product was dissolved in dichloromethane (3.2 Kg), basified to pH 7-8 with 8% ammonium bicarbonate solution (4.8 Kg), and allowed to stand to separate into layers; the aqueous phase was extracted with dichloromethane; the organic phase was combined, washed with 25% sodium chloride solution, dried over anhydrous magnesium sulfate, filtered and concentrated; crude compound 1n2-01 was directly used in the next step.

Step 2: Preparation of Compound 1 n2-02

Compound 1n2-01 (323 g) and acetone (112 g) were added to dichloromethane (3.9 Kg) under protection of nitrogen atmosphere at room temperature; sodium triacetoxyborohydride (681 g) was added in portions; reaction was carried out for 16 to 20 hours, IPC was carried out to monitor the reaction until the end of the reaction; thereafter water (2.4 Kg) was added; after the addition, the mixture was stirred for 20 to 40 minutes, and allowed to stand to separate into layers; the organic phase was washed, dried with anhydrous magnesium sulfate, filtered, and concentrated; crude compound 1n2-02 was used directly in the next step of reaction.

Step 3: Preparation of Compound 1n2-03

Compound 1n2-02 (386 g) was added to N,N-dimethylacetamide (3.7 Kg) under nitrogen gas protection; temperature was controlled at 0-10° C., and acetyl chloride (251 g) and diisopropylethylamine (811 g) were added dropwise sequentially; after the addition, the temperature was raised to 35 to 45° C., and the reaction was carried out for 2 to 4 hours. IPC was carried out to monitor the reaction until the end of the reaction; thereafter concentration was carried out; dichloromethane (4.3 Kg) was added to the concentrate; the organic phase was washed, dried over magnesium sulfate, filtered and concentrated; ethyl acetate (448 g), n-heptane (2.38 g) were added to the concentrate, and the mixture was stirred at room temperature for 3 to 5 hours, filtered, and the filter cake was washed, dried in vacuo to give compound 1n2-03. Yield: three-step yield ~90%.

Step 4: Preparation of Compound 1 n2

Compound 1n2-03 (396 g) was added to a mixture of tetrahydrofuran (5.6 Kg) and water (2.1 Kg) under nitrogen atmosphere protection at room temperature; lithium hydroxide monohydrate (170 g) was added in portions; the reaction was carried out for 16 to 18 hours, IPC was carried out to monitor the reaction until the end of the reaction; 1 N hydrochloric acid (3.0 Kg) was added; ethyl acetate (6.8 Kg) was added, and the mixture was stirred for 20 to 40 minutes, and allowed to stand to separate into layers; the aqueous phase was extracted with ethyl acetate; The organic phase was washed with a 25% sodium chloride solution, dried over anhydrous magnesium sulfate, filtered, and the filter cake was washed with n-heptane, dried in vacuum to give compound 1n2.

Yield: ~80%.

The synthesis process of compound 1-08A is described as follows:

The Step 1: Preparation of Compound 1n1

3-bromo-5-fluorobenzaldehyde (400 g) and triphenylphosphine (1.3 Kg) were added to dichloromethane (4.7 Kg) under nitrogen gas protection; temperature was controlled at 0-10° C., a pre-formulated solution of carbon tetrabromide (817 g) in dichloromethane (1.2 Kg) was added dropwise, stirred at room temperature for 2 to 4 hours. IPC was carried out to monitor the reaction until the end of the reaction; 8% sodium hydrogen carbonate solution (2 Kg) was added to the reaction system, and the reaction system was allowed to stand to separate into layers; the organic phase was washed, dried over anhydrous magnesium sulfate, filtered, and the filter cake was washed with n-heptane, filtered and concentrated to give the product which was used directly in the next step of reaction. Yield: 85%.

Step 2: Preparation of Compound 1-01C

Compound 1n1 (270 g) was added to tetrahydrofuran (2.4 Kg) under nitrogen atmosphere protection; the temperature was lowered to −85 to −70° C., and the pre-formulated solution of lithium diisopropylamide (976 g) in tetrahydrofuran (2.0 Kg) was added dropwise. IPC was carried out to monitor the reaction until complete conversion of raw materials; temperature was controlled at −85 to −70° C., a pre-formulated solution of dimethyl disulfide (248 g) in tetrahydrofuran (890 g) was added dropwise; during the addition process, IPC was carried out to monitor intermediate the conversion rate of compound 1n1-01 and compound 1n01-02; 20% ammonium chloride solution (2.0 Kg) was added to the reaction system which was allowed to stand to separate into layers; the aqueous phase was extracted with ethyl acetate (1.35 Kg); the organic phase was combined, washed, dried over magnesium sulfate, filtered, concentrated, and distilled under reduced pressure to give the product. Yield: ~55%.

$^1$H NMR (400 MHz, chloroform-d) δ 7.35 (s, 1H), 7.20 (dt, J=8.3, 2.1 Hz, 1H), 7.08-7.01 (m, 1H), 2.51 (s, 3H).

Step 3: Preparation of Compound 1-02C

Compound 1-01C (212 g) was added to dichloromethane (2.6 Kg) under nitrogen gas protection. The temperature was controlled at 0 to 10° C., and a pre-formed solution of metachloroperbenzoic acid (522 g) in dichloromethane (9.8 Kg) was added dropwise, stirred at room temperature for 2 to 3 hours. IPC was carried out to monitor the reaction until the end of the reaction; the mixture was filtered, and the filter cake was washed with dichloromethane; A 10% sodium thiosulfate solution (3.7 Kg) was slowly added to the filtrate, and the mixture was allowed to stand to separate into layers; the organic phase was washed, dried over anhydrous magnesium sulfate, filtered and concentrated to give a crude product. Yield: ~100%. The nuclear magnetic data of compound 1-02C is as follows:

$^1$H NMR (400 MHz, chloroform-d) δ 7.59-7.55 (m, 1H), 7.45 (ddd, J=8.0, 2.4, 1.7 Hz, 1H), 7.30-7.25 (m, 1H), 3.33 (s, 3H).

Step 4: Preparation of Compound 1-03C

Under the protection of nitrogen gas, compound 1-02C (207 g) and compound 1 n2 (242 g) were added to acetic anhydride (3.8 Kg); the mixture was controlled at 100-110° C., stirred for 2-3 hours. IPC was carried out to monitor the reaction until the end of the reaction; the temperature was lowered to 50-60° C., and the reaction solution was directly concentrated to dryness; the crude product was dissolved in ethyl acetate (4.1 Kg), washed, dried over anhydrous magnesium sulfate, filtered; the filter cake was washed, and dried in vacuo to give compound 1-03C. Yield: ~95%.

Step 5: Preparation of Compound 1-04C

Under nitrogen gas protection, R-BINAP (1.5 g) and Pd(OAc)$_2$ (0.15 g) were added to toluene (348 g); after the addition, the mixture was warmed to 50° C. and stirred for 0.5 hour; compound 1-03C (20 g), Boc-piperazine (7.7 g), water (1.0 g), sodium tert-butoxide (6.0 g) was added in sequence; after the addition, the mixture was warmed to 100 to 110° C., heated to reflux for 3 to 5 hours. IPC was carried out to monitor the reaction until the end of the reaction; 20% ammonium chloride solution (200 g), activated carbon (20 g) was added, stirred for 0.5 hour; filtered, and the filtrate was allowed to stand to separate into layers; the organic phase was washed, filtered; the filter cake was washed, and dried in vacuo to obtain compound 1-04C. Yield: ~75%.

The nuclear magnetic data of compound 1-04C is as follows:

$^1$H NMR (400 MHz, chloroform-d) δ 7.27 (d, J=8.2 Hz, 2H), 7.07 (d, J=8.2 Hz, 2H), 6.65 (t, J=1.8 Hz, 1H), 6.40 (dt, J=11.9, 2.4 Hz, 1H), 6.35-6.25 (m, 1H), 4.38 (h, J=7.1 Hz, 1H), 3.51 (t, J=5.1 Hz, 4H), 3.04 (t, J=5.2 Hz, 4H), 2.75 (d, J=9.0 Hz, 6H), 1.45 (d, J=16.0 Hz, 15H).

Step 6: Preparation of Compound 1-05C

Compound 1-04C (17 g) was added to a mixed solution of dichloromethane (157 g) and absolute ethanol (94 g) under nitrogen atmosphere protection; temperature was controlled at 0-10° C., acetyl chloride (23 g) was added; after the addition, the mixture was warmed to room temperature, stirred for 4 to 6 hours. IPC was carried out to monitor the reaction until the end of the reaction; activated carbon (1.7 g) was added to the mixture which was stirred for 1-2 hours, filtered, concentrated; isopropanol (80 g) was added to the mixture; and the mixture was warmed to 55-65° C., stirred for 1-3 hours, cooled to room temperature for crystallization, filtered, and the filter cake was washed, dried in vacuum to obtain compound 1-05C. Yield: ~95%.

The nuclear magnetic data of compound 1-05C is as follows:

$^1$H NMR (400 MHz, chloroform-d) δ 9.57 (s, 1H), 7.28 (d, J=8.2 Hz, 2H), 7.07 (d, J=8.1 Hz, 2H), 6.72 (s, 1H), 6.42

(d, J=11.3 Hz, 1H), 6.30 (d, J=8.9 Hz, 1H), 4.39 (p, J=7.1 Hz, 1H), 3.61-3.17 (m, 8H), 2.74 (d, J=7.7 Hz, 6H), 1.44 (d, J=7.1 Hz, 6H).

Step 7: Preparation of Compound 1-08A

Under the protection of nitrogen gas, compound 1-05C (14 g), 4-nitrofluorobenzene (4.5 g) and potassium carbonate (11 g) were added to dimethyl sulfoxide (154 g) in sequence; temperature was controlled at 55-65° C., the mixture was stirred for 4 to 6 hours. IPC was carried out to monitor the reaction until the end of the reaction; activated carbon (1.4 g) was added; temperature was controlled at 55 to 65° C., the mixture was stirred for 1-2 hours, filtered, and the filter cake was washed with dimethyl sulfoxide; water (77 g) was added to the filtrate at room temperature; after the addition, the mixture was stirred for 1-3 hours, filtered; the wet product was dissolved in dichloromethane and washed; the organic phase was directly concentrated to dryness; ethyl acetate (25 g) and n-heptane (57 g) were added to the crude product which was controlled at the temperature of 55 to 65° C., stirred for 1-3 hours, cooled to room temperature for crystallization for 1-2 hours, filtered, and the filter cake was washed, dried in vacuo to give Compound 1-08A. Yield: 85%.

Synthesis of Compound 1-10A

The synthesis process is described as follows:

Step 1: Preparation of Compound 1-09A

Compound 1-08A (1.6 Kg) and iron powder (0.7 Kg) were added to ethanol (6.6 Kg) under stirring; a pre-formulated aqueous solution of ammonium chloride (2.1 Kg) was added to the reaction vessel; the mixture was heated to reflux overnight, and cooled to 40±2° C., dichloromethane (8.2 Kg) was added, and the mixture was stirred for 0.5 hour, filtered, and the filter cake was washed with dichloromethane; the filtrate was combined, and concentrated under reduced pressure in portions to remove most of the organic solvent, filtered, and the filter cake was washed with ethanol, dried under vacuum at 35±2° C. to obtain compound 1-09A, yield: 93%.

Step 2: Preparation of Compound 1-10A

Compound 011 (1.6 Kg) was added to dichloromethane (14.7 Kg) under stirring at room temperature; under nitrogen gas protection, triethylamine hydrochloride (1.0 Kg) was added; Compound 1-09A (1.4 Kg) dissolved in dichloromethane (27.8 Kg) was added into the reaction system dropwise; after the addition was completed, the mixture was stirred while keeping the same temperature for 1.0 hour, refluxed for 10 hours; the organic phase was washed, filtered and concentrated; the crude product was dissolved in ethyl

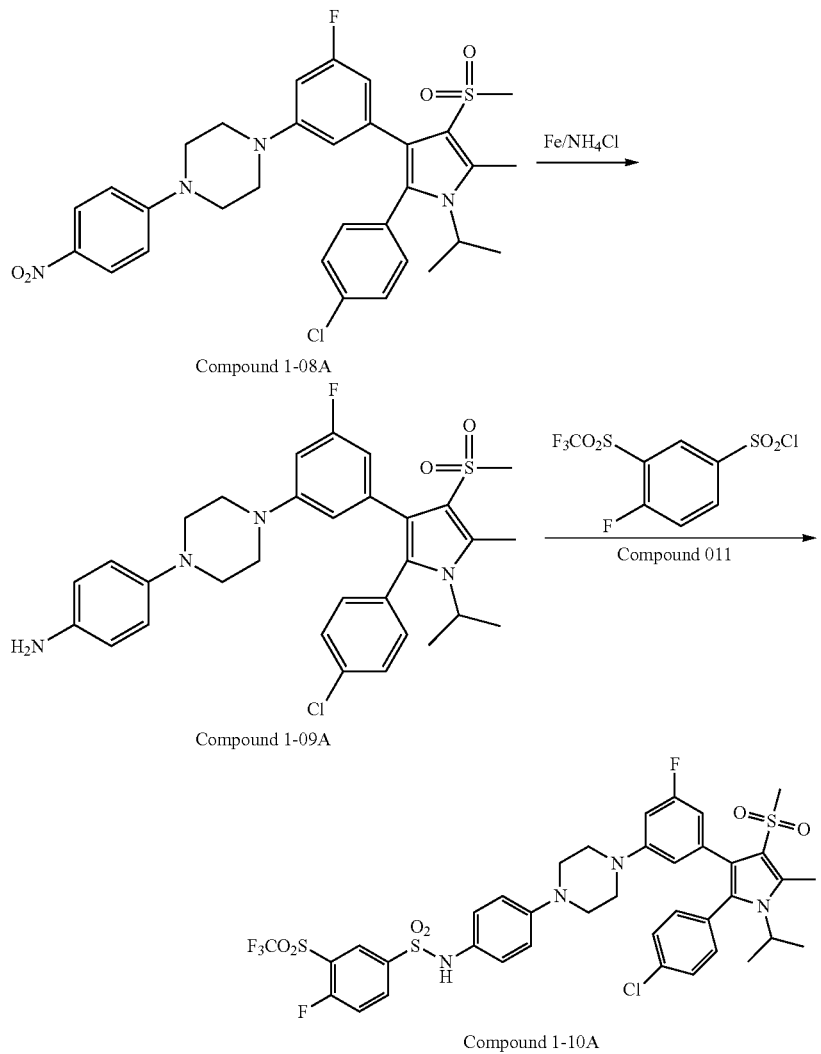

acetate (3.2 Kg), subjected to silica gel flash column eluted with ethyl acetate 5 times, the ethyl acetate eluate was concentrated to dryness; the solid was dissolved in dichloromethane (9.8 Kg), the temperature was controlled at 35±2° C., the solid was dissolved to obtain a clear solution to which was added n-heptane (5.1 Kg) dropwise to precipitate solid and stirred for 0.5 hour; the solution was cooled to room temperature, filtered and the filter cake was washed, dried in vacuo to give compound 1-10A, yield: 91%.

$^1$H NMR (400 MHz, DMSO-$d_6$) δ 10.12 (s, 1H), 8.33-8.11 (m, 2H), 7.99-7.78 (m, 1H), 7.38 (d, J=8.5 Hz, 2H), 7.28 (d, J=8.1 Hz, 2H), 7.01-6.65 (m, 4H), 6.63-6.45 (m, 2H), 6.43-6.29 (m, 1H), 4.33 (p, J=7.1 Hz, 1H), 3.13 (q, J=5.9 Hz, 8H), 2.90 (s, 3H), 2.67 (s, 3H), 1.35 (d, J=6.9 Hz, 6H).

The intermediate compound 024-01 of the present invention can be synthesized by the following process:

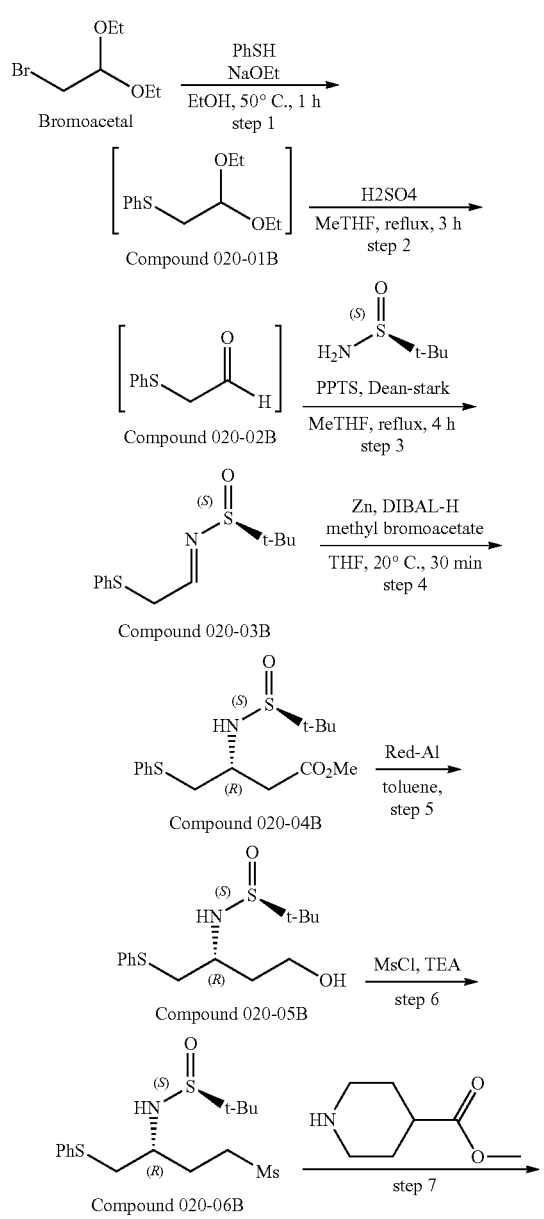

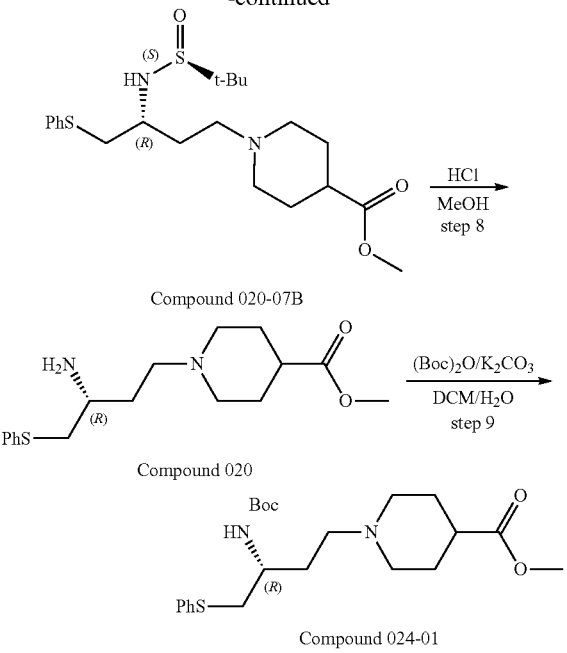

Step 1: Preparation of Compound 020-01B

Sodium ethoxide (41.05 kg) was added to ethanol (165.5 kg) solution, and the liberation of heat was significant. The solution was cooled to room temperature, thiophenol (66.98 kg) was added, then the solution was heated to 50-55 degrees, and bromoacetal (100 kg) was added dropwise. After the addition, the mixture was heated and refluxed for 1 hour. TLC was used to test the sample (petroleum ether: ethyl acetate=50:1), the reaction was basically completed, and the reaction solution was cooled to 15-20 degrees and water (149.6 Kg) was added. After completion of the addition, the ethanol was distilled off under reduced pressure (water bath temperature 50-55 degrees), evaporated to dryness, then methyltetrahydrofuran (161.05 Kg) was added, the mixture was stirred for 30 minutes, and a liquid separating operation was carried out. The organic phase was directly used in the next step.

Step 2: Preparation of Compound 020-02B

Concentrated sulfuric acid (50.15 kg) was added to water (600.65 kg), and the solution containing compound 020-01B in methyltetrahydrofuran was added dropwise. After the addition, the mixture was heated to reflux and kept at the same temperature for 2 hours. TLC was carried out for detection, and the reaction was basically completed. The reaction was allowed to stand to separate into layers, and the upper organic phase was used directly in the next step.

Step 3: Preparation of Compound 020-03B

Pyridinium p-toluenesulfonate salt (20 Kg) was added to methyltetrahydrofuran (75 Kg), S-tert-butylsulfinamide (60 Kg) was added, and the mixture was stirred for 30 minutes. A solution of the compound 020-02B in methyltetrahydrofuran (300 L) was added dropwise. After the addition, the mixture was warmed to 80-85 degrees and refluxed for more than 5 hours. TLC was carried out for detection, and the reaction was completed. The reaction was cooled to room temperature, water (100 kg) and toluene (87 kg) was added, the reaction was stirred for 30 minutes. A liquid separating operation was carried out, and the organic phase was washed, dried over the anhydrous sodium sulfate, filtered, and the mother liquid was concentrated under reduced pressure to give 101.5 kg Compound 020-4 as a crude product (Yield 78%).

Step 4: Preparation of Compound 020-04B

Under nitrogen gas protection, zinc powder (77.87 kg) was added to tetrahydrofuran (200 kg), the system was heated to 30-35 degrees, methyl bromoacetate (6.03 kg) was added dropwise, and lithium diisobutyl hydride (35.16 L) was added dropwise after the addition. The mixture was heated up to 50-55 degrees, methyl bromoacetate (96.96 kg) was added, and the mixture was kept at 50-55 degrees for more than 1 hour. The mixture was cooled to room temperature, and solution of compound 020-03B (100.05 kg) in tetrahydrofuran (100 kg) was added dropwise. The mixture was stirred for 1 hour after the addition. TLC was carried out for detection, and the reaction was basically completed. 25% brine (30 kg), 10% citric acid aqueous solution (320 kg) and 25% brine (163 kg) was added dropwise in sequence, toluene (180 kg) was added, and the mixture was stirred for 30 minutes. The aqueous phase was separated, and extracted with toluene, and the organic phase was combined, and concentrated to dryness under reduced pressure. The crude product was subjected to column chromatography, n-hexane:ethyl acetate=4:1 to 3; 1, and the mother liquor of the product was collected, and concentrated under reduced pressure to dryness to give compound 020-5 (55.8 kg) yield 42%.

Step 5: Preparation of Compound 020-05B

Toluene (290 Kg) and red aluminum (77 L) were added to the reaction vessel, and the mixture was cooled to 0-5 degrees under nitrogen atmosphere protection, and a solution of compound 020-04B (55 Kg) in toluene (100 Kg) was added dropwise, and the mixture was stirred for 30 minutes after completion of the dropwise addition, then warmed to room temperature and stirred for 1 hour. TLC was carried out for detection, and the reaction was completed. 10% NaOH aqueous solution was added, and stirred for 1 hour. the aqueous phase was extracted with toluene, the organic phases was combined, washed, dried by addition of anhydrous sodium sulfate, filtered, and the mother liquor was used directly in the next step.

Step 6: Preparation of Compound 020-06B

Toluene solution (about 600 L) containing compound 020-05B was added to TEA (33.66 Kg), and the mixture was cooled to 0 degree under nitrogen gas protection. Methylsulfonyl chloride (28.66 Kg) was added dropwise, and the mixture was stirred for 1 hour. TLC was carried out for detection, and the reaction was completed. To the organic phase was added water (200 kg), and the mixture was stirred for half an hour. A liquid separating operation was carried out, and the mixture was washed by addition of saturated brine. To the organic phase was added sodium sulfate for drying, the mixture was filtered, and the mother solution (600 L) containing compound 020-06B was used directly in the next step.

Step 7: Preparation of Compound 020-07B

To a toluene solution (600 L) containing compound 020-06B was added potassium carbonate (69.02 Kg) and methyl piperidine-4-carboxylate (35.75 Kg), and the mixture was stirred at room temperature overnight. To the organic phase was added water (300 Kg), and the mixture was stirred for half an hour. A liquid separating operation was carried out. The organic phase was washed by addition of water, and the organic phase was evaporated to dryness under reduced pressure, and then subjected to column chromatography (the column was eluted by hexane:ethyl acetate=3:1) to give compound 020-07B (25.55 kg, 36%).

Step 8: Preparation of Compound 020

Methanol (45 Kg) and compound 020-07B (25 Kg) were added to the reaction vessel. 1.5 N hydrochloric acid in methanol (117 L) was added at room temperature, and the mixture was stirred for 1 hour. TLC was carried out for monitoring. After completion of the reaction, the reaction was concentrated to dryness under reduced pressure. Water (100 kg) and ethyl acetate (150 kg) were added, the pH was adjusted to 9-10, and a liquid separating operation was carried out. The aqueous phase was extracted with ethyl acetate. The organic phase was combined and was stirred and dried over anhydrous sodium sulfate. The organic phase was filtered and evaporated under reduced pressure to give compound 020 as a crude product (12.5 kg, 66%).

The crude compound 020 was added to acetone (122 Kg), and L-di-p-methylbenzoyltartaric acid (24.85 Kg) was added at room temperature, and the mixture was stirred at room temperature for 1 hour, filtered, rinsed with a small amount of acetone, and dried (40-45 degrees) to obtain salts. Water (100 Kg) was added, and the pH was adjusted to 9-10 at room temperature. The aqueous phase was extracted with ethyl acetate. The organic phase was combined and was stirred and dried over anhydrous sodium sulfate. The organic phase was filtered and evaporated to dryness under reduced pressure to give 8.75 kg of Compound 020 (71%).

Step 9: Preparation of Compound 024-01

Potassium carbonate (4.88 Kg) and water (22 Kg) were added to the reaction vessel, the mixture was stirred to obtain a clear solution to which were added dichloromethane (29 Kg) and compound 020 (8.7 Kg). BOC-anhydride: (Boc)2O (5.89 Kg) was added at room temperature. After the addition, the mixture was stirred for 1 hour. TLC was carried out for monitoring. After the completion of the reaction, the reaction was allowed to stand to separate into layers. The aqueous phase was extracted with dichloromethane (20 Kg), and the organic phases were combined, washed with water. The organic phase was stirred and dried over anhydrous sodium sulfate. The organic phase was filtered, and evaporated to dryness under reduced pressure. Tetrahydrofuran was added and the mixture was evaporated to dryness under reduced pressure again to give compound 024-01 (10.27 kg, 90%).

$^1$H NMR (400 MHz, DMSO-$d_6$) δ 7.42-7.24 (m, 4H), 7.21-7.10 (m, 1H), 6.90 (d, J=8.4 Hz, 1H), 3.60 (s, 4H), 3.11-2.92 (m, 2H), 2.76 (s, 2H), 2.37-2.19 (m, 3H), 1.91 (s, 2H), 1.82-1.45 (m, 6H), 1.37 (s, 9H).

The intermediate compound 024-01 of the present invention can also be synthesized by the following process:

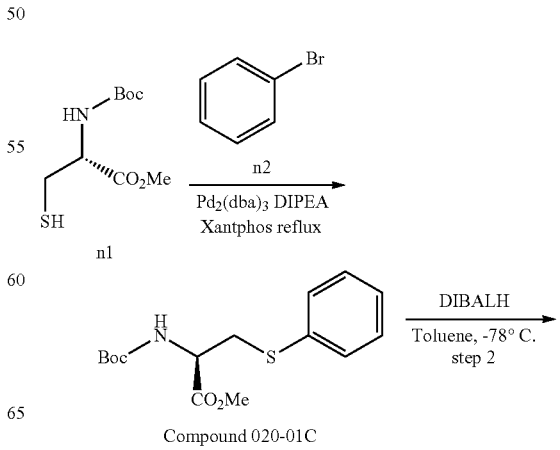

Compound 020-01C

85

-continued

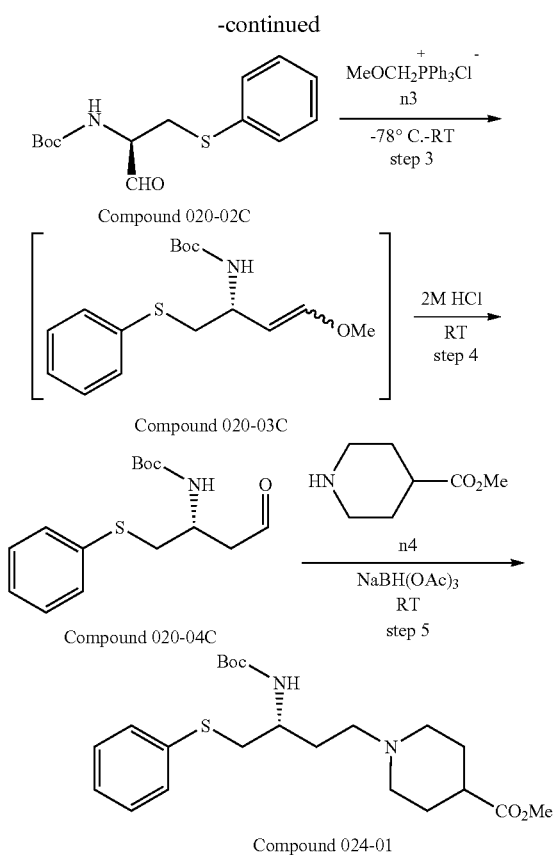

Step 1: Preparation of Compound 020-01C

N-Boc cysteine methyl ester 30 g, bromobenzene 24.02 g, pd$_2$(dba)$_3$ (tris(dibenzylideneacetone) dipalladium) 5.80 g, xantphos (9,9-Dimethyl-4,5-bis(diphenylphosphino)xanthene) 7.38 g, DIPEA 49.4 g, 1,4-dioxane 400 ml were added to the flask which was evacuated, purged with nitrogen, warmed to 90 degree for reaction. TLC was carried out for monitoring. After raw materials were completely reacted, the reaction was cooled to room temperature, and 300 ml of H$_2$O was added thereto. The reaction was stirred, filtered, and the filtrate was extracted twice with DCM 150 ML. The organic phases were combined and washed with saturated sodium chloride and dried over anhydrous magnesium sulfate. Filtration and concentration of the filtrate under reduced pressure afforded 66.5 g of crude product. Column chromatography gave pure product (31.6 g) yield 79%.

Step 2: Preparation of Compound 020-02C 5 g of compound 020-01C (1 eq) and 100 ml of toluene were added to the flask which was cooled to −78° C., thereafter 32.1 ml of a 1.5 M DIBALH in toluene was added dropwise. After the addition was completed, the TLC monitoring was carried out to find out that the reaction was complete, then addition of 20 ml of anhydrous methanol was added dropwise at −78° C. to quench the reaction. The reaction was stirred for 30 min, warmed to room temperature, filtered over celite, and filtration and concentration of the filtrate under reduced pressure afforded 3.87 g of oil, which was directly used in the next step.

Step 3: Preparation of Compound 020-03C 7.32 g of compound n3 (2.0 eq), THF (60 ml) were added to the flask to which the evacuation and breaking of the vacuum with nitrogen were carried out three times, and the temperature was lowered to −78° C. 26.7 ml of 1 M

86

(Me$_3$Si)$_2$ NK was added dropwise, (2.5 eq). After the completion of the addition, the mixture was stirred for 30 min, warmed slowly to 0° C., and 3.0 g of crude compound 020-02C in THF (30 ml) was added dropwise. After the completion of the addition, the reaction was stirred at 0° C. TLC monitoring found out that there are no raw material remained in the reaction, water was added to quench the reaction which was extracted with EA (40 ml×3), washed with saturated brine, dried over magnesium sulfate, filtered, and concentration and column chromatography of the filtrate gave 0.5 g of the desired product, with two-step yield of 10%.

Step 4: Preparation of Compound 020-04C 0.35 g of compound 020-03C (1.0 eq), 7 ml of acetone (20 v) were added to the flask. The mixture was stirred at room temperature, and 0.85 ml of 2N HCl (1.5 eq) was added dropwise thereto. The reaction was monitored by TLC, and the reaction was completed in about 2.5 hours, and then pH was adjusted to 7 with saturated sodium bicarbonate. The mixture was extracted with EA (20 ml×3), washed with saturated sodium chloride, dried over magnesium sulfate, filtered, and the filtrate was concentrated and dried to obtain 0.33 g of an oily substance (yield 100%).

Step 5: Preparation of Compound 024-01

To a 50 ml three-necked flask, was added 0.30 g of compound 020-04C, and 7.5 ml of DCM, and the mixture was stirred to obtain a solution. 0.17 g of compound n4 (1.2 eq) was added, and the mixture was stirred at room temperature for 1 h, and then 0.43 g of sodium triacetoxyborohydride (2.0 eq) was added for a reaction at room temperature overnight. After TLC monitored that the reaction was complete, the reaction was quenched with water, a liquid separating operation was carried out. The aqueous phase was extracted with DCM, washed with saturated brine and dried over magnesium sulfate, and filtration of the aqueous phase gave 0.5 g of oil which was subjected to column chromatography (DCM:MEOH=100:1) to give 0.35 g of the desired product (yield 82%, purity 99%, ee 99.5%).

The intermediate compound 024-k according to the present invention can be synthesized by the following process:

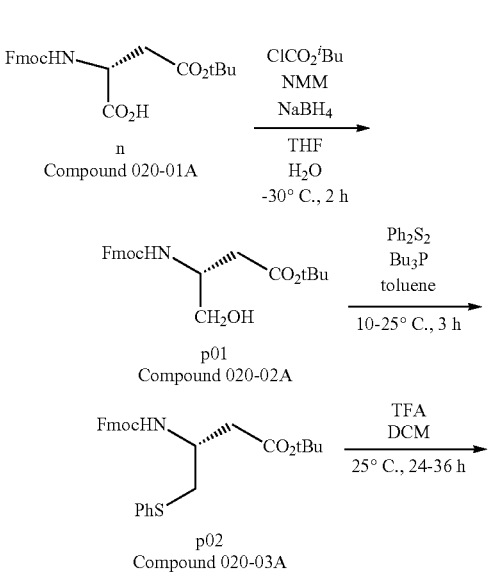

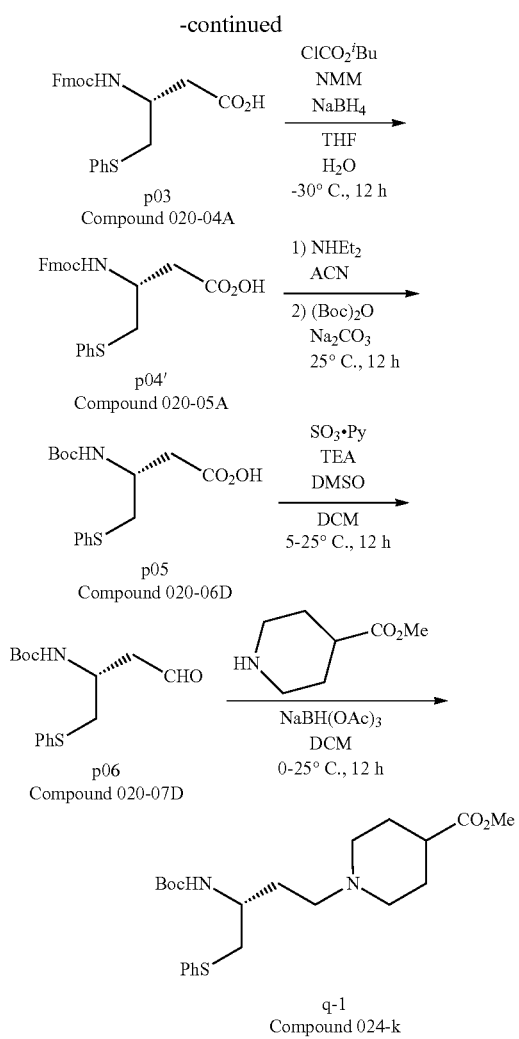

Preparation of Compound 020-02A

Compound 020-01A (3000 g) and NMM (885 g) were added to THF (9 L) to obtain a solution 1. THF (19 L) was added to the reaction kettle, and ClCOOiBu (1195 g) was added under stirring. The reaction system was cooled to −35° C., and the solution 1 was added dropwise; after the end of the addition, the reaction was carried out at −40° C. for 1 h, filtered under reduced pressure, and the filter cake was washed with THF. The filtrate was ready to use; THF (11 L) was added to another reactor kettle, and stirred. The temperature was lowered to −40° C. by dry ice-ethanol, and a mixed solution of sodium borohydride (522 g) and water (5.5 L) was added. The above filtrate was added dropwise at −35 degrees, and the temperature was controlled at −40 to −30 degrees with a large amount of gas produced. After completion of the addition of the feeds, the mixture was stirred for 1 h; after confirming that the reaction was complete, the temperature was lowered to −45° C., a pre-formulated solution of 2 kg of ammonium chloride and 10 L of water are added, and the reaction was quenched. The reaction system was separated to obtain the organic phase which was concentrated to obtain yellow oil, and n-heptane was added. The mixture was concentrated, dried to give 8.6 kg of white solid, yield 88%, purity 97.62%.

Preparation of Compounds 020-03A and 04A

Toluene (12 L) was added to the reaction kettle, and compound 020-02A (25.3 Kg), and Ph2S2 (22.5 kg, 14.5 mol, 1.6 eq) were added under stirring, the mixture was cooled to −5° C.; Bu3P (24 kg, 117.76 Mol, 1.85 eq) was added dropwise, and the reaction was carried out for 7 h. The reaction mixture was poured into ice water and quenched, extracted with DCM. The organic phase was separated, and transferred to another reactor kettle. TFA (40 L) was added, and the inner temperature was raised to the room temperature. The reaction was carried out for 36 h, and TFA (20 L) was added for the reaction. After the completion of the reaction was monitored, water (150 L) was added, and the aqueous phase was separated. The aqueous phase was extracted with DCM, and the organic phase was combined, n-heptane was added, and a solid was precipitated and dried to give 24.7 g of white solid, the yield in two steps was 88%.

Preparation of Compound 020-05A

Compound 020-04A (24.7 Kg), THF (72 L) and NMM (8.1 Kg) were added to the glass kettle to obtain solution 1; THF (180 L) was added to a 1000 L stainless steel reaction kettle and ClCOOiBu (10.8 Kg) was added under stirring. The mixture was cooled to −35° C., and solution 1 was added; after the end of the addition, reaction was carried out at −30° C. for 1 h; the reaction was filtered under reduced pressure to obtain filtrate 1; THF was added to the stainless steel reaction kettle, the mixture was cooled to −50 degree by liquid nitrogen under stirring. A mixed solution of sodium borohydride (4200 g) and water (40 L) were added. The above filtrate was added dropwise at −50 degree. After the addition was complete, sodium borohydride (2600 g) was added and a large amount of gas was released, and the mixture's temperature increased naturally up to room temperature; IPC detection showed that reaction was complete. Ammonium chloride aqueous solution was added to quench the reaction, water and EA were added for extraction and a liquid separating operation. To the organic phase was added n-heptane, the mixture was filtered. The obtained solid was dried to obtain 22 kg of white solid, yield 92%.

Preparation of Compound 020-06D

To the glass kettle were added 020-05A (22 Kg), ACN (60 L) and diethylamine (60 L), and the mixture was stirred for 12 hours; acetonitrile and diethylamine were removed by rotary evaporation and desolvation; the residue was transferred to the extraction kettle. water and dichloromethane were added, the mixture was stirred, and the pH was adjusted to 1 with hydrochloric acid. the organic phase was separated, extracted with water to obtain an aqueous phase which pH was adjusted to 7-8 with 5% NaOH solution. sodium carbonate was added, and the system was rendered alkaline, and cooled to 10 degree, water and THF were added, and (BOC)2O (12.5 kg, 57.2 mol, 1.1 eq) was added, the mixture was stirred naturally for 12 hours; water and EA were added. To the organic phase was add n-heptane. The solid precipitated was dried to give 10 kg of a white solid with yield of 64%.

Preparation of Compound 020-07D

Compound 020-06D (10.0 Kg), DMSO (13.13 Kg) and triethylamine (17.01 Kg) were added to the glass kettle; the mixture was cooled to below 20 degree. Pyridine sulfur trioxide (16.05 Kg) was added, the mixture was stirred at room temperature. After the end of the reaction monitored by HPLC, ice water was added and the mixture was stirred to quench the reaction. The organic phase was extracted and separated. The organic phase was washed with water and concentrated to obtain 11.4 kg of brown oil with a crude yield of 114%.

Preparation of Compound 024-k

Compound 020-07D (11.4 Kg), DCM (35 L) and methyl piperidine-4-carboxylate (5.29 Kg) were added to the glass kettle; the temperature was lowered to below 5 degree, and sodium triacetoxyborohydride (16.4 Kg) was added. The mixture was stirred for 12 hours, and methyl piperidine-4-carboxylate (200 g, 1.39 mol, 0.03 eq), sodium triacetoxyborohydride (600 g, 2.68 mol, 0.06 eq) were added. After the end of the reaction monitored by IPC, ice water was added under stirring to quench the reaction. The mixture was extracted to separate organic phase which was concentrated to give 14.8 kg of brown oil. The crude product yield was 100.3%. 14.8 kg of the above crude product and acetone were added to the glass kettle, the mixture was heated to 40-50 degrees. Anhydrous oxalic acid (3110 g, 34.55 mol, 1 eq) was added, the mixture was stirred at 40-50 degrees for 2 h, and a white solid was precipitated. The solid was filtered off with suction, and the obtained solid was dried to obtain 10 kg of white powder, yield 56%.

The analytical data of compound 024-k is as follows:

1H NMR (400 MHz, DMSO-d6) δ 7.33 (dt, J=15.1, 7.4 Hz, 4H), 7.25-7.13 (m, 1H), 6.99 (d, J=8.5 Hz, 1H), 3.63 (s, 4H), 3.29 (s, 2H), 3.15-2.75 (m, 6H), 2.63 (s, 1H), 2.00 (d, J=11.7 Hz, 3H), 1.93-1.67 (m, 3H), 1.38 (s, 9H). 13C NMR (101 MHz, DMSO-d6) δ 173.98, 164.96, 129.50, 128.73, 126.23, 78.47, 53.64, 52.22, 51.08, 50.85, 48.54, 38.01, 37.68, 28.65, 28.40, 28.25, 25.52.

The intermediate compound 024 of the present invention can be synthesized by the following process:

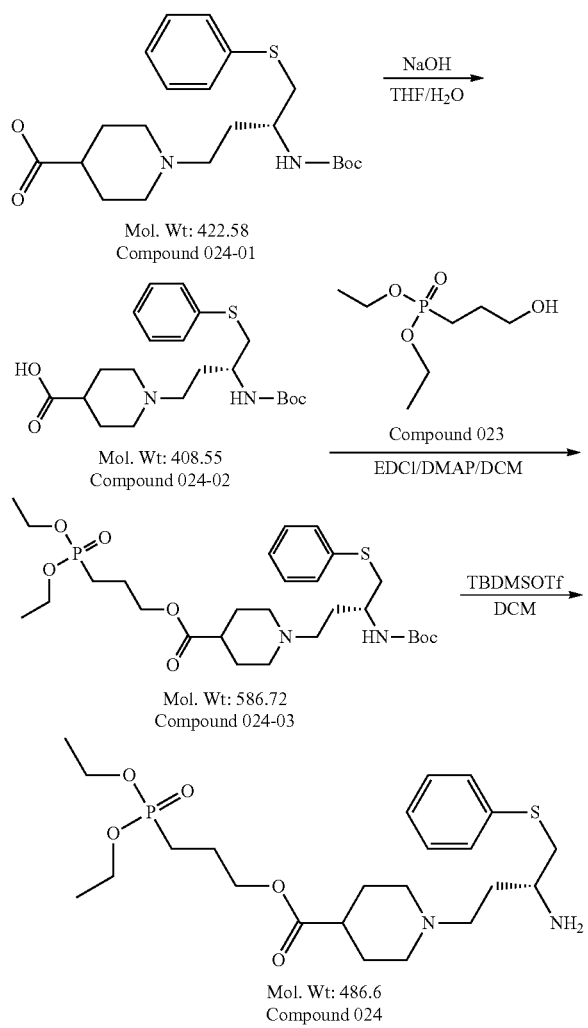

The Step 1: Preparation of Compound 024-02

Compound 024-01 (1.2 Kg) was added to THF (8.0 Kg) under stirring; NaOH (0.46 Kg) was dissolved in $H_2O$ (3.3 Kg), and added to the reaction system. The reaction system was stirred at room temperature overnight. The reaction system was adjusted to pH 3-4, and extracted with DCM. The organic phase was combined and concentrated to remove most of the solvent. The mixture was diluted with DCM, washed with saturated brine, allowed to stand to separate into layers. The organic phase was dried over MgSO4, filtered and concentrated. The crude product was dissolved in DCM and directly subjected to subsequent reaction.

Step 2: Preparation of Compound 024-03

Compound 024-02 (1.2 Kg) was added to DCM (12.5 Kg) under stirring; DMAP (0.70 Kg), EDCI (1.1 Kg), and compound 023 (0.65 Kg) were added in sequence. The mixture was stirred at room temperature for 4 hours under nitrogen gas protection. The reaction was stopped and the reaction solution was washed. The organic phase was concentrated to 5 L and used directly for subsequent reaction.

$^1$H NMR (400 MHz, chloroform-d) δ 7.39 (dd, J=7.8, 1.7 Hz, 2H), 7.27 (dd, J=8.5, 6.9 Hz, 2H), 7.21-7.12 (m, 1H), 5.87 (s, 1H), 4.16-4.04 (m, 6H), 3.83 (s, 1H), 3.23 (d, J=12.1 Hz, 1H), 2.99 (dd, J=12.7, 7.0 Hz, 1H), 2.84 (s, 2H), 2.47-2.23 (m, 3H), 2.06-1.62 (m, 12H), 1.41 (s, 9H), 1.32 (t, J=7.1 Hz, 6H).

Step 3: Preparation of Compound 024

Compound 024-03 (1.5 Kg) was added to DCM (18.4 Kg) under stirring; the mixture was cooled to <5° C. under nitrogen gas protection; TBDMSOTf (tert-butyldimethylsilyl trifluoromethanesulfonate) (1.4 Kg) was added. After the addition, the temperature was raised by 10 to 15° C., and the reaction was stirred for 2 hours. The reaction system was extracted with $H_2O$ until the sticky matter disappeared. The aqueous phase was combined, washed with DCM until the organic phase was substantially free of ultraviolet. The pH of aqueous phase was adjusted to ~8 with saturated $NaHCO_3$, stirred for 0.5 hour. The aqueous phase was extracted with DCM. The organic phase was combined. The organic phase was washed and concentrated to give 1266 g of oil. (Three-step total yield: 90%)

Compound 024: $^1$H NMR (400 MHz, DMSO-$d_6$) δ 7.40-7.24 (m, 4H), 7.17 (ddq, J=9.2, 7.3, 1.2 Hz, 1H), 4.10-3.92 (m, 6H), 3.05 (q, J=8.3 Hz, 1H), 2.80 (dt, J=21.9, 9.5 Hz, 4H), 2.43-2.22 (m, 3H), 1.89 (t, J=11.3 Hz, 2H), 1.83-1.71 (m, 6H), 1.51 (d, J=12.4 Hz, 6H), 1.23 (td, J=7.1, 0.8 Hz, 6H).

The compound of formula (2) of the present invention is stable in dichloromethane (DCM) used in the step (1), but the compound of formula (2) is not very stable in DMF and ethyl acetate. For example, the compound 024 is stable at 7° C. for at least about 13 days in dichloromethane solution. However, under the same conditions, the stability of compound 024 is slightly poor in ethyl acetate.

The process for preparing a novel sulfonamide compound provided by the invention significantly reduces the production cost, shortens the production cycle by at least half, and significantly improves the product yield, and is more suitable for mass production.

What is claimed is:

1. A process for preparing a compound of formula (I):

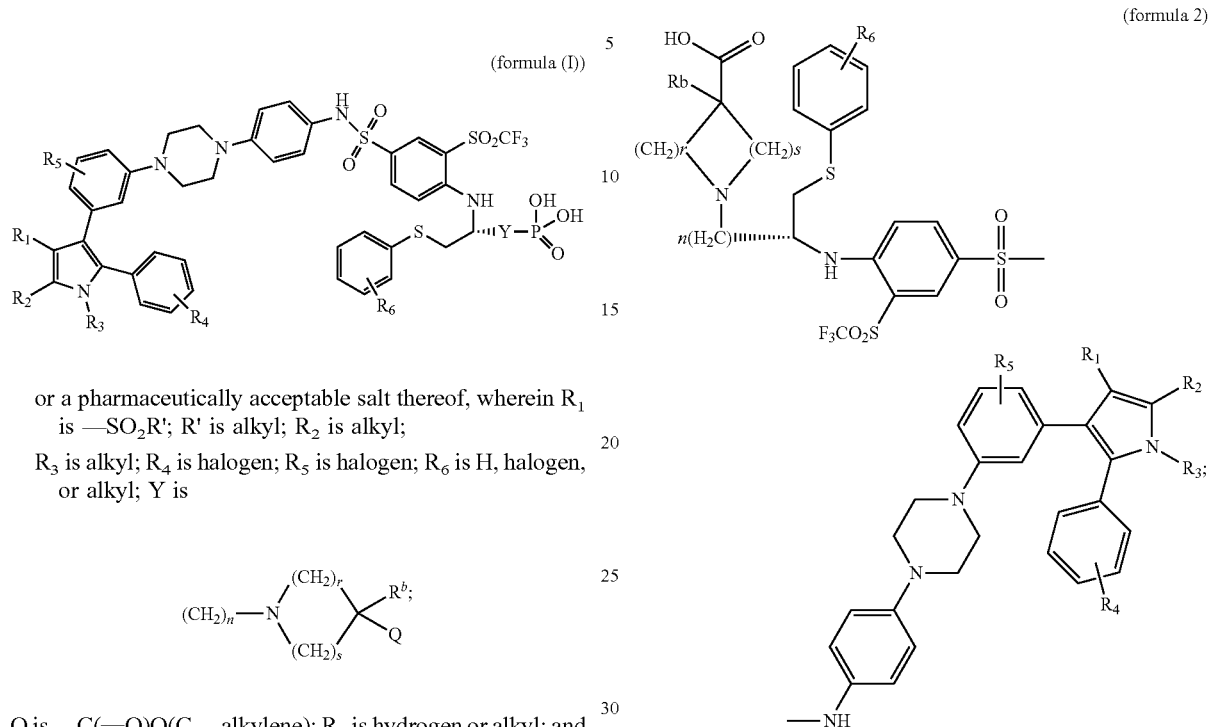

or a pharmaceutically acceptable salt thereof, wherein $R_1$ is —$SO_2R'$; R' is alkyl; $R_2$ is alkyl; $R_3$ is alkyl; $R_4$ is halogen; $R_5$ is halogen; $R_6$ is H, halogen, or alkyl; Y is Q is —C(=O)O($C_{1-5}$ alkylene); $R_b$ is hydrogen or alkyl; and n, r and s each independently are 1, 2, 3, 4, 5, or 6;

wherein the process comprises 1) converting a compound of formula 1:

to form a compound of formula 2:

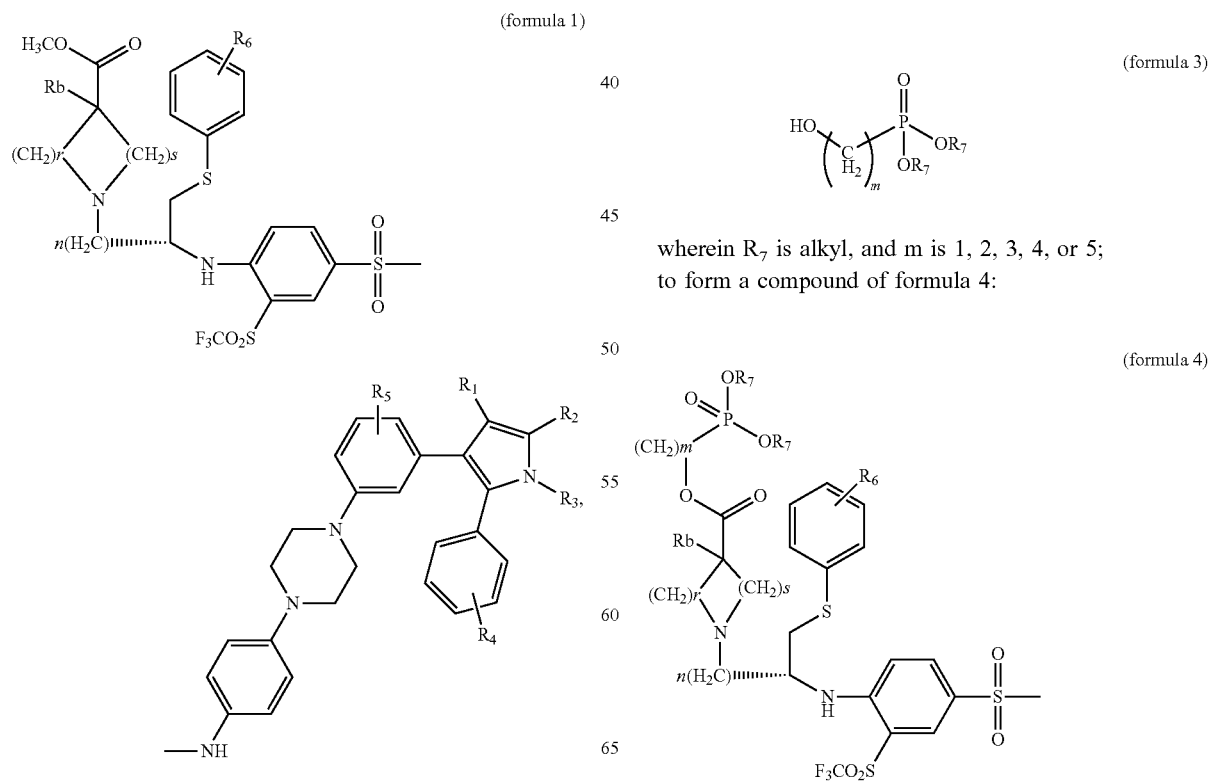

and wherein the process further comprises one or more of the following steps:

2) reacting the compound of formula 2 with a compound of formula 3:

wherein $R_7$ is alkyl, and m is 1, 2, 3, 4, or 5;
to form a compound of formula 4:

-continued

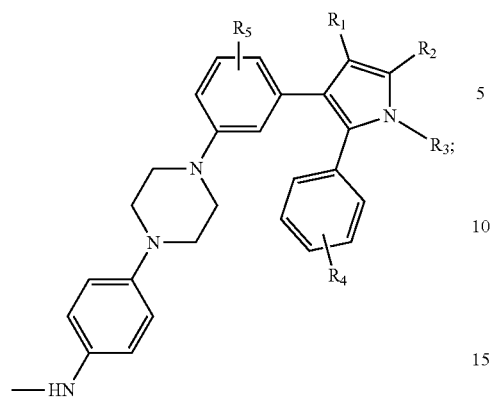

3) converting the compound of formula 4 to form a compound of formula 5:

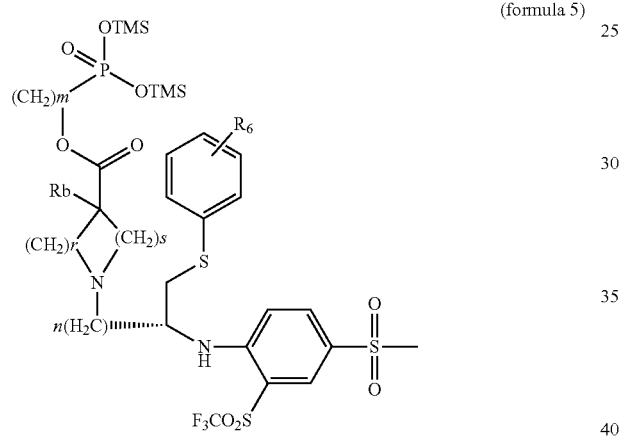

(formula 5)

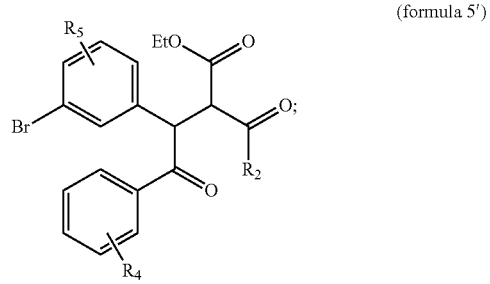

and 4) converting the compound of formula 5 to form the compound of formula (I); and wherein the compound of formula 1 is prepared by a method comprising one or more of the following steps:

1') reacting a compound of formula 1':

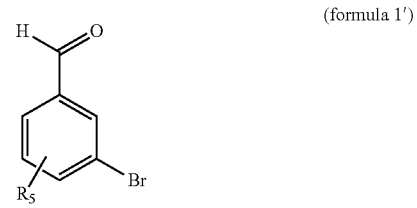

(formula 1')

with a compound of formula 2':

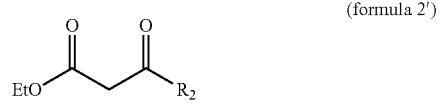

(formula 2')

to form a compound of formula 3':

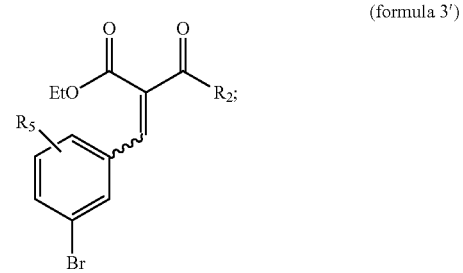

(formula 3')

2') reacting the compound of formula 3' with a compound of formula 4':

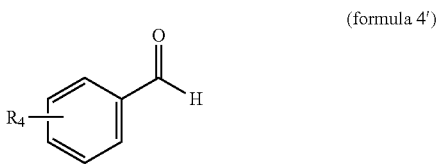

(formula 4')

to form a compound of formula 5':

(formula 5')

3') reacting the compound of formula 5' with a compound of formula 6':

(formula 6')

to form a compound of formula 7',

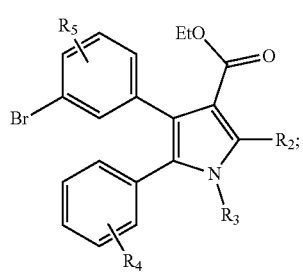
(formula 7')

4') converting the compound of formula 7' to form a compound of formula 8':

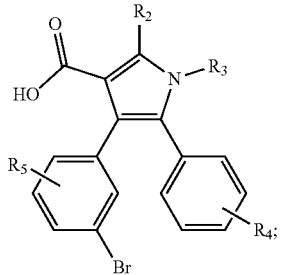
(formula 8')

5') converting the compound of formula 8' to form a compound of formula 9':

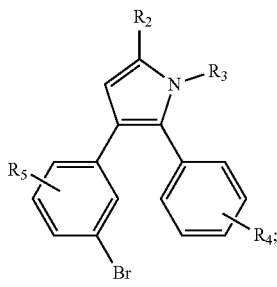
(formula 9')

6') converting the compound of formula 9' to form a compound of formula 10':

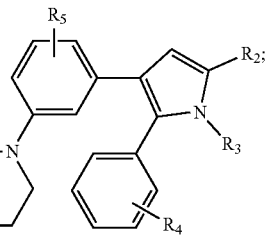
(formula 10')

7') converting the compound of formula 10' to form a compound of formula 11':

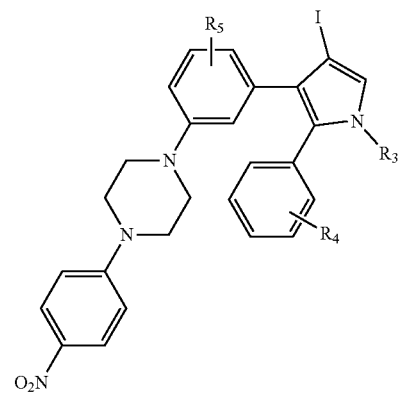
(formula 11')

8') reacting the compound of formula 11' with a compound of formula 12':

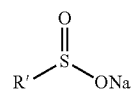
(formula 12')

to form a compound of formula 13':

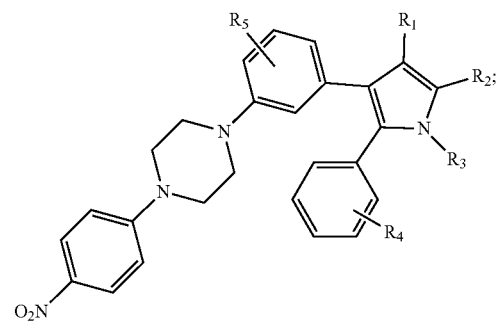
(formula 13')

9') converting the compound of formula 13' to form a compound of formula 14',

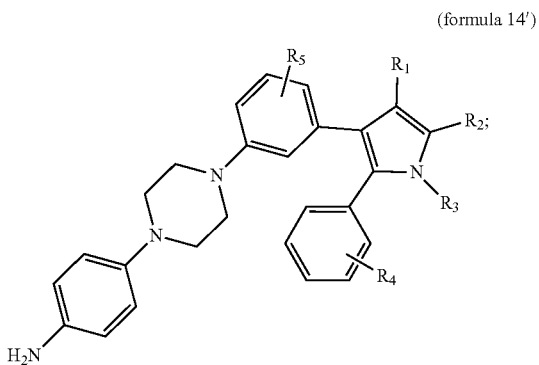
(formula 14')

10') reacting the compound of formula 14' with a compound of formula 15':

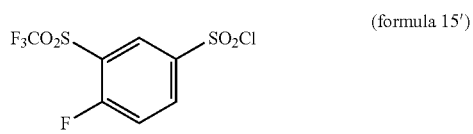
(formula 15')

to form a compound of formula 16':

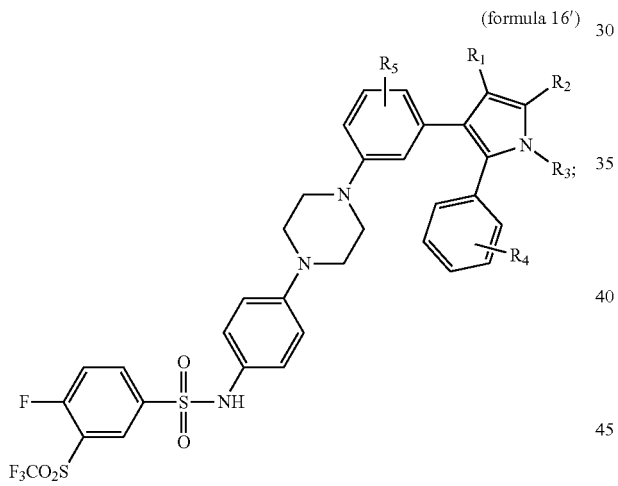
(formula 16')

and
11') reacting the compound of formula 16' with a compound of formula 17':

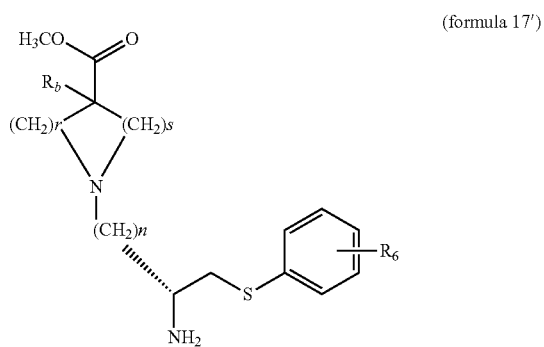
(formula 17')

to form a compound of formula 1.

2. The process of claim 1, having one or more of the following characteristics:
step 1) is carried out in a solvent in the presence of a base;
step 2) is carried out in the presence of a condensing agent and a catalyst in a polar organic solvent;
step 3) is carried out in the presence of a trialkylbromosilane;
step 4) is carried out in a polar solvent;
step 4) is carried out in the presence of bicarbonate salt and an acid; and
step 4) comprises purification by a preparative high-performance liquid chromatograph and removal of the solvent by freeze-drying.

3. The process of claim 1, wherein the method of preparing the compound of formula 1 has one or more of the following characteristics:
step 1') is carried out in an organic solvent
step 2') is carried out in the presence of a catalyst and a base;
step 3') is carried out in the presence of an organic acid and an organic base, in an organic solvent;
step 4') is carried out in the presence of a base, in a polar solvent;
step 5') is carried out in the presence of an organic acid, in a polar organic solvent;
step 6') is carried out in the presence of

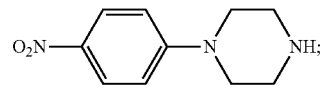 [SMILES: O=[N+]([O-])c1ccc(N2CCNCC2)cc1]

step 6') is carried out at a temperature of 120±5° C.;
step 7') is carried out in the presence of N-iodosuccinimide in an organic solvent;
step 8') is carried out in the presence of a metal iodide in an organic solvent;
step 8') is carried out at a temperature of 100±5° C.;
step 9') is carried out in the presence of hydrogen and a catalyst in an organic solvent,
step 10') is carried out in an organic solvent in the presence of a base; and
step 11') is carried out in a polar organic solvent in the presence of a base.

4. The process of claim 1, wherein the compound of formula 17' is prepared by a method comprising one or more of the following steps:
1") converting a compound of formula 1":

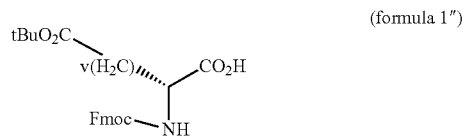
(formula 1")

wherein v is n-1;
to form a compound of formula 2":

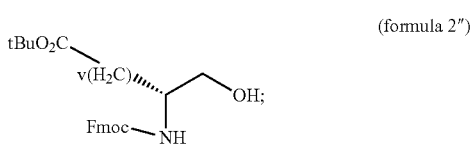
(formula 2")

2") converting the compound of formula 2" to form a compound of formula 3":

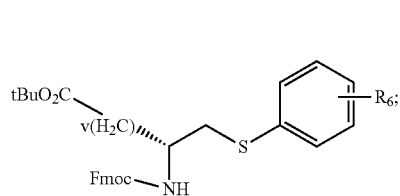
(formula 3")

3") converting the compound of formula 3" to form a compound of formula 4":

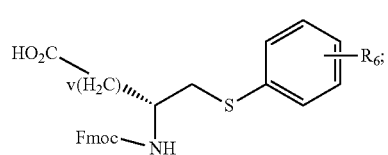
(formula 4")

4") converting the compound of formula 4" to form a compound of formula 5":

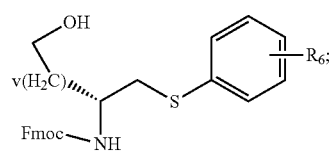
(formula 5")

5") converting the compound of formula 5" to form a compound of formula 6":

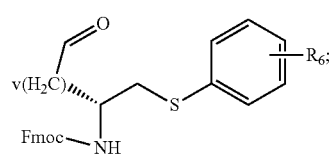
(formula 6")

6") reacting the compound of formula 6" with a compound of formula 7":

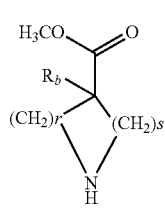
(formula 7")

to form a compound of formula 8",

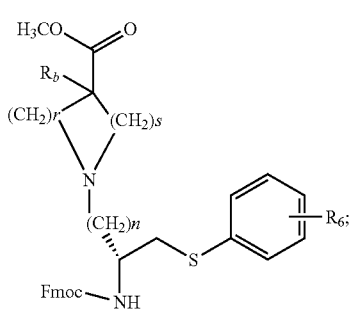
(formula 8")

and

7") converting the compound of formula 8" to form the compound of formula 17'.

5. The process of claim 4, having one or more of the following characteristics:

step 1") comprises the following steps:
(a) reacting the compound of formula 1" with isobutyl chloroformate in the presence of N methylmorpholine, and in ethylene glycol dimethyl ether; and
(b) reacting the product of step 1")(a) with an aqueous solution of sodium borohydride;

step 2") is carried out in the presence of diphenyl disulfide and a trialkylphosphine, in a polar organic solvent;

step 3") is carried out in the presence of an organic acid-in a polar organic solvent;

step 4") comprises the following steps:
(c) reacting the compound of the formula 4" with isobutyl chloroformate in the presence of N methylmorpholine, and in ethylene glycol dimethyl ether; and
(d) reacting the product of step 4")(c) with an aqueous solution of sodium borohydride;

step 5") is carried out in the presence of oxalyl chloride, dimethyl sulfoxide, and diisopropylethylamine, in dichloromethane;

step 6") is carried out in the presence of sodium triacetoxyborohydride in a polar organic solvent; and step 7") is carried out in the presence of diethylamine in a polar solvent.

6. The process of claim 1, wherein the compound of formula 3 is prepared by a method comprising the following step:

1''') converting a compound of formula 1''' to form the compound of formula 3:

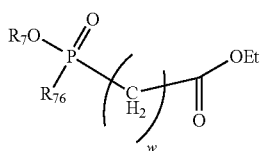
(formula 1''')

wherein w is 1, 2, 3, 4, or 5.

7. The process of claim 1, wherein the compound of formula 3 is prepared by a method comprising one or more of the following steps:

1″″) converting a compound of formula 1″″:

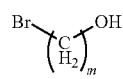
(formula 1″″)

wherein m is 1, 2, 3, 4, or 5; to form a compound of formula 2″″:

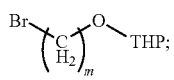
formula 2″″

2″″) converting the compound of formula 2″″ to form a compound of formula 3″″:

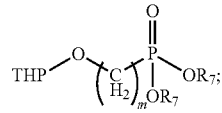
formula 3″″ and

3″″) converting the compound of formula 3″″ to form the compound of formula 3.

8. The process of claim 1, wherein the compound of formula (1) is prepared by a method comprising one or both of the following steps:

(1′) converting a compound of formula (1′):

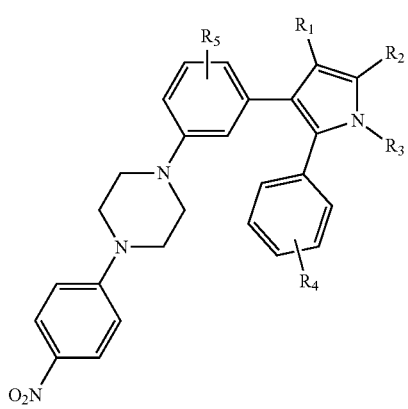
(formula (1′))

to form a compound of formula (2′):

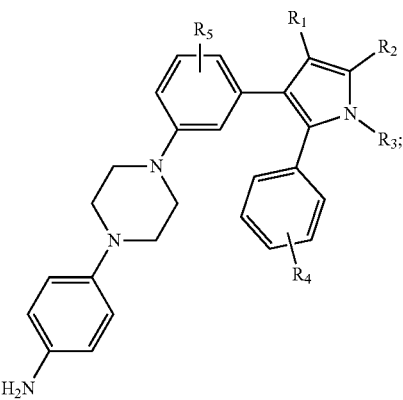
(formula (2′))

and converting the compound of formula (2′) to form the compound of formula (1).

9. The process of claim 8, wherein the compound of formula (1′) is prepared by a method comprising one or more of the following steps:

(1″) converting a compound of formula (1″):

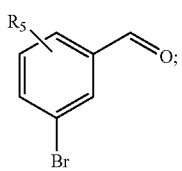
(formula (1″))

to form a compound of formula (2″):

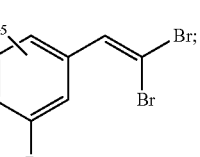
(formula (2″))

(2″) converting the compound of formula (2″) to form a compound of formula (3″):

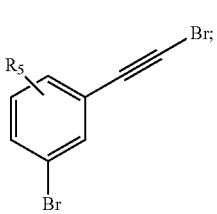
(formula (3″))

(3") converting the compound of formula (3") to form a compound of formula (4"):

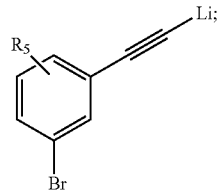

(formula (4"))

(4") converting the compound of formula (4") to form a compound of formula (5"):

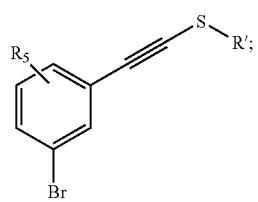

(formula (5"))

(5") converting the compound of formula (5") to form a compound of formula (6"):

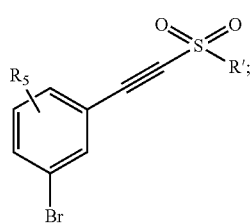

(formula (6"))

(6") reacting the compound of formula (6") with a compound of formula (7"):

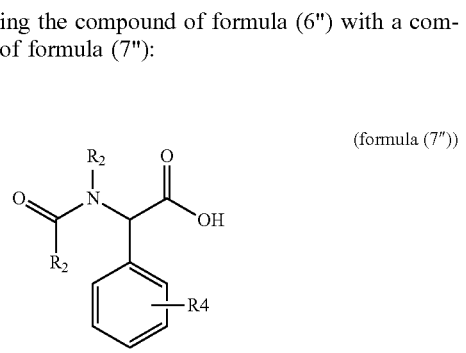

(formula (7"))

to form a compound of formula (8"):

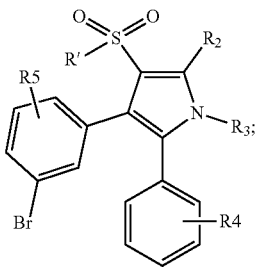

(formula (8"))

(7") converting the compound of formula (8") to form a compound of formula (9"):

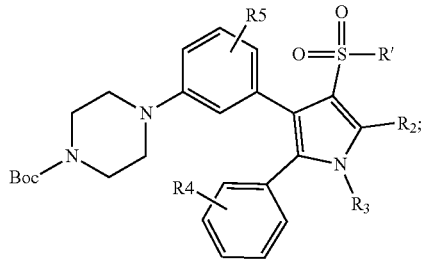

(formula (9"))

(8") converting the compound of formula (9") to form a compound of formula (10"):

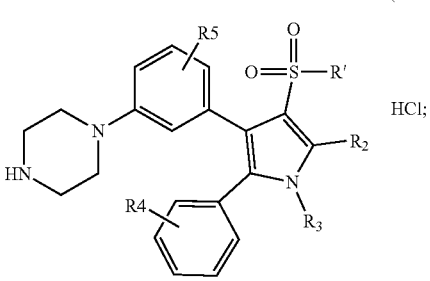

(formula (10"))

(9") converting the compound of formula (10") to form a compound of formula (1').

10. The process of claim 9 wherein the compound of formula (7") is prepared by a method comprising one or more of the following steps:

(1''') converting a compound of formula (1'''):

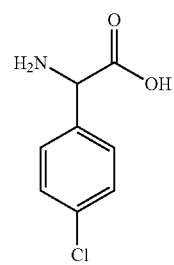

(formula (1'''))

to form a compound of formula (2′′′):
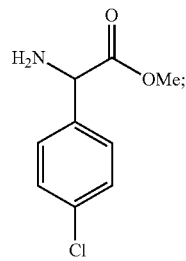
(formula (2′′′))
(2′′′) converting the compound of formula (2′′′) to form a compound of formula (3′′′):
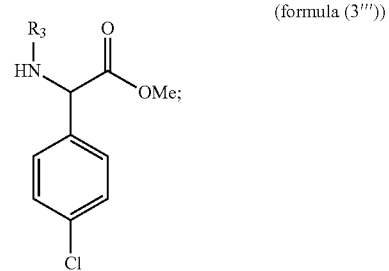
(formula (3′′′))
(3′′′) converting the compound of formula (3′′′) to form the compound of formula (7′′).
11. The process of claim 1, wherein the compound of formula (I) is:
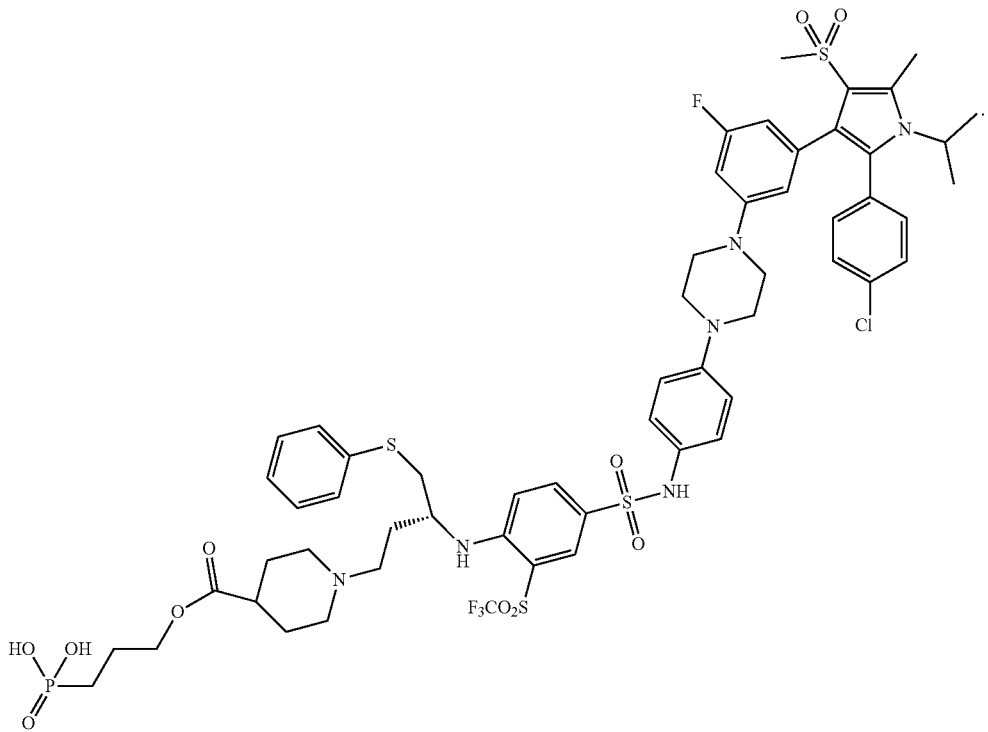
* * * * *